US009719960B2

(12) United States Patent
Medoro et al.

(10) Patent No.: US 9,719,960 B2
(45) Date of Patent: Aug. 1, 2017

(54) METHOD AND APPARATUS FOR THE MANIPULATION AND/OR THE DETECTION OF PARTICLES

(71) Applicant: Menarini Silicon Biosystems S.p.A., Castel Maggiore (IT)

(72) Inventors: Gianni Medoro, Casalecchio di Reno (IT); Nicolò Manaresi, Bologna (IT)

(73) Assignee: MENARINI SILICON BIOSYSTEMS S.P.A., Castel Maggiore (IT)

( * ) Notice: Subject to any disclaimer, the term of this patent is extended or adjusted under 35 U.S.C. 154(b) by 529 days.

(21) Appl. No.: 14/159,725

(22) Filed: Jan. 21, 2014

(65) Prior Publication Data
US 2014/0131207 A1     May 15, 2014

Related U.S. Application Data

(62) Division of application No. 11/996,068, filed as application No. PCT/IB2006/001984 on Jul. 19, 2006, now Pat. No. 8,641,880.

(30) Foreign Application Priority Data

Jul. 19, 2005  (IT) ............................. BO2005A0481

(51) Int. Cl.
| G01N 27/327 | (2006.01) |
| G01N 27/447 | (2006.01) |
| B03C 5/02 | (2006.01) |
| G01N 15/10 | (2006.01) |
| G01N 15/14 | (2006.01) |

(52) U.S. Cl.
CPC ....... *G01N 27/44756* (2013.01); *B03C 5/026* (2013.01); *G01N 15/1031* (2013.01); *G01N 15/1459* (2013.01); *B03C 2201/24* (2013.01)

(58) Field of Classification Search
CPC .............. G01N 27/44756; B03C 5/026; B03C 2201/24
See application file for complete search history.

(56) References Cited

U.S. PATENT DOCUMENTS

| 4,682,007 A | 7/1987 | Hollander |
| 5,252,493 A | 10/1993 | Fujiwara et al. |
(Continued)

FOREIGN PATENT DOCUMENTS

| DE | 3931851 A1 | 4/1991 |
| DE | 10203636 A1 | 8/2003 |
(Continued)

OTHER PUBLICATIONS

Altomare et al., Levitation and movement of human tumor cells using a printed circuit board device based on software-controlled dielectrophoresis, Biotechnol. Bioeng., 82(4):474-9 (2003).
(Continued)

*Primary Examiner* — J. Christopher Ball
(74) *Attorney, Agent, or Firm* — Marshall, Gerstein & Borun LLP

(57) ABSTRACT

Method and apparatus for the manipulation and/or control of the position of particles using time-variable fields of force; the fields of force can be of dielectrophoresis (positive or negative), electrophoresis, electrohydrodynamic or electrowetting on dielectric, possessing a set of stable points of equilibrium for the particles.

8 Claims, 29 Drawing Sheets

(56) References Cited

U.S. PATENT DOCUMENTS

| | | |
|---|---|---|
| 5,279,493 A | 1/1994 | Halder |
| 5,833,860 A | 11/1998 | Kopaciewicz et al. |
| 5,888,370 A | 3/1999 | Becker et al. |
| 5,888,730 A | 3/1999 | Gray et al. |
| 5,942,443 A | 8/1999 | Parce et al. |
| 5,945,281 A | 8/1999 | Prabhu |
| 6,149,489 A | 11/2000 | Johnson |
| 6,149,789 A | 11/2000 | Benecke et al. |
| 6,203,683 B1 | 3/2001 | Austin et al. |
| 6,264,815 B1 | 7/2001 | Pethig et al. |
| 6,294,063 B1 | 9/2001 | Becker et al. |
| 6,824,664 B1 | 11/2004 | Austin et al. |
| 6,830,729 B1 | 12/2004 | Holl et al. |
| 6,875,329 B2 | 4/2005 | Washizu et al. |
| 6,888,721 B1 | 5/2005 | Moghaddam et al. |
| 6,911,132 B2 | 6/2005 | Pamula et al. |
| 6,977,033 B2 | 12/2005 | Becker et al. |
| 7,147,763 B2 | 12/2006 | Elrod et al. |
| 7,250,933 B2 | 7/2007 | De Boer et al. |
| 7,307,328 B2 | 12/2007 | Meyer et al. |
| 7,488,406 B2 | 2/2009 | Hughes et al. |
| 7,641,779 B2 | 1/2010 | Becker et al. |
| 8,216,513 B2 | 7/2012 | Becker et al. |
| 8,349,160 B2 | 1/2013 | Medoro et al. |
| 8,388,823 B2 | 3/2013 | Manaresi et al. |
| 8,641,880 B2 | 2/2014 | Medoro et al. |
| 8,679,856 B2 | 3/2014 | Manaresi |
| 8,685,217 B2 | 4/2014 | Manaresi et al. |
| 9,310,287 B2 | 4/2016 | Medoro et al. |
| 2002/0031838 A1 | 3/2002 | Meinhart et al. |
| 2002/0036139 A1 | 3/2002 | Becker et al. |
| 2002/0070114 A1 | 6/2002 | Miles |
| 2002/0125138 A1 | 9/2002 | Medoro |
| 2002/0132316 A1 | 9/2002 | Wang et al. |
| 2002/0172987 A1 | 11/2002 | Terstappen et al. |
| 2002/0195342 A1 | 12/2002 | Lee et al. |
| 2003/0044832 A1 | 3/2003 | Blankenstein |
| 2003/0047456 A1 | 3/2003 | Medoro |
| 2003/0073110 A1 | 4/2003 | Aritomi et al. |
| 2003/0098271 A1 | 5/2003 | Somack et al. |
| 2004/0011652 A1 | 1/2004 | Bressler |
| 2004/0055891 A1 | 3/2004 | Pamula et al. |
| 2004/0058450 A1 | 3/2004 | Pamula et al. |
| 2004/0063196 A1 | 4/2004 | Muller et al. |
| 2004/0159546 A1 | 8/2004 | Zhang et al. |
| 2004/0191789 A1 | 9/2004 | Manaresi et al. |
| 2004/0209354 A1 | 10/2004 | Mathies et al. |
| 2004/0229210 A1 | 11/2004 | Sabry et al. |
| 2005/0009101 A1 | 1/2005 | Blackburn |
| 2005/0014146 A1 | 1/2005 | Manaresi et al. |
| 2005/0112541 A1 | 5/2005 | Durack et al. |
| 2005/0214736 A1 | 9/2005 | Childers et al. |
| 2006/0029923 A1 | 2/2006 | Togawa et al. |
| 2006/0037903 A1 | 2/2006 | Smith et al. |
| 2006/0051775 A1 | 3/2006 | Bianchi |
| 2006/0057738 A1 | 3/2006 | Hall |
| 2006/0072804 A1 | 4/2006 | Watson et al. |
| 2006/0086309 A1 | 4/2006 | Manger et al. |
| 2006/0139638 A1 | 6/2006 | Muller et al. |
| 2006/0177815 A1 | 8/2006 | Soh et al. |
| 2006/0223178 A1 | 10/2006 | Barber et al. |
| 2006/0228749 A1 | 10/2006 | Wang et al. |
| 2006/0290745 A1 | 12/2006 | Feng et al. |
| 2007/0015289 A1 | 1/2007 | Kao et al. |
| 2007/0026413 A1 | 2/2007 | Toner et al. |
| 2007/0026415 A1 | 2/2007 | Fuchs et al. |
| 2007/0051412 A1 | 3/2007 | Heath et al. |
| 2007/0059683 A1 | 3/2007 | Barber et al. |
| 2007/0172903 A1 | 7/2007 | Toner et al. |
| 2007/0190522 A1 | 8/2007 | Somack et al. |
| 2007/0195324 A1 | 8/2007 | Adams et al. |
| 2007/0250301 A1 | 10/2007 | Vaisberg et al. |
| 2008/0057572 A1 | 3/2008 | Petersen et al. |
| 2008/0058991 A1 | 3/2008 | Lee et al. |
| 2008/0246489 A1 | 10/2008 | Coster et al. |
| 2008/0264068 A1 | 10/2008 | Nakasuka et al. |
| 2009/0205963 A1 | 8/2009 | Medoro et al. |
| 2009/0218223 A1 | 9/2009 | Manaresi et al. |
| 2009/0288963 A1 | 11/2009 | Guerrieri et al. |
| 2010/0035292 A1 | 2/2010 | Levhenko et al. |
| 2010/0248285 A1 | 9/2010 | Manaresi |
| 2010/0331205 A1 | 12/2010 | Medoro |
| 2011/0003380 A1 | 1/2011 | Miltenyi et al. |
| 2011/0183433 A1 | 7/2011 | Motadel et al. |
| 2011/0193006 A1 | 8/2011 | Simone et al. |
| 2012/0071335 A1 | 3/2012 | Manaresi et al. |
| 2012/0091001 A1 | 4/2012 | Manaresi et al. |
| 2012/0184010 A1 | 7/2012 | Medoro et al. |
| 2013/0118903 A1 | 5/2013 | Becker et al. |
| 2014/0315236 A1 | 10/2014 | Manaresi |
| 2015/0126396 A1 | 5/2015 | Manaresi et al. |

FOREIGN PATENT DOCUMENTS

| | | |
|---|---|---|
| DE | 19500660 B4 | 12/2007 |
| EP | 0 500 727 A1 | 9/1992 |
| EP | 1145766 A2 | 10/2001 |
| EP | 1179585 A2 | 2/2002 |
| EP | 1304388 A2 | 4/2003 |
| EP | 2260943 A1 | 12/2010 |
| JP | 58211272 A | 12/1983 |
| JP | 2000292480 A | 10/2000 |
| JP | 2002503334 A | 1/2002 |
| JP | 2002311461 A | 10/2002 |
| JP | 2002536167 A | 10/2002 |
| JP | 2003121886 A | 4/2003 |
| JP | 2003202604 A | 7/2003 |
| JP | 2004000935 A | 1/2004 |
| JP | 2005501296 A | 1/2005 |
| JP | 2005507997 A | 3/2005 |
| JP | 2005510705 A | 4/2005 |
| JP | 2005176836 A | 7/2005 |
| JP | 2005257283 | 9/2005 |
| JP | 2005257283 A | 9/2005 |
| JP | 2005304445 A | 11/2005 |
| JP | 2006504974 A | 2/2006 |
| JP | 2006512092 A | 4/2006 |
| JP | 2006517024 A | 7/2006 |
| JP | 2007017163 A | 1/2007 |
| JP | 2008533487 A | 8/2008 |
| JP | 60071935 | 4/2015 |
| WO | WO-91/07660 A1 | 5/1991 |
| WO | WO-91/08284 A1 | 6/1991 |
| WO | WO-98/04355 A1 | 2/1998 |
| WO | WO-99/17883 A1 | 4/1999 |
| WO | WO-00/28313 A1 | 5/2000 |
| WO | WO-00/47322 A2 | 8/2000 |
| WO | WO-00/69525 A1 | 11/2000 |
| WO | WO-00/69565 A1 | 11/2000 |
| WO | WO-01/21311 A1 | 3/2001 |
| WO | WO-02/12896 A1 | 2/2002 |
| WO | WO-02/41999 A1 | 5/2002 |
| WO | WO-02/088702 A2 | 11/2002 |
| WO | WO-03/014739 A1 | 2/2003 |
| WO | WO-03/035895 A2 | 5/2003 |
| WO | WO-03/045556 A2 | 6/2003 |
| WO | WO-2004/030820 A2 | 4/2004 |
| WO | WO-2004/071668 A1 | 8/2004 |
| WO | WO-2005/060432 A2 | 7/2005 |
| WO | WO-2005/098395 A1 | 10/2005 |
| WO | WO-2006/003214 A2 | 1/2006 |
| WO | WO-2006/008602 A2 | 1/2006 |
| WO | WO-2006/018849 A2 | 2/2006 |
| WO | WO-2007/010367 A2 | 1/2007 |
| WO | WO-2007/049103 A1 | 5/2007 |
| WO | WO-2007/049120 A2 | 5/2007 |
| WO | WO-2007/110739 A2 | 10/2007 |
| WO | WO-2007/116312 A2 | 10/2007 |
| WO | WO-2007/147018 A1 | 12/2007 |
| WO | WO-2007/147076 A2 | 12/2007 |
| WO | WO-2008/011274 A2 | 1/2008 |
| WO | WO-2008/131035 A2 | 10/2008 |
| WO | WO-2009/022222 A2 | 2/2009 |

(56) References Cited

FOREIGN PATENT DOCUMENTS

| WO | WO-2010/106426 A1 | 9/2010 |
|----|-------------------|--------|
| WO | WO-2010/106434 A1 | 9/2010 |
| WO | WO-2010/149292 A1 | 12/2010 |

OTHER PUBLICATIONS

Berthier et al., NSTI Nanotech 2005, vol. 1 (2005), www.nsti.org.
Bonci et al., The miR-15a-miR-16-1 cluster controls prostate cancer by targeting multiple oncogenic activities, Nat. Med., 14:1271-7 (2008).
Cheung et al., Impedance spectroscopy flow cytometry: on-chip label-free cell differentiation, Cytometry Part A, 65A(2):124-32 (2005).
de Bono et al., Circulating tumor cells predict survival benefit from treatment in metastatic castration-resistant prostate cancer, Clin. Cancer Res., 14(19):6302-9 (2008).
Diamond et al., Flow cytometry in the diagnosis and classification of malignant lymphome and leukemia, Cancer, 50:1122-35 (1982).
English translation of Office Action, Japanese patent application No. 2012-167396 (Aug. 2, 2013).
Fiedler et al., Dielectrophoretic sorting of particles and cells in a microsystem, Anal. Chem., 80(9):1909-15 (1998).
Fiedler et al., Electrocasting formation and structuring of suspended microbodies using A.C. generated field cages, Microsystem Technologies, Berlin, Germany, pp. 1-7 (Dec. 1, 1995).
Final office action, U.S. Appl. No. 11/724,697, mail date Jan. 27, 2012.
Final office action, U.S. Appl. No. 12/091,367, mail date Nov. 1, 2011.
Fuchs et al., Electronic sorting and recovery of single live cells from microlitre sized samples, Lab Chip, 6:121-6 (2006).
Fuhr et al., Positioning and manipulation of cells and microparticles using miniturized electric field traps and travelling waves, Sensors and Materials, 7(2):131-146 (1995).
Gascoyne et al., Dielectrophoresis-based programmable fluidic processors, Lab Chip, 4:299-304 (2004).
Gascoyne et al., Particle separation by dielectrophoresis, Electrophoresis, 23(13): 1973-83 (2002).
Green et al., Ac Electrokinetics: a survey of sub-micrometre particle dynamics, J. Phys. D: Appl. Phys., 33:632-41 (Dec. 10, 1999).
Hughes, Strategies for dielectrophoretic separation in laboratory-on-a-chip systems, Electrophoresis, 23(16): 2569-82 (2002).
International Preliminary Report on Patentability for PCT/EP2005/053235, dated Jan. 9, 2007.
International Preliminary Report on Patentability for PCT/IB2009/007316, Jan. 21, 2011.
International Preliminary Report on Patentability for PCT/IB2006/000636, dated Apr. 29, 2008.
International Preliminary Report on Patentability for PCT/IB2006/001984, dated Dec. 3, 2007.
International Preliminary Report on Patentability for PCT/IB2006/002965, dated Apr. 29, 2008.
International Preliminary Report on Patentability for PCT/IB2007/000751, dated Sep. 30, 2008.
International Preliminary Report on Patentability for PCT/IB2010/000615, dated Sep. 20, 2011.
International Search Report and Written Opinion for PCT/EP2005/053235, mailing date May 2, 2006.
International Search Report and Written Opinion for PCT/IB2006/000636, dated Sep. 8, 2006.
International Search Report and Written Opinion for PCT/IB2006/001984, dated Feb. 27, 2007.
International Search Report and Written Opinion for PCT/IB2006/002965, dated Jun. 15, 2007.
International Search Report and Written Opinion for PCT/IB2007/000751, dated Nov. 16, 2007.
International Search Report and Written Opinion for PCT/IB2010/000615, mailing date Aug. 26, 2010.
International Search Report and Written Opinion for PCT/IB2012/057797, mailed May 8, 2013.
International Search Report for PCT/IB2008/002873, dated Aug. 3, 2009.
Jones, An electromechanical interpretation of electrowetting, J. Micromech. Microeng., 15(6):1184-7 (2005).
Klein et al., Comparative genomic hybridization, loss of heterozygosity, and DNA sequence analysis of single cells, Proc. Natl. Acad. Sci. USA, 96(8):4494-9 (1999).
Long et al., A new preprocessing approach for cell recognition, IEEE Trans. Information Tech. Biomed., 9(3):407-12 (2005).
Manaresi et al., A CMOS chip for individual cell manipulation and detection, IEEE Journal of Solid-State Circuits, 38 (12):2297-305 (2003).
Medoro et al., A lab-on-a-chip for cell detection and manipulation, IEEE Sensors Journal, 3(3):317-25 (2003).
Medoro et al., A lab-on-a-chip for cell separation based on the moving-cages approach, Proceedings of the 16th Conference on Solid State Transducers, pp. 500-501 (Sep. 15, 2002).
Medoro et al., Dielectrophoretic cage-speed separation of bio-particles, Sensors, Proceedings of the IEEE Vienna, Austria, Oct. 24-27, 2004, pp. 76-79.
Milner et al., Dielectrophoretic classification of bacteria using differential impedance measurements, Electronics Letters, 34(1):66-8 (1998).
Nagrath et al., Isolation of rare circulating tumour cells in cancer patients by microchip technology, Nature, 450(7173):1235-9 (2007).
Nieuwenhuis et al., Near-field optical sensors for particle shape measurements, Sensors Journal IEEE, 3(5):646-51 (2003).
Nonfinal office action, U.S. Appl. No. 11/724,697, notification date Jun. 7, 2011.
Nonfinal office action, U.S. Appl. No. 11/724,697, notification date Sep. 23, 2010.
Nonfinal office action, U.S. Appl. No. 12/091,367, mail date Mar. 25, 2011.
Nonfinal office action, U.S. Appl. No. 12/091,438, mail date Jul. 25, 2013.
Nonfinal office action, U.S. Appl. No. 12/294,860, mail date Jan. 27, 2012.
Nonfinal office action, U.S. Appl. No. 12/740,170, mail date Jun. 5, 2013.
O'Hara et al., Ratcheting electrophoresis microchip (REM) for programmable transport and separation of macromolecules, Proceedings of the International Mechanical Engineering Congress and Exposition, 3:619-28 (2001).
Ohta et al., Tech. Dig. of the Solid State Sensor, Actuator and Microsystems, Workshop, pp. 216-219 (2004).
Petersson et al., Carrier medium exchange through ultrasonic particle switching in microfluidic channels, Anal. Chem., 77:1216-21 (2005).
Pethig et al., Enhancing traveling-wave dielectrophoresis with signal superposition, IEEE Eng. Med. Biol. Mag., 22(6):43-50 (2003).
Reichle et al., Combined laser tweezers and dielectric field cage for the analysis of receptor-ligand interactions on single cells, Electrophoresis, 22(2):272-82 (2001).
Romani et al., Capacitive sensor array for localization of bioparticles in CMOS lab-on-a-chip, Proc. Int. Solid State Circuit Conference, 1:224-5 (2004).
Rousselet et al., Directional motion of brownian particles induced by a periodic asymmetric potential, Nature, 370(6489):446-8 (1994).
Schnelle et al., Three-dimensional electric field traps for manipulation of cells—calculation and experimental verfication, Biochem. Biophys. Acta, 1157(2):127-40 (1993).
Stoecklein et al., Direct genetic analysis of single disseminated cancer cells for prediction of outcome and therapy selection in esophageal cancer, Cancer Cell, 13:441-53 (2008).
Suehiro, The dielectrophoretic movement and positioning of a biological cell using a three-dimensional grid electrode system, J. Phys. D: Appl. Phys., 31:3298-305 (1998).
Zieglschmid et al., Detection of disseminated tumor cells in peripheral blood, Crit. Rev. Clin. Lab. Sci., 42(2):155-96 (2005).

(56) References Cited

OTHER PUBLICATIONS

Corver et al., High-resolution multiparameter DNA flow cytometry for the detection and sorting of tumor and stromal subpopulations from paraffin-embedded tissues, Curr. Protoc. Cytom., Chapter 6, Unit 6.27 (2009).
International Preliminary Report on Patentability for PCT/IB2012/057797, dated Jul. 1, 2014.
International Preliminary Report on Patentability for PCT/IB2008/002873, dated May 4, 2010.
International Preliminary Report on Patentability for PCT/IB2012/055981, dated Apr. 29, 2014.
International Search Report and Written Opinion for PCT/IB2009/007316, mailed Feb. 3, 2010.
International Search Report and Written Opinion for PCT/IB2012/055981, dated Jan. 22, 2013.
Nonfinal office action, U.S. Appl. No. 11/996,068, mail date Jan. 4, 2013.
Vona et al., Isolation by size of epithelial tumor cells : a new method for the immunomorphological and molecular characterization of circulatingtumor cells, Am. J. Pathol., 156(1):57-63 (2000).

- ■ Fase 1 (V1)
- ▨ Fase 2 (V2)
- ☐ Fase 3 (V3)
- ▤ Fase positiva
- ▨ Fase dummy

METHOD AND APPARATUS FOR THE MANIPULATION AND/OR THE DETECTION OF PARTICLES

CROSS-REFERENCE TO RELATED APPLICATIONS

This application is a divisional of U.S. application Ser. No. 11/996,068, filed Oct. 7, 2008, which is the U.S. national phase of PCT/IB2006/001984 filed Jul. 19, 2006, based on BO2005A00481 filed Jul. 19, 2005, the disclosures of which are each hereby incorporated herein by reference in their entireties.

FIELD OF THE INVENTION

The present invention relates to methods and apparatuses for the manipulation and/or detection of particles. The invention finds application principally in the implementation of biological protocols on individual cells.

BACKGROUND OF THE INVENTION

The patent No. PCT/WO 00/69565 in the name of G. Medoro describes an apparatus and a method for the manipulation of particles via the use of closed dielectrophoretic-potential cages. The method described teaches how to control the position of each particle independently of all the others in a two-dimensional space. The force used for entrapping the particles in suspension is negative dielectrophoresis. The individual control on the operations of manipulation is carried out by programming memory elements and circuits associated to each element of an array of electrodes integrated in one and the same substrate. There follows an important limitation due to the dimensions of each trap, limited by the need to integrate in the space corresponding to an individual electrode the electronics necessary for programming. Furthermore described in G. Medoro et al., 3, 317-325 (2003) *IEEE Sensors Journal* is an apparatus for the manipulation of cells based upon the use of parallel elongated electrodes, control of which does not require the use of transistors integrated in the substrate itself. The shape and spatial distribution of the elongated electrodes enables creation of traps of a cylindrical shape, by means of which it is possible to entrap groups of particles. There follows an important limitation due to the impossibility in the independent manipulation of individual particles.

Other methods for the manipulation of particles based upon dielectrophoresis do not enable independent control on a multiplicity of particles, as described by T. Schnelle et al., *Biochim. Biophys. Acta* 1157, 127-140 (1993). There follows an important limitation in the applications that require the study of the interaction between a multiplicity of cells.

Other methods based upon dielectrophoresis require direct contact between cells and substrate, since they make use of the force of positive dielectrophoresis (PDEP). In particular, described in J. Suchiro, *J. Phys. D: Appl. Phys.*, 31, 3298-3305 (1998) is a method that envisages the creation of traps capable of attracting to the substrate a particle by means of forces of positive dielectrophoresis (PDEP). The particle consequently adheres to the substrate, from which it can be detached and pushed towards a new region by means of an appropriate distribution of force of negative dielectrophoresis (NDEP). In addition to the risk of causing irreparable damage to the cells, there follow some important limitations, such as for example the impossibility of using physiological solutions with high electrical conductivity or the impossibility of operating with polystyrene microspheres, since in both cases there do not exist the conditions necessary for activating the force of positive dielectrophoresis.

Likewise, the U.S. Pat. No. 6,294,063 in the name of Becker et al. describes a method and apparatus for the manipulation of packets of solid, liquid or gaseous biological material by means of a distribution of programmable forces. Also in this case the contact with a surface of reaction is a requisite indispensable for the operation of the method and apparatus. But the biggest limitation is linked to the need for a number of control signals (n×m) corresponding to the number of electrodes (n×m) if it is desired to use a passive substrate (and hence a less costly one). In order to increase the number of electrodes of the order of many hundreds or thousands it is necessary to use an active substrate, as explained in P. R. C. Gascoyne et al., *Lab Chip*, 2004, 4, 299-309, which includes transistors for addressing individually the n×m electrodes and generating locally the control signals. In this way, the number of input signals to the chip can be maintained within acceptable limits.

Another known method for the manipulation of liquid particles (droplets) is electro-wetting on dielectric (EWOD), described in T. B. Jones, *Journal of Micromechanics and Microengineering*, 15 (2005) 1184-1187. In this case, an electrical field exerted by electrodes made on a substrate enables the propulsion of a droplet surrounded by a gaseous phase in a direction controlled by the sequence of energized electrodes. Devices based upon this principle can be obtained by including a lid (also this coated with a dielectric), as is taught by the patent application No. US 2004/0058450A1 in the name of Pamula et al., or also simply a wire referred to as "chain", which establishes the electrical contact with the droplets on top of the substrate J. Berthier et al., *NSTI Nanotech* 2005, www.nsti.org, vol. 1, 2005. In a way similar to what has been discussed above regarding the use of dielectrophoresis, in order to manipulate particles on a complete two-dimensional array via EWOD the embodiments reported in the known art resort either to a use of input signals corresponding to the number of electrodes of the array or to the use of an active substrate with transistors.

A further force for the manipulation of particles is the force of viscous friction generated by electro-hydrodynamic (EHD) flows, such as electrothermal (ETF) flows or AC electro-osmosis. In N. G. Green, A. Ramos and H. Morgan, *J. Phys. D: Appl. Phys.* 33 (2000) EHD flows are used to displace particles. For example, the patent No. PCT WO 2004/071668 A1 describes an apparatus for concentrating particles on the electrodes, exploiting the aforesaid electrohydrodynamic flows.

Other methods are known for the individual manipulation particles in a two-dimensional space. These, however, involve the use of so-called optical or optoelectronic tweezers, i.e., programmable external light sources. The result is a cumbersome and costly system, which is an undesirable characteristic in many applications. In particular A. T. Ohta et al., *Tech. Dig. of the Solid-State Sensor, Actuator and Microsystems. Workshop*, 216-219, (2004) describes a possible implementation of said techniques.

The limitations of the known art are overcome by the present invention, which enables independent manipulation of a multiplicity of particles in a two-dimensional space, with or without contact depending upon the forces used. The implementation of the method according to the invention does not require the use of electronic circuits or memory elements integrated in the substrate. Different embodiments of the method and apparatus according to the present invention enable manipulation of particles in an nm two-dimensional array of arbitrary size, with a number of control signals of the order of n+m, or else n, or else even with less than ten control signals, reducing, according to different compromises, the parallelism and flexibility of movement of the particles, and consequently the number of steps to perform a series of displacements (a parameter that is obviously linked to the time of execution).

Even though the methods of the invention can be conducted with substrates without transistors, it is possible, however, to benefit from the use of active substrates to reduce the overall dimensions of the individual elements of the array that constitute the apparatus according to the invention as compared to the known art or to reduce the overall number of the external control signals.

In addition to the possibility of manipulation of cells, the present invention teaches how to combine manipulation and detection by integrating said operations on the same substrate or interfacing sensors and actuators made on different substrates depending upon the technology used.

SUMMARY OF THE INVENTION

The present invention relates to a method and apparatus for the manipulation of particles (in an extensive sense, as described hereinafter) by means of time-variable non-uniform fields of force, and/or for their detection. The fields of force can be of positive dielectrophoresis or negative dielectrophoresis, electrophoresis or any electro-hydrodynamic motion, characterized by a set of stable points of equilibrium for the particles (solid, liquid or gaseous). The same method is adaptable to the manipulation of droplets (liquid particles), exploiting effects known to the international scientific community under the name of "electrowetting on dielectric" (EWOD). The aim of the present invention is to act on control of the position of each particle present in the sample, for the purpose of displacing said particles independently of one another from an initial position to any element belonging to the set of the final positions in a given space within a microchamber of the device.

In a first embodiment of the method, each point of equilibrium in a homogeneous array of elements can contain a particle or a group of particles. Each of said points of equilibrium can be joined without distinction to any one of the adjacent points of equilibrium, allowing the entrapped particles to share the basin of attraction thereof. This control is made by acting exclusively on the signals shared by all the elements belonging to the same row or column, used for distributing the voltages necessary for generation of the forces. According to the present invention, each path can be broken down into a succession of elementary steps constituted by the union of adjacent basins of attraction, thus allowing each particle to be guided from the initial position to a final destination. Forming the subject of the present invention are also some practical implementations of the method by means of apparatuses constituted by n+m+2 control signals and by n+2 m+2 control signals for arrays of size nxm.

In a second embodiment of the method, the control is made by acting exclusively on the digital signals used for controlling a deviator associated to each element of the array, through which to distribute the voltages necessary for generation of the forces. The object of the present invention is also an apparatus constituted by n+m digital signals for control of the distribution of the two voltages necessary for generation of the forces in an nxm array.

In a further embodiment of the method, each point of equilibrium in a non-homogeneous array of elements can be dedicated to containing a particle or a group of particles (we shall call said elements "parking cells") or else to the transport of particles in pre-set directions (we shall call said elements "lanes" or "conveyors"). According to the present invention each path can be broken down into the succession of elementary steps constituted by the entrance to, or exit from, a pre-set region of transport, thus allowing each particle to be guided from the initial position to any final destination.

In a further embodiment of the method, the points of equilibrium are constrained, in groups, to moving in a synchronous way, along certain lanes. Points of exchange between the groups enable the particles to pass from one group to another, i.e., to change lane. Notwithstanding these additional constraints, the method in any case enables carrying-out of manipulations of individual particles, and, after a series of steps, displacement of a single particle, leaving the position of all the others unaltered.

The object of the present invention is moreover a device that advantageously makes available some of the aforesaid methods, constituted by an array of electrodes, applied to which are time-variant potentials, with or without transistors or memory elements.

The object of the present invention is also a family of apparatuses for identification and/or quantification and/or characterization of particles by means of impedance meter and/or optical sensors. The combination of sensors and actuators is particularly useful for automation of complex operations but proves in any case advantageous for positioning the particles to be individuated exactly in the regions of greater sensitivity for the sensors (which may be integrated but also external), thus considerably improving the sensitivity of the measurement.

DESCRIPTION OF THE INVENTION

In what follows the term "particles" will be used to indicate micrometric or nanometric entities, either natural ones or artificial ones, such as cells, subcellular components, viruses, liposomes, niosomes, microspheres, and nanospheres, or even smaller entities, such as macro-molecules, proteins, DNA, RNA, etc., as well as drops of liquid immiscible with the suspension medium, for example oil in water, or water in oil, or even drops of liquid in gas (such as water in air) or bubbles of gas in liquid (such as air in water).

DETAILED DESCRIPTION

The aim of the present invention is the implementation of a method and an apparatus for the manipulation and/or detection of particles. By "manipulation" is meant, in particular, one of the following operations and/or combinations thereof:

1. selection, which consists in the isolation of a given particle from a sample containing a multiplicity of particles;
2. reordering, which consists in the arrangement of the particles in an order different from the starting one;
3. union, which consists in selecting two or more particles and in bringing them closer together until they are forced against one another, for the purpose of bringing them into contact or of merging them or of including them one within the other;
4. separation, which consists in separating particles that initially were in contact with one another.

The method is based upon the use of a non-uniform field of force (F) through which to attract individual particles or groups of particles towards positions of stable equilibrium (CAGE). Said field can, for example, be a dielectrophoresis field (DEP), either negative dielectrophoresis (NDEP) or positive dielectrophoresis (PDEP) field, an electrophoretic field (EF) or else a field of electrohydrodynamic (EHD) motion, or else again electro-wetting on dielectric (EWOD).

The detection can regard one of the following aspects or a combination thereof:

1. count of individual particles or quantification;
2. identification and/or characterization;
3. location.

In this connection the measurement of the variation of impedance and/or the measurement of the variation of light intensity/absorbance is principally exploited.

Generation of Forces

Figure 1:
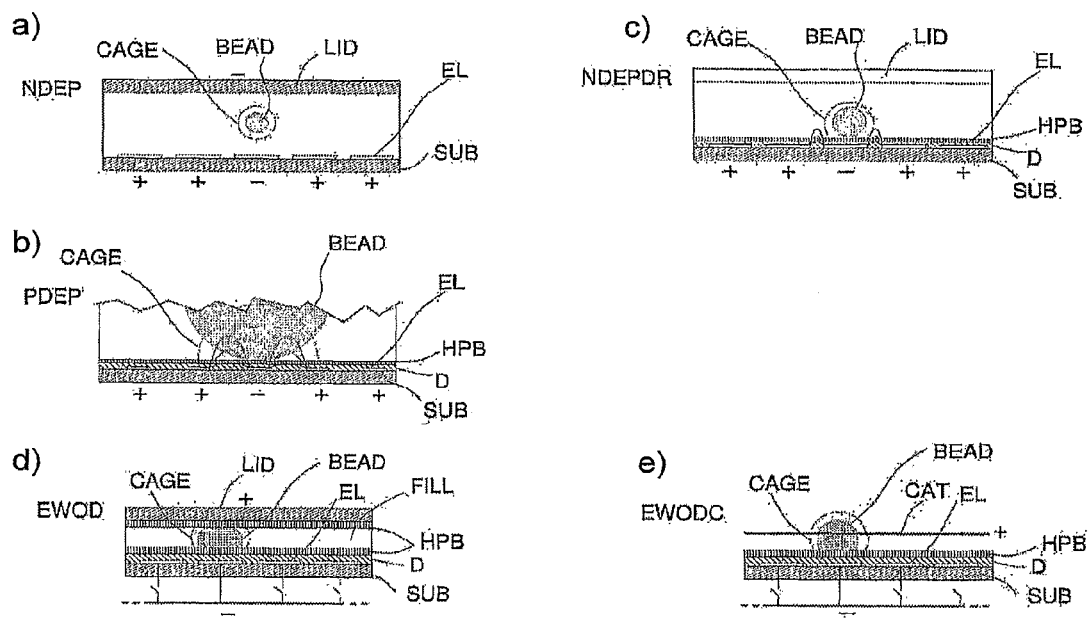
FIG. 1 shows the principle of generation of fields of force by means of arrays of electrodes.

There exist different methods for the generation of forces for displacing particles, according to the known art, by means of arrays of electrodes (EL) made on a substrate. Typically a cover (LID) is used, which can, in turn, be an electrode, which delimits a microchamber, within which the particles (BEAD) are typically in liquid suspension. Some schemes for the various forces are shown in FIG. 1. In the case of DEP, the voltages applied are in-phase periodic voltages (Vphip) indicated with the symbol of addition (+) and phase-opposition periodic voltages (Vphin) designated by the symbol of subtraction (−). By "phase-opposition voltages" are meant voltages that are 180° out of phase. The field generates a force that acts on the particles, attracted towards points of equilibrium (CAGE). In the case of negative DEP (NDEP), it is possible to obtain closed cages of force, according to the known art (FIG. 1a), if the cover (LID) is a conductive electrode. In this case, the point of equilibrium (CAGE) is obtained at each electrode connected to Vphin (−) if the adjacent electrodes are connected to the opposite phase Vphip (+) and if the cover (LID) is connected to the phase Vphin (−). Said point of equilibrium (CAGE) is normally set in the liquid at a distance from the electrodes, so that the particles (BEAD) are, in the steady-state condition, in levitation. In the case of positive DEP (PDEP), the point of equilibrium (CAGE) is located normally at the surface on which the electrodes are formed (FIG. 1b), and the particles (BEAD) are, in the steady-state condition, in contact therewith. For PDEP it is not necessary to have further electrodes in the cover, because the points of equilibrium of the PDEP correspond to the maxima of the electrical field. To manipulate particles formed by droplets of liquid immiscible in the suspension medium and heavier than this (for example, water in oil), the negative dielectrophoresis (NDEPDR) can be advantageously used (FIG. 1c) obtained by means of a substrate (SUB) with electrodes (EL), coated by a dielectric layer (D) and by a hydrophobic layer (HPB). An array of electrodes can be used for electrophoresis, to attract charged particles towards the electrodes with opposite polarity. For the EHD motions, the configurations of electrodes generate flows that push the particles towards points of minimum of the flow. For EWOD (FIG. 1d), a cover (LID) containing an electrode coated with dielectric is in general used, and the array of electrodes is energized by signals in phase opposition with respect to the cover in the points in which it is desired to attract the particles (typically droplets of liquid in air). The electrodes on which the particle must not be present are, instead, left floating. For EWOD, when manipulating droplets in air, on top of the array of electrodes it is also possible to use a series of wires (FIG. 1e) as an alternative to the cover.

In order to describe the methods and apparatuses, for reasons of simplicity, in what follows use of closed cages using NDEP as force of actuation is considered purely by way of example in no way limiting the scope of the present invention (hence it is necessary to use a covering lid that will function as electrode). It is evident to persons with ordinary skill in the sector how it is possible to generalize the methods and apparatuses described hereinafter for the use of different forces of actuation and different types of particles.

Figure 2:
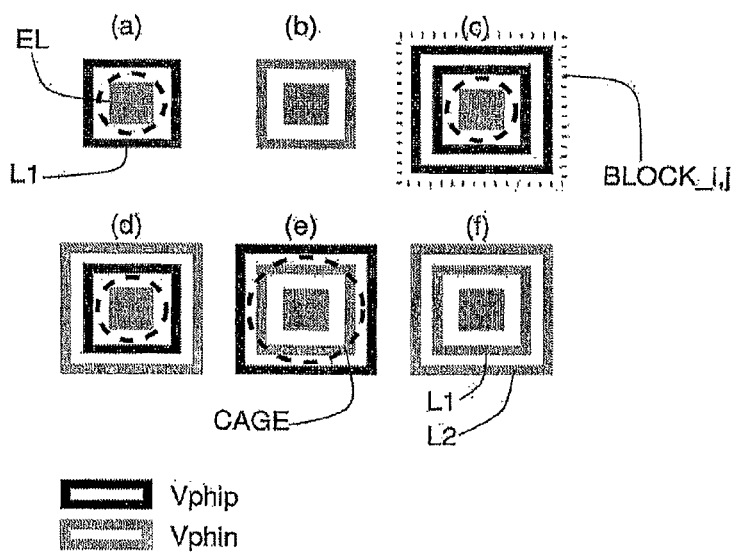
FIG. 2 shows the combination of the effects due to energization of addressable electrodes.

Generation of Control on the Movement of the Particles by Means of the Logic Combination of the Effects of Force Activated by Means of Rows and Columns In order to generate a point of stable equilibrium for the force of negative dielectrophoresis, it is sufficient, according to the known art, to have available a first electrode (EL) to be supplied by means of a signal (Vphin) in phase with the cover (LID) and one or more electrodes (L1) that surround completely the first electrode, supplied by means of a signal in phase opposition (Vphip). This configuration (illustrated in FIG. 2a) generates a minimum for the electrical field, corresponding to a point of stable equilibrium (CAGE) for the force of negative dielectrophoresis. Said point of equilibrium is lost if we reverse the phase of the signal applied to this first array of electrodes (L1), as illustrated in FIG. 2b. If we have available a second array of electrodes (L2), such that each electrode belonging to the second array (L2) surrounds one electrode belonging to the first array (L1), we shall obtain that the point of equilibrium is lost if we reverse the phase of both of the signals applied to the first array of electrodes (L1) and to the second array of electrodes (L2), as illustrated in FIG. 2f; in all the other cases, the cage may have a dimension and shape that depends upon the voltages applied. In particular, in FIG. 2c and FIG. 2d we have two identical cages whilst in FIG. 2e we have one cage of larger dimensions, but centred in the same position. As a consequence, if we consider a multiplicity of blocks (BLOCK_i,j) each made up of an electrode (EL) and one or more arrays of electrodes that surround it (L1, L2), we shall find that, according to the configuration of voltages applied to the electrodes L1 and L2 of two generic adjacent blocks, the following situations may arise:

a separate point of stable equilibrium for each block, the configuration of field of force of which we shall indicate with F_i;

just one point of stable equilibrium shared by the two blocks, the configuration of field of force of which we shall indicate with F_ii;

a separate point of stable equilibrium for each block, the configuration of field of force of which we shall indicate with F_i;

just one point of stable equilibrium shared by the two blocks, the configuration of field of force of which we shall indicate with F_ii;

This property can be exploited for implementation of some methods for the manipulation of particles according to the present invention with a series of important advantages as compared to the known art, as illustrated in what follows.

Figure 3:
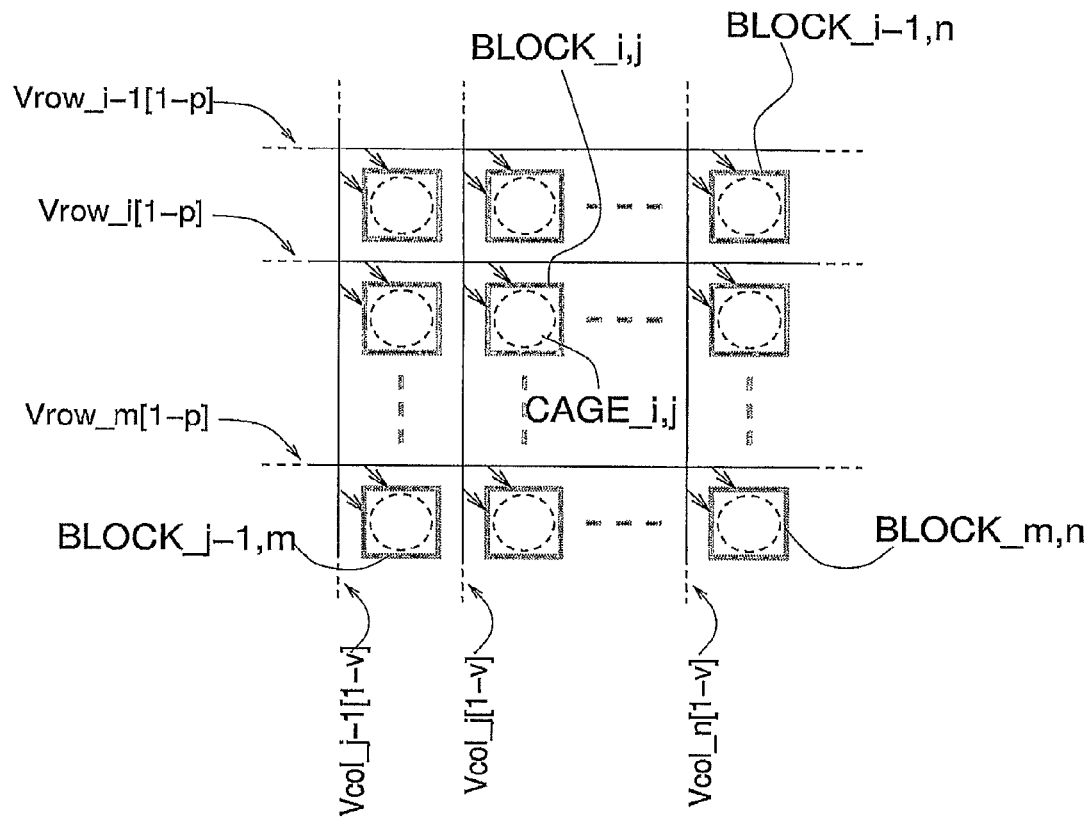
FIG. 3 shows an array of addressable elements for the creation of dielectrophoresis cages.

Method for the Manipulation of Particles on a Homogeneous Array without Transistors An embodiment of the method according to the present invention is illustrated in FIG. 3. A homogeneous array of generic groups (BLOCK_i,j) of electrodes provide an array of attraction cages defined by points of stable equilibrium (CAGE_i,j), each of which can entrap a single particle (BEAD) or group of particles. Each element (or block) of the array (BLOCK_i,j) is electrically connected to two groups of voltages (Vrow_i[p], Vcol_j[q], p=1 . . . u, q=1 . . . v) distributed in the array, respectively, in rows and columns and connected electrically to the blocks that share the same row or column. The total number of row signals is designated by u, whilst the total number of column signals is designated by v.

We shall define as distance between two blocks BLOCK_i,j and BLOCK_h,k the distance d=|i−h|+|j−k| in uniform—or Manhattan—norm, calculated on the indices of the blocks. We shall define as "adjacent blocks" blocks that are at a distance 1.

The same signals Vrow_i[p], Vcol_j[q] are used both for creation of the cages and for control of the position of the cages. Distributed through these signals are in fact the voltages necessary for the activation of the field of force of dielectrophoresis which have the following properties:

1. there always exists a configuration of potentials applied to the signals of the array such that each attraction cage is closed and distinct from all the others;

2. for each pair of adjacent blocks there always exists a configuration of potentials to be applied to the input signals to the pair such that it is possible to join only and exclusively the basins of attraction of the pair of blocks;

3. for each pair of adjacent blocks there always exists a sequence of potentials to be applied to the input signals to the pair such that, if just one of the two attraction cages is full, it is possible to displace the particle entrapped from one position to the adjacent one;

4. for each pair of adjacent blocks there always exists a sequence of potentials to be applied to the input signals to the pair such that, if both of the attraction cages are full, it is possible to displace both of the particles into the same position.

The voltages to be used are generally but not exclusively periodic waves (either sinusoidal waves or else square waves) with zero mean value, chosen between a set of voltages having a different phase; by way of non-limiting example, it is possible to use just two phases, which differ by 180° from one another.

It is evident that by joining two by two the centres of attraction of adjacent blocks it is possible to move a particle from a generic initial position to any final position or to bring into one and the same position two or more particles chosen from among all the particles present in the sample, without affecting the particles outside the path of the particles undergoing movement.

The same method can be applied to the generic case of the simultaneous manipulation of a number of particles with some restrictions. By way of non-limiting example, we give the restrictions for the simultaneous manipulation of just two particles entrapped in two different cages located in two generic blocks:

1. if a first block and a second block are not in the same row or column or in adjacent rows and columns, the particles entrapped in the two blocks can be manipulated simultaneously independently of the direction and sense, provided that there are no particles entrapped in the blocks corresponding or adjacent to the row of the first block and column of the second block or to the column of the first block and row of the second block;

2. if the two blocks are on the same column but are at a distance of at least three rows apart, they can be simultaneously manipulated in the vertical direction independently of the sense;

3. if the two blocks are on the same column but are at a distance of at least two rows apart, they can be simultaneously manipulated in the horizontal direction provided that the sense is the same.

4. if the two blocks are on the same row but are at a distance of at least three columns apart, they can be simultaneously manipulated in the horizontal direction independently of the sense;

5. if the two blocks are on the same row but are at a distance of at least two columns apart, they can be simultaneously manipulated in the vertical direction provided that the sense is the same.

It is evident that also more than two particles can be manipulated simultaneously, according to the present invention, respecting for each pair of particles the constraints listed above.

It should, however, be pointed out how, even though it is possible to manipulate independently two or more particles that satisfy the constraints referred to above, their simultaneous movement can have side effects on other cages of the array. For example, by manipulating simultaneously in a desired way a first particle at the block BLOCK_i,j and a second particle at the block BLOCK_h,k, an obligate movement is also imposed on the particles of the blocks BLOCK_h,j and BLOCK_i,k. To overcome this problem it is possible to act in different ways, depending upon the application, via various algorithms of sequencing and serialization of the displacements, and depending upon the knowledge or otherwise of the position of all the particles.

As example we give a case of particular interest: the recovery of a multiplicity of particles from a much larger heterogeneous population. In this case, a sample is injected with particles that set themselves randomly on the array. Said particles can be selected, for example, at the microscope, and, once the position of those of interest is determined, the problem is posed of sending them towards a gate (for example, communicating with a second recovery microchamber), from which they can be made to flow out of the chip. In this case, a simple and efficient solution, which does not require the knowledge of the position of all the particles but only of those to be selected, is the following (in the hypothesis that the gate is set on the right-hand side and at the bottom of the microchamber):

1. Vertical virtual channels are created (routing column) in the columns adjacent on the right to the position of each particle to be selected (selection column), freeing them from possible particles that are displaced onto the column further to the right (dump or waste column).

2. A horizontal virtual channel is created (routing row) at the gate of the recovery microchamber, freeing it from particles, as is done for the columns.

3. All the particles to be recovered on the routing column adjacent to each particle are displaced.

4. The column index of the particle to be recovered furthest from the routing row is inserted into a logic set shifting-cols.

5. The row index of the particle to be recovered furthest from the routing row is defined as shifting-row index.

6. The cages in the columns belonging to the set shifting-cols and to the row shifting-row are displaced down by a step, towards the routing row.

7. The index shifting-row is incremented.

8. If the new row shifting-row contains particles to be recovered, the column index of the new particle is inserted into the set shifting-cols.

9. If the new row shifting-row has an index lower than the one corresponding to the routing row, the procedure returns to step 6.

Or, alternatively, after step 3 the procedure is as follows:

4'. Starting from the row furthest from the routing row, the cages of all the routing columns are simultaneously displaced step by step down (i.e., towards the routing row), regardless of whether they contain particles or not. In this way, all the particles will be, at the end of scanning of the entire array (corresponding to a number of steps equal to the number of rows), transferred into the routing row.

At this point, all the particles to be selected are, in known column positions, on the routing row.

10. The entire routing row is shifted to the right, until all the particles have gone past the gate that communicates with the recovery microchamber.

11. The particles in the recovery microchamber are made to flow out of the chip.

Said method must be slightly complicated by preliminary operations in the case where the distance between columns of particles to be recovered is not always greater than 2, or in the case where there are, at the start of the procedure, particles on the routing row that have to be recovered. For reasons of simplicity, the description of said operations is omitted in so far as they are evident to a person with ordinary skill in the sector. Statistically, the need for carrying out these preliminary operations is more unlikely if the number of particles to be recovered is negligible with respect to the number of columns.

It should be noted that in general, by operating in parallel as described above, the number of steps to be taken for recovery of the particles is not significantly greater than the number of steps necessary with an array of totally programmable electrodes.

Apparatus for the Manipulation of Particles on a Homogeneous Array without Transistors The subject of the present invention is also an apparatus for obtaining the field configurations necessary for the manipulation of individual particles according to the method described previously. By way of non-limiting example, possible embodiments are provided, both based upon the use of a substrate without transistors and memory elements.

Apparatus for the Manipulation of Particles with n+m+2 Control Signals

Figure 4:
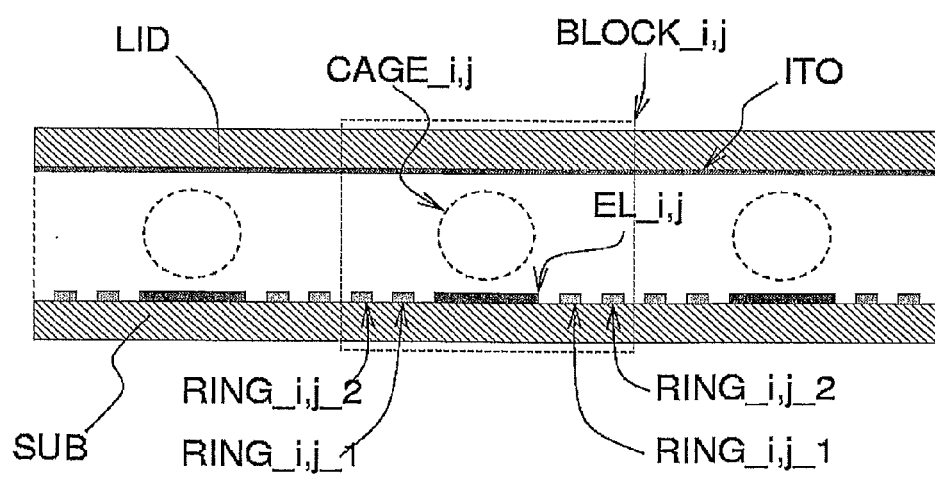
FIG. 4 shows the cross section of a device without transistors with addressable nested electrodes.
Figure 5:
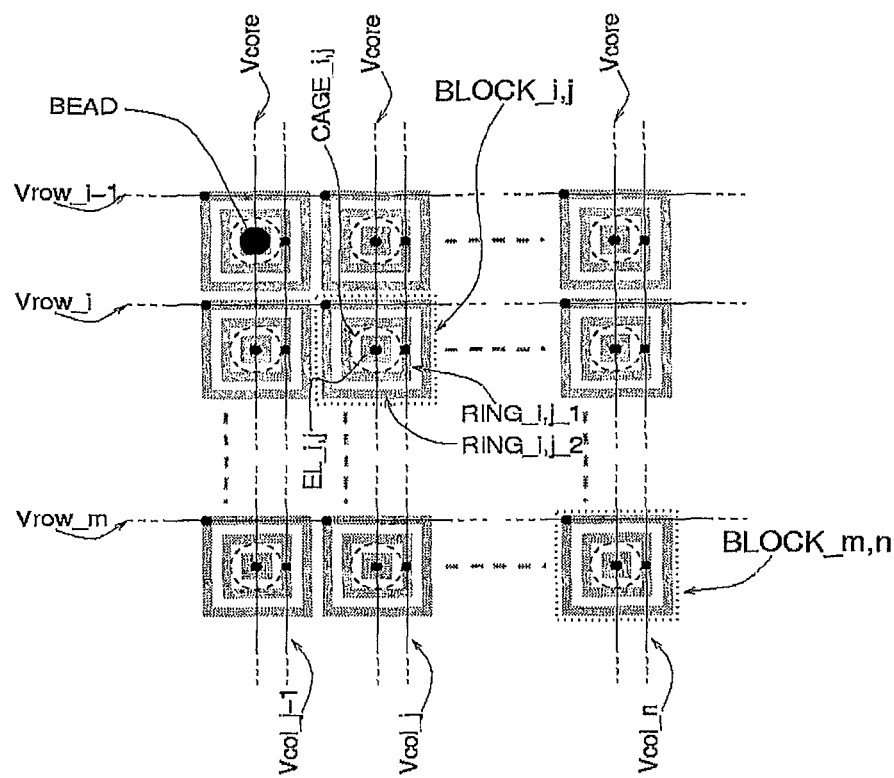
FIG. 5 shows a device for the implementation of the method of manipulation without transistors, based upon the combination of the effects associated to just two addressable electrodes.

FIGS. 4 and 5 are, respectively, a cross-sectional view and a top plan view of a first embodiment of the apparatus according to the present invention. A homogeneous array of groups (BLOCK_i,j) of electrodes forms an array of size n×m. Each block (BLOCK_i,j) is constituted by a central electrode (EL_i,j) connected to a signal common to the entire array (Vcore) and two concentric electrodes (ring_i,j_1, ring_i,j_2) connected to two different voltages (Vrow_i, Vcol_j) distributed in the array, respectively, in rows and columns as illustrated in FIG. 5. A further signal (Vlid) is connected to the cover (LID), constituted by a single electrode (ITO) (illustrated only in FIG. 4). The device consequently requires as a whole n+m+1+1 signals for control of n×m attraction cages, each of which can entrap a single particle (BEAD) or a group of particles. It is evident that a square array (n=m) minimizes the number of control signals with respect to the number of blocks constituting the n×m array.

Figure 7:
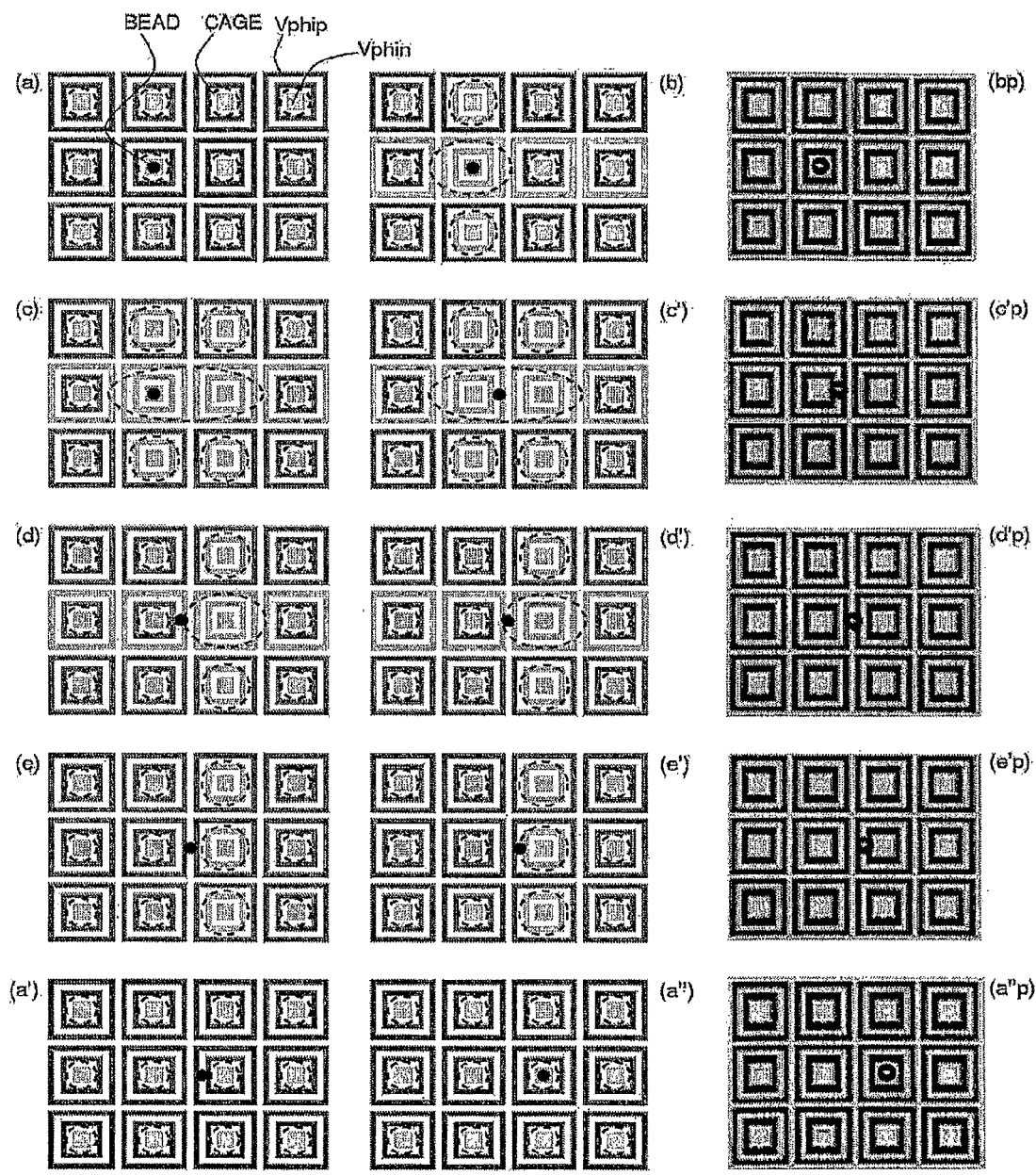
FIG. 7 shows the sequence of the elementary steps for displacement of a particle by one step to the right in a device without transistors with just two addressable electrodes and the experimental results.
Figure 10:
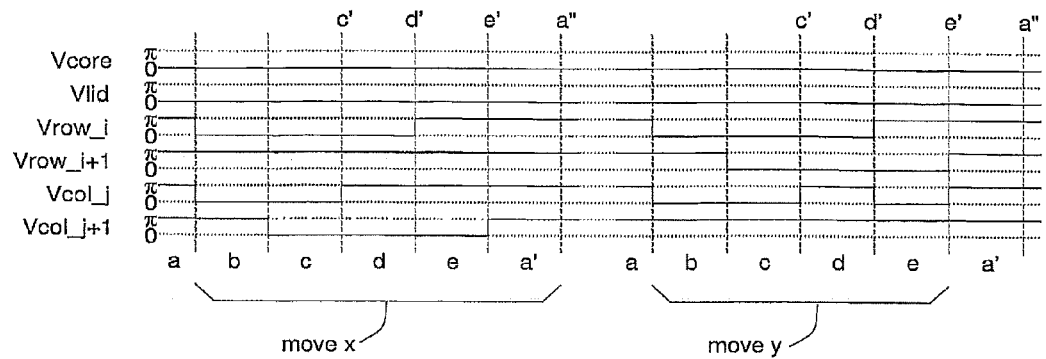
FIG. 10 shows the sequence of the phases of the voltages for performing the steps of manipulation to the right or down in a device with just two addressable electrodes.

By applying from outside a periodic voltage in phase (Vphip) to all the signals Vrow_i and Vcol_j and a periodic voltage in phase opposition (Vphin) to the common signal Vcore and the signal Vlid connected to the cover (LID), an attraction cage (CAGE_i,j) is activated in each block (BLOCK_i,j) separated and distinct from all the others in the array. The particle (BEAD) entrapped in a generic block (BLOCK_i,j) can be displaced towards any one of the adjacent cages by means of an appropriate sequence of voltages applied to the control signals. By way of example in no way limiting the scope of the invention, FIG. 7 shows the sequence of the steps (a, b, c, d, e) used to displace a particle from the generic block (BLOCK_i,j) into the adjacent block to the right (BLOCK_i,j+1); the voltages applied to the signals involved in the various steps that constitute said operation are indicated in FIG. 10 (sequence move_x), whilst the position of the particle in transient conditions after each step is indicated in FIG. 7 (b, c', d', e', a"). Illustrated in FIG. 7 (bp, cp', dp', ep', ap"), is the sequence of images of an experiment which correspond to the configurations (b, c', d', e', a") obtained via a prototype device.

Figure 8:
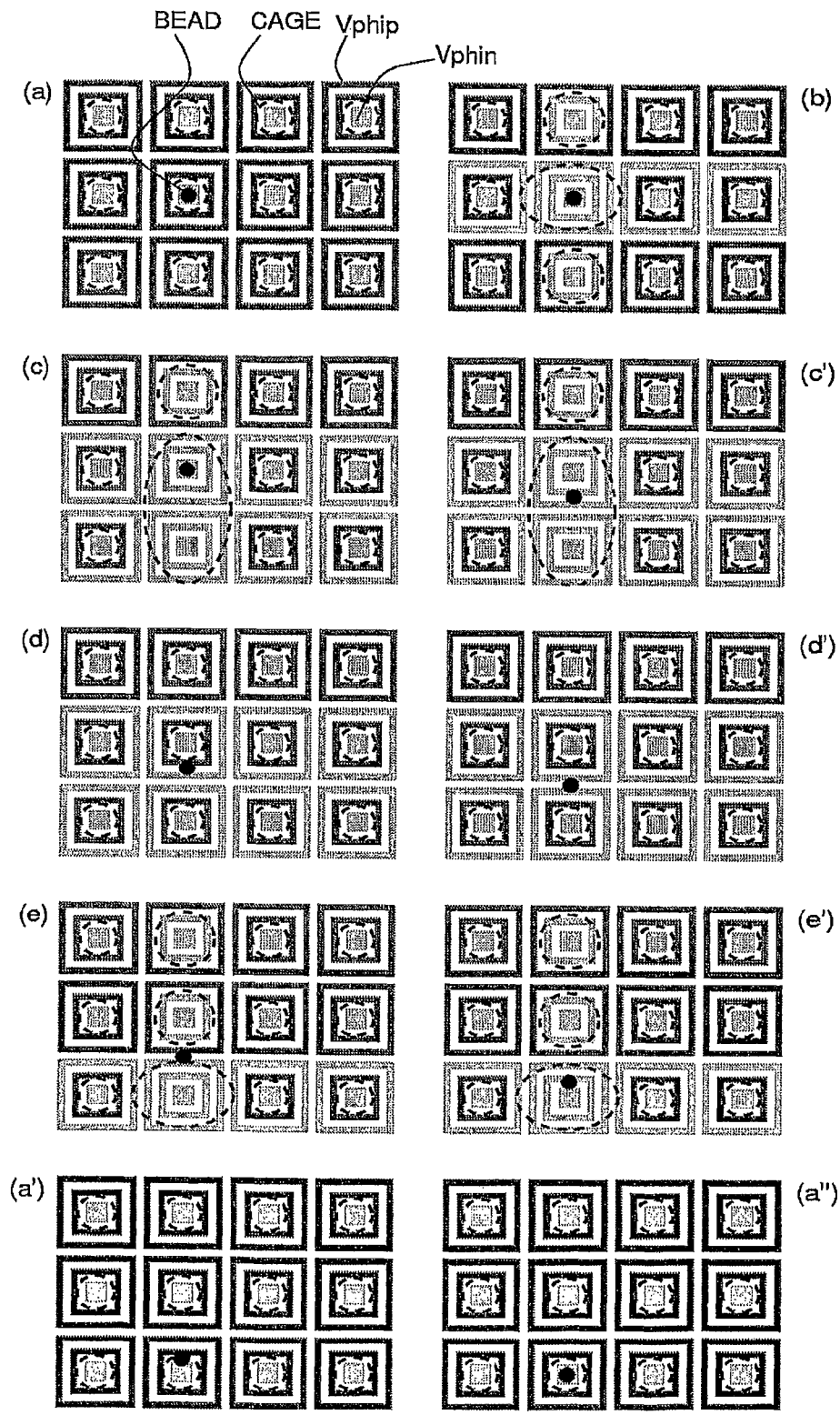
FIG. 8 shows the sequence of the elementary steps for the displacement of a particle by one step down in a device without transistors with just two addressable electrodes.

Likewise, FIG. 8 shows the sequence of displacement of a particle in the vertical direction, from the generic block (BLOCK_i,j) into the adjacent block downwards (BLOCK_i+1,j). The voltages applied to the signals involved in the various steps that constitute said operation are indicated in FIG. 10 (sequence move_y), whilst the position of the particle in steady-state conditions after each step is indicated in FIG. 8 (b, c', d', e', a"). In certain cases, it is possible to use a reduced sequence, constituted by a subset of the steps chosen from the sequences shown in FIG. 7 and FIG. 8. Optionally, for each of the possible directions, it is possible to use a sequence constituted by steps different from the ones described by way of non-limiting example in FIGS. 7 and 8.

Figure 9:
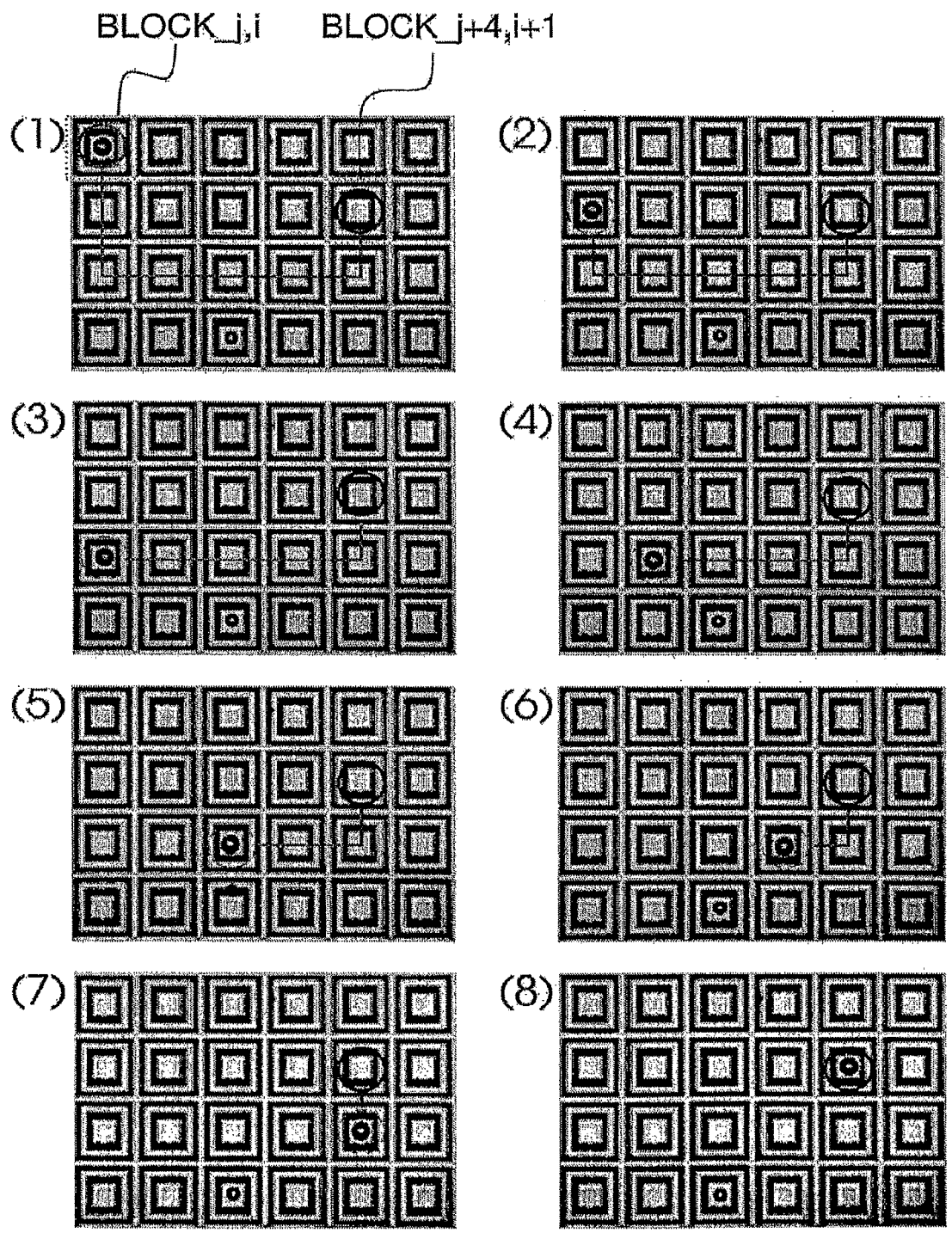
FIG. 9 shows the experimental results of the manipulation of a particle along a generic path in a device without transistors with just two addressable electrodes.

It is evident that any path that starts from a generic position in the array and terminates in any other position of the array can be broken down into the succession of the elementary steps illustrated in FIGS. 7 and 8 and in the analogous steps in the opposite direction. A practical example of said concept is illustrated in FIG. 9, which shows the succession of the elementary steps to displace a polystyrene microsphere from the initial position (BLOCK_i,j) towards the destination (BLOCK_i+1,j+4) following a generic path.

Figure 6:
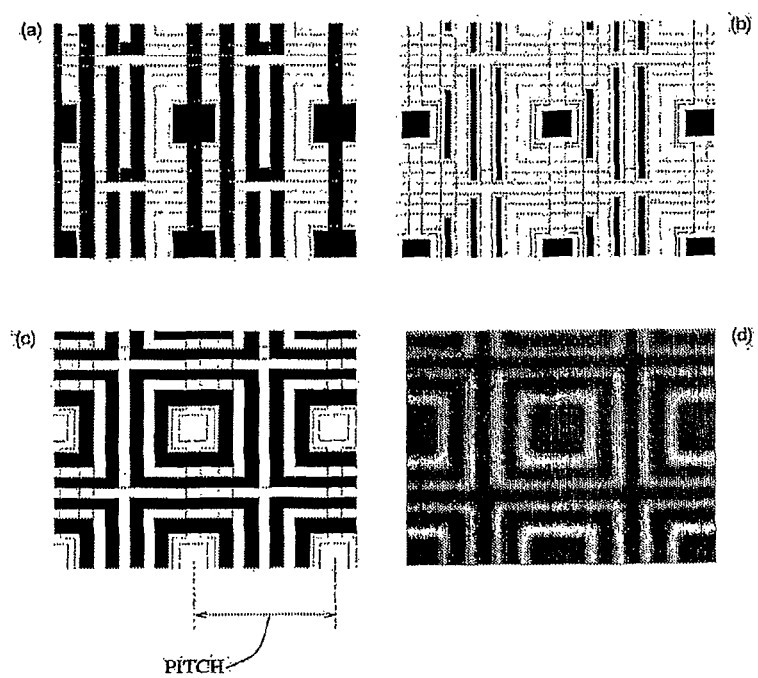
FIG. 6 shows a portion of the three masks necessary for the implementation of the prototype of apparatus with just two addressable electrodes and an image of the prototype.

Implementation of the apparatus according to the present invention can be obtained by exploiting different technologies according to the known art. Shown by way of example in no way limiting the scope of the present invention in FIG. 6a-c are the masks necessary for a possible embodiment of the apparatus by means of photolithographic techniques according to the known art and shown in FIG. 6d is an image of the prototype. Three masks and two metal levels are sufficient for the implementation. The minimum distance (PITCH) between the centres of two adjacent blocks is 5 times the pitch between surface metallizations. In this device the pitch (PITCH) is 100 µm; this means that the technology required for fabrication must enable the production of electrodes the minimum pitch of which is 20 µm. For production of the electrodes noble metals (gold, platinum, etc.) can be used, or else conductive oxides, which are particularly useful in the case where said oxides are transparent (Indium Tin Oxide—ITO). For the production of the substrate insulators (glass, polycarbonate, etc.) can be used, or else semiconductors (silicon, etc.), in which case a passivation oxide is required for insulating the substrate electrically from the first metal level. For the production of the cover (LID), an insulating substrate can be used provided that it is equipped with an electrode which also may be made with metals or conductive oxides, which are particularly useful in the case where said conductive oxides are partially or totally transparent. Likewise, semitransparency can be obtained using a non-transparent metal in the form of a grid.

It is evident to persons with ordinary skill in the sector, that other geometries different from the ones described in the present patent by way of example, can be used for the production of the apparatus according to the present invention. By way of non-limiting example, we may cite electrodes with circular, hexagonal, rectangular geometries, etc. Likewise, it is evident that other materials, different from the ones referred to in the present patent, can be used for the production of the apparatus according to the present invention. By way of non-limiting example we may cite materials such as aluminium, titanium, tantalum, gold, etc.

Apparatus for the Manipulation of Particles with 4n+4 m+2 Control Signals

Figure 11:
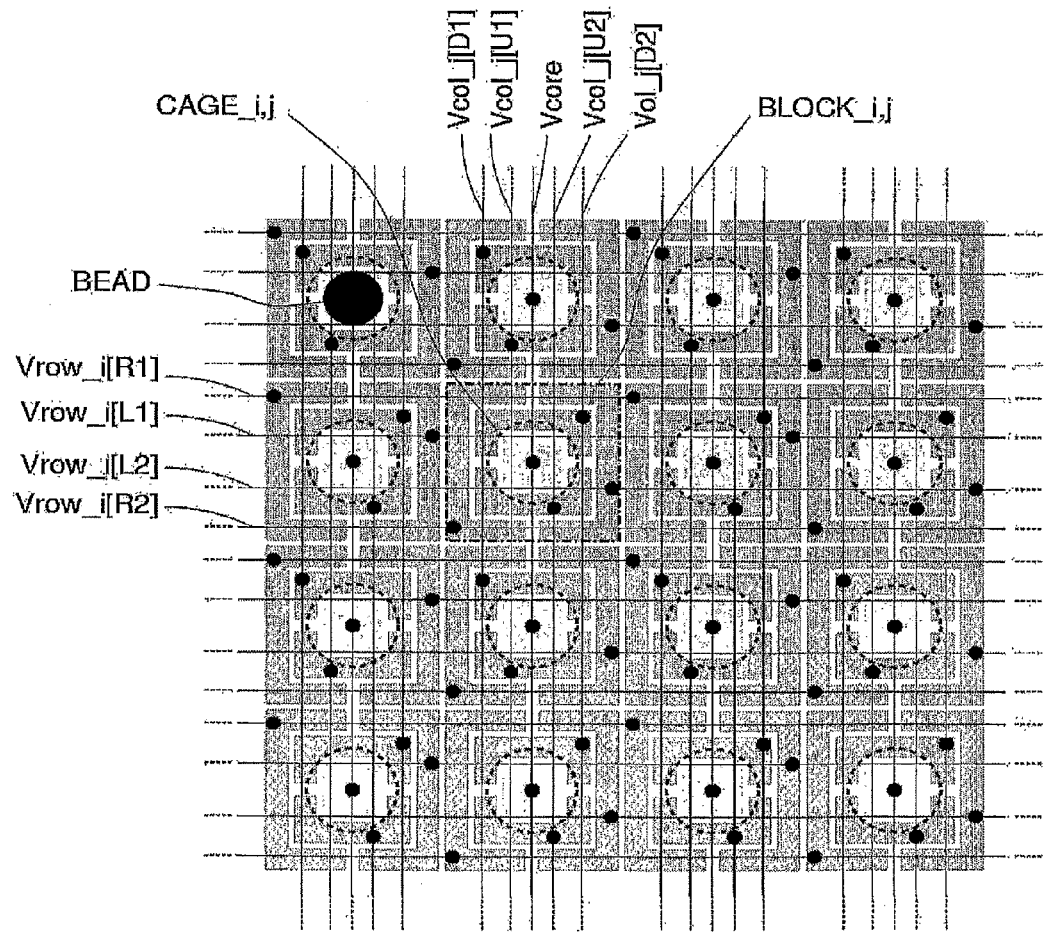
FIG. 11 shows a device for the implementation of the method of manipulation without transistors, based upon the combination of the effects associated to the energization of four addressable electrodes.
Figure 12:
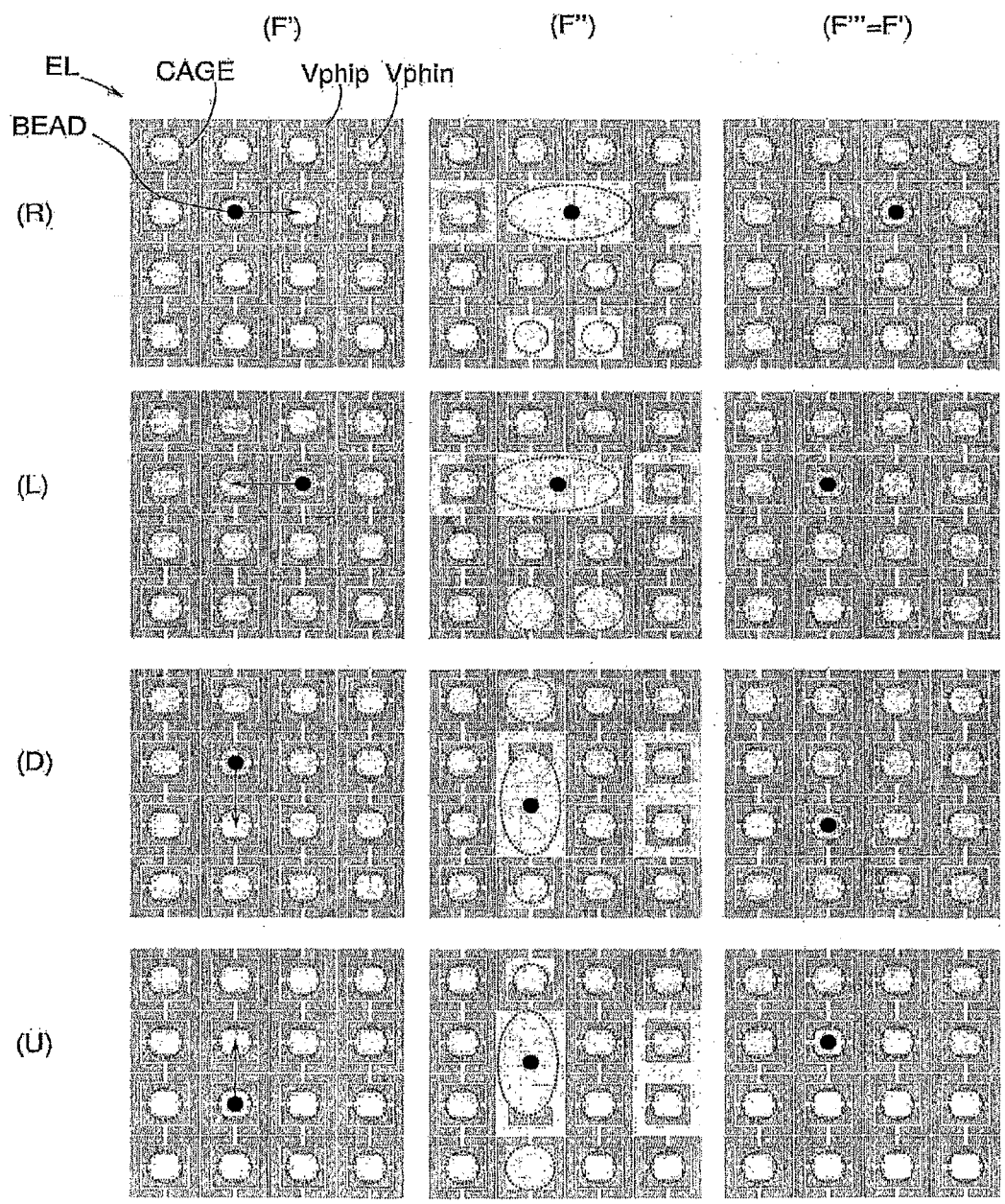
FIG. 12 shows the sequence of the elementary steps for displacement of a particle by one step to the right, down, to the right and to the left in a device without transistors with four addressable electrodes.

FIG. 11 is a top plan view of a different embodiment of the apparatus according to the present invention. In this case, four signals are used for each row and four signals for each column, plus a global signal Vcore common to all the blocks (distributed herein by column) and a signal Vlid. The external and internal ring electrodes of each block, are divided into two, vertically and horizontally, respectively. Alternately connected to the electrodes of each block are just two of the four row signals, and just two of the four column signals. The row signals and column signals are normally all connected to Vphip, and generate a field configuration (F_i), with an attraction cage (CAGE_i,j), for each block. By connecting to Vphin seven signals chosen appropriately from among the control signals by rows and columns, it is possible to generate a second configuration (F_ii), which joins the attraction cages of two adjacent blocks. As illustrated in FIG. 12 it is thus possible to displace a particle (BEAD) to the right (R), to the left (L), downwards (D) or upwards (U), without altering the position of the other particles possibly entrapped in nearby cages, simply by applying the field configuration (F_ii) and then the initial field configuration (F_i) again.

As compared to the embodiment with n+m phases, this embodiment presents the advantage of requiring only two field configurations for each elementary displacement, and the disadvantage of requiring a number of control signals four times greater.

Apparatus for the Manipulation of Particles with n+2 m+2 Control Signals

Figure 13:
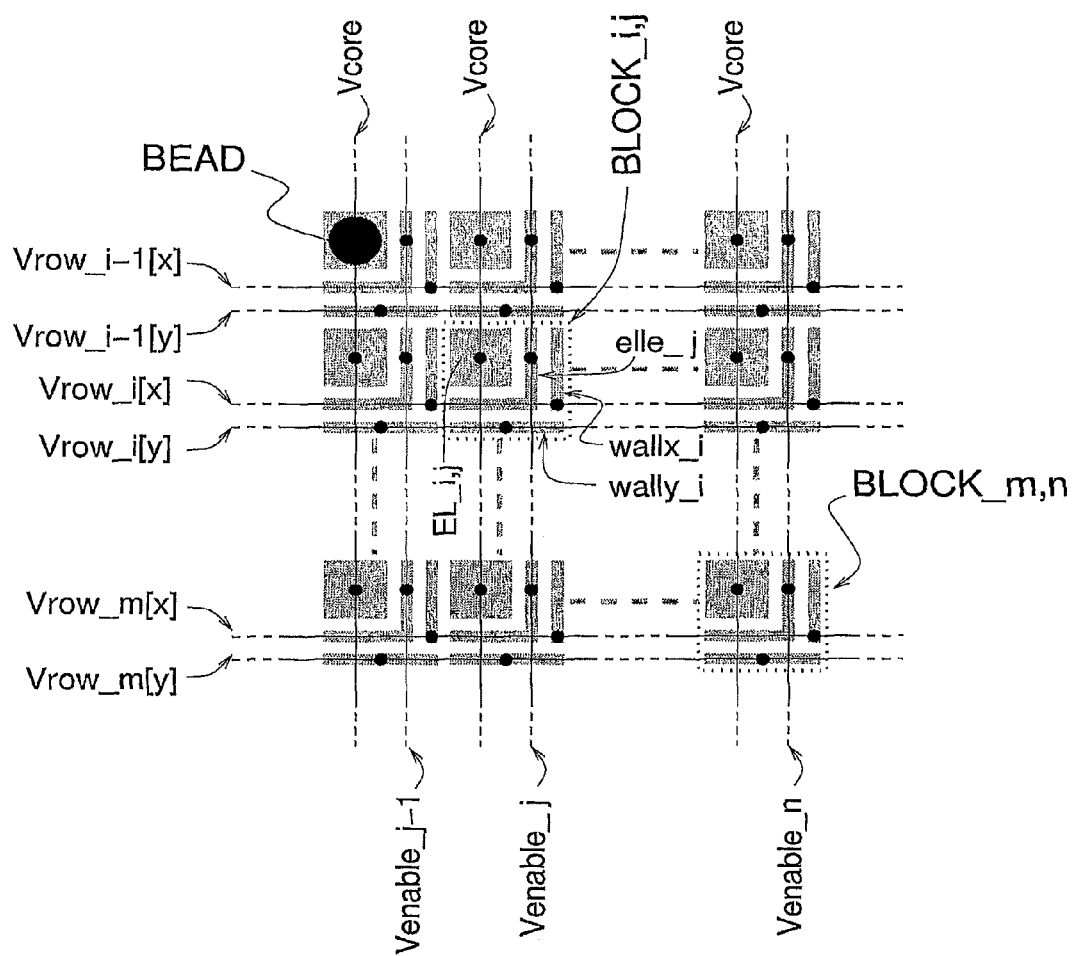
FIG. 13 shows a device for the implementation of the method of manipulation without transistors, based upon the combination of the effects associated to the energization of three addressable electrodes.

FIG. 13 is the top plan view of a further embodiment of the apparatus according to the present invention. A homogeneous array of blocks (BLOCK_i,j) forms an array of size n×m. Each block (BLOCK_i,j) is made up of: a central electrode (EL_i,j) connected to a signal common to the entire array (Vcore); an L-shaped electrode (elle_j) connected to signals distributed in the array according to columns (Venable_j); and two electrodes, one in the form of a vertical segment (wallx_i) and the other in the form of a horizontal segment (wally_i) connected to two different signals (Vrow_i[x], Vrow_i[y]) distributed in the array according to rows and arranged radially on the outside (with respect to the central electrode) of the electrode elle_j. A further signal (Vlid) is connected to the cover (LID), constituted by a single electrode (ITO). The device consequently requires as a whole n+2 m+1+1 signals for controlling n×m attraction cages, each cage being able to entrap a single particle (BEAD) or a group of particles. It is possible to show that a rectangular array where n=2m minimizes the number of control signals with respect to the number of blocks constituting the array (n×m).

Figure 14:
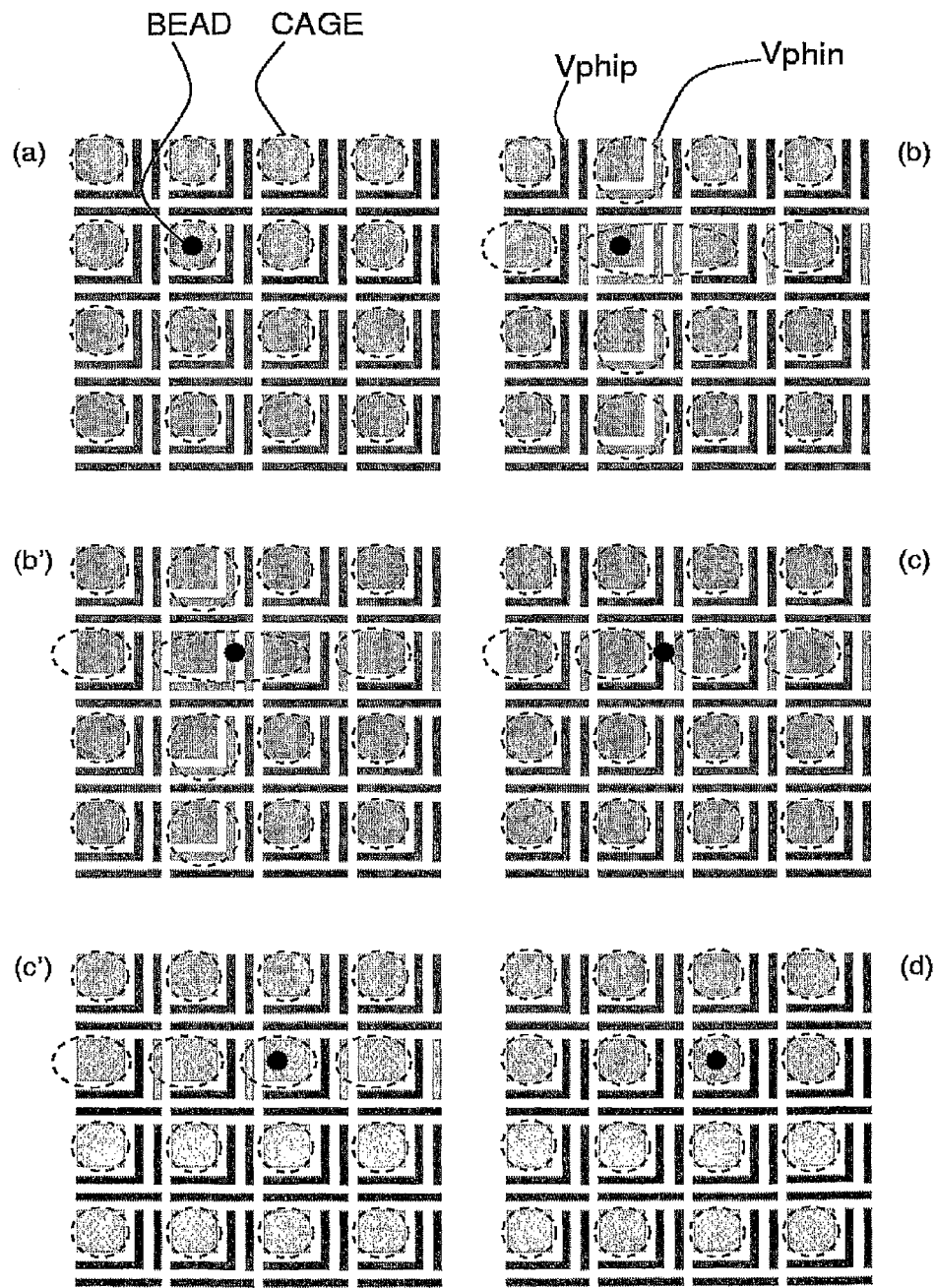
FIG. 14 shows the sequence of the elementary steps for the displacement of a particle by one step to the right in a device without transistors with three addressable electrodes.
Figure 15:
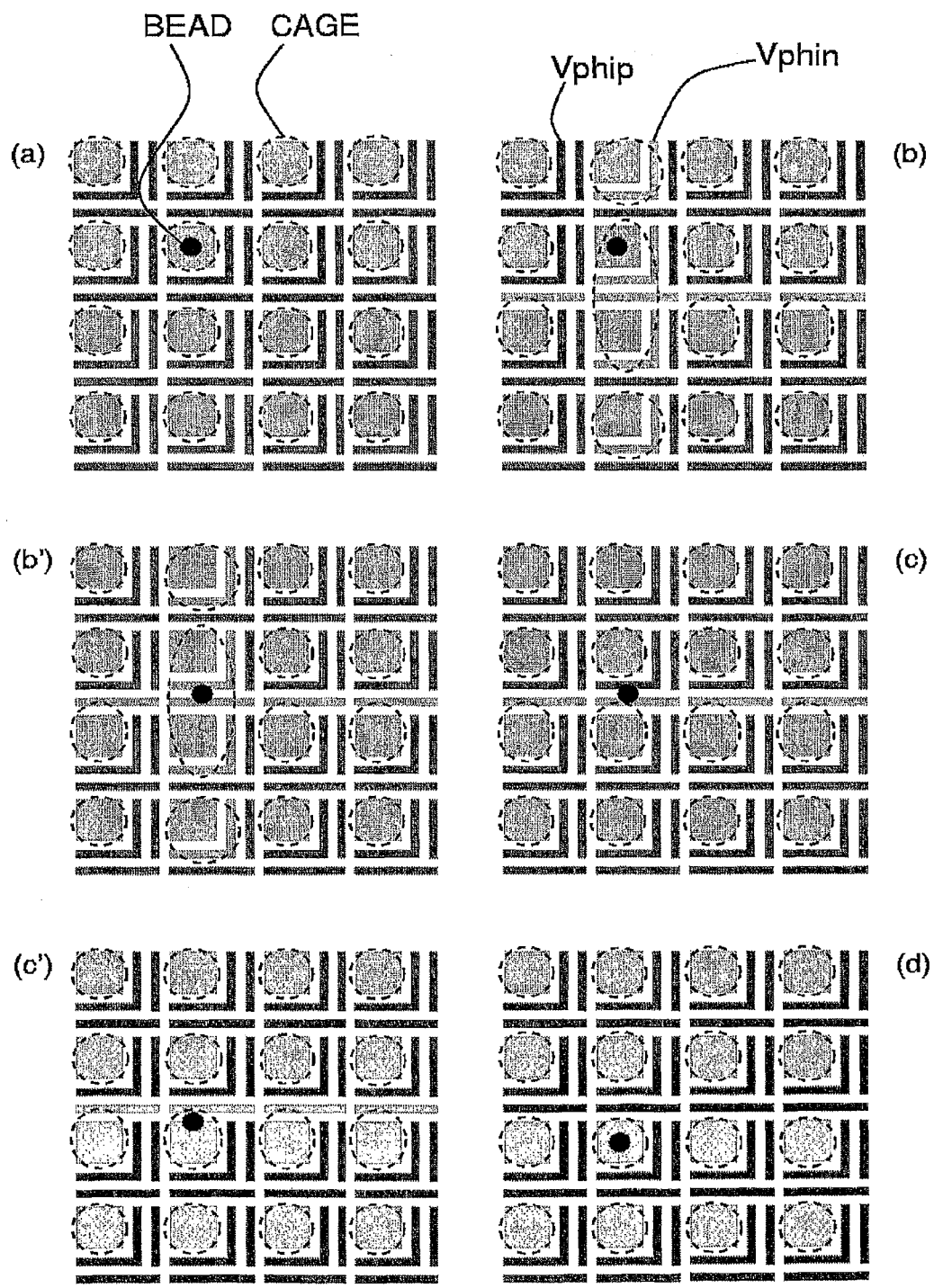
FIG. 15 shows the sequence of the elementary steps for the displacement of a particle by one step down in a device without transistors with three addressable electrodes.
Figure 16:
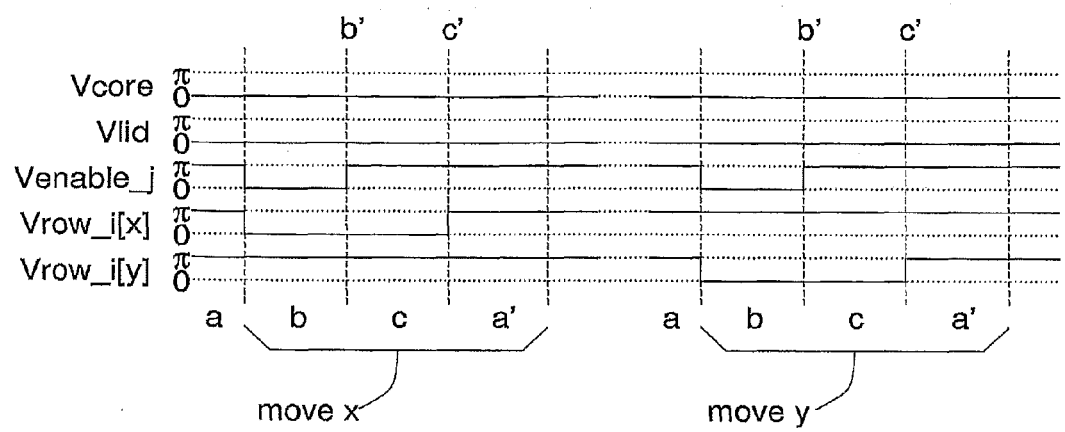
FIG. 16 shows the sequence of the phases of the voltages for carrying out the steps of manipulation to the right or down with three addressable electrodes.

By applying from outside a periodic voltage in phase (Vphip) to all the signals Vrow_i[x], Vrow_i[y] and Venable_j and a periodic voltage in phase opposition (Vphin) to the common signal Vcore and to the signal Vlid connected to the cover (LID), an attraction cage (CAGE_i,j) in each block (BLOCK_i,j) separate and distinct from all the others in the array is activated. The particle (BEAD) entrapped in each generic block (BLOCK_i,j) can be displaced towards any one of the adjacent cages by means of an appropriate sequence of voltages applied to the control signals. By way of example in no way limiting the scope of the invention, FIG. 14 shows the sequence of the steps (a, b, c, d) used to displace a particle from the generic block (BLOCK_i,j) into the adjacent block to the right (BLOCK_i,j+1); the voltages applied to the signals involved in the various steps of said operation are indicated in FIG. 16 (sequence move_x), whilst the position of the particle in transient conditions after each step is indicated in FIG. 14b', c'. Likewise, FIG. 15 shows the sequence of the steps (a, b, c, d) used to displace a particle from the generic block (BLOCK_i,j) into the adjacent block downwards (BLOCK_i+1,j). The voltages applied to the signals involved in the various steps that make up said operation are indicated in FIG. 16 (move_y), whilst the position of the particle in steady-state conditions after each step is indicated in FIG. 15b', c'. In certain cases, a reduced sequence can be used, made up of a subset of the steps chosen from the sequence illustrated in FIG. 14 and FIG. 15. Optionally, for each of the possible directions, a sequence can be used consisting of steps different from the ones shown by way of non-limiting example in FIG. 14 and FIG. 15.

It is evident that any path that starts from a generic position in the array and terminates in any other position of the array can be broken down into the succession of the elementary steps illustrated in FIG. 14 and in FIG. 15, and in the analogous steps in the opposite direction.

Figure 17:
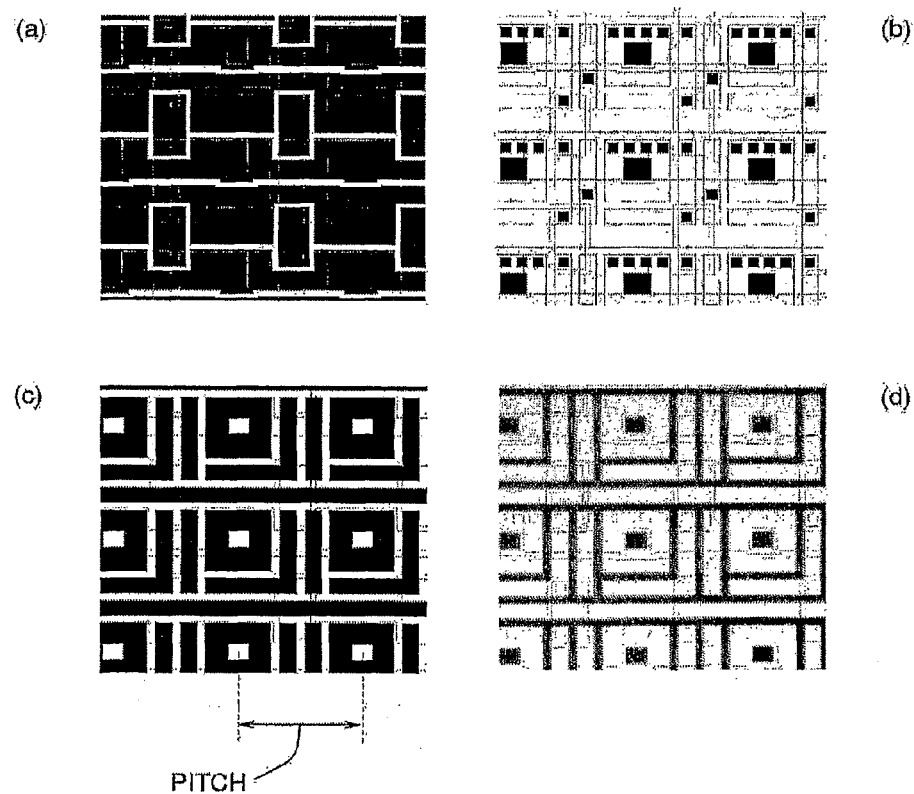
FIG. 17 shows a portion of the three masks necessary for the implementation of the prototype of apparatus with three addressable electrodes and an image of the prototype.

The implementation of the apparatus according to the present invention can be obtained exploiting different technologies according to the known art. By way of example in no way limiting the scope of the present invention, shown in FIG. 17 (a-c) are the masks necessary for a possible implementation of the apparatus by means of photolithographic techniques according to the known art, and shown in FIG. 17d is an image of the prototype. Three masks and two metal levels are sufficient for the implementation. The implementation of the apparatus according to the present invention can be obtained exploiting different technologies according to the known art. The pitch (PITCH), i.e., the distance between the centres of two adjacent blocks, in this device is 100 μm. For the electrodes, noble metals (gold, platinum, etc.) can be used or else conductive oxides, which are particularly useful in the case where said oxides are transparent (Indium Tin Oxide—ITO). For the substrate insulators (glass, polycarbonate, etc.) can be used or else semiconductors (silicon, etc.), in which case a passivation oxide is required for electrically insulating the substrate from the first metal level.

Method for the Manipulation of Particles on a Homogeneous Array without Memory Elements A further embodiment of the method according to the present invention uses an array of attraction cages (CAGE_i, j), in which each block (BLOCK_i,j) is electrically connected to two groups of signals (Vrow_i[p], Vcol_j[q]) distributed in the array, respectively, in rows and columns. Some of these signals are used for the distribution of the voltages (Vphin, Vphip) necessary for creation of the cages (CAGE), whilst others are digital signals used for control of the phase to be applied to the electrodes. In this case, the position of the points of static equilibrium (CAGE_i,j) is controlled by means of electronic circuits, which determine for each block whether the attraction cage is in isolation or connected to adjacent cages.

Apparatus for the Manipulation of Particles on a Homogeneous Array without Memory Elements The subject of the present invention is also an apparatus for the production of the field configurations necessary for the manipulation of individual particles according to the method described previously. By way of example, a possible embodiment is shown based upon the use of active substrates, in which, however, each block is without memory elements, unlike what is reported in the known art.

Figure 18:
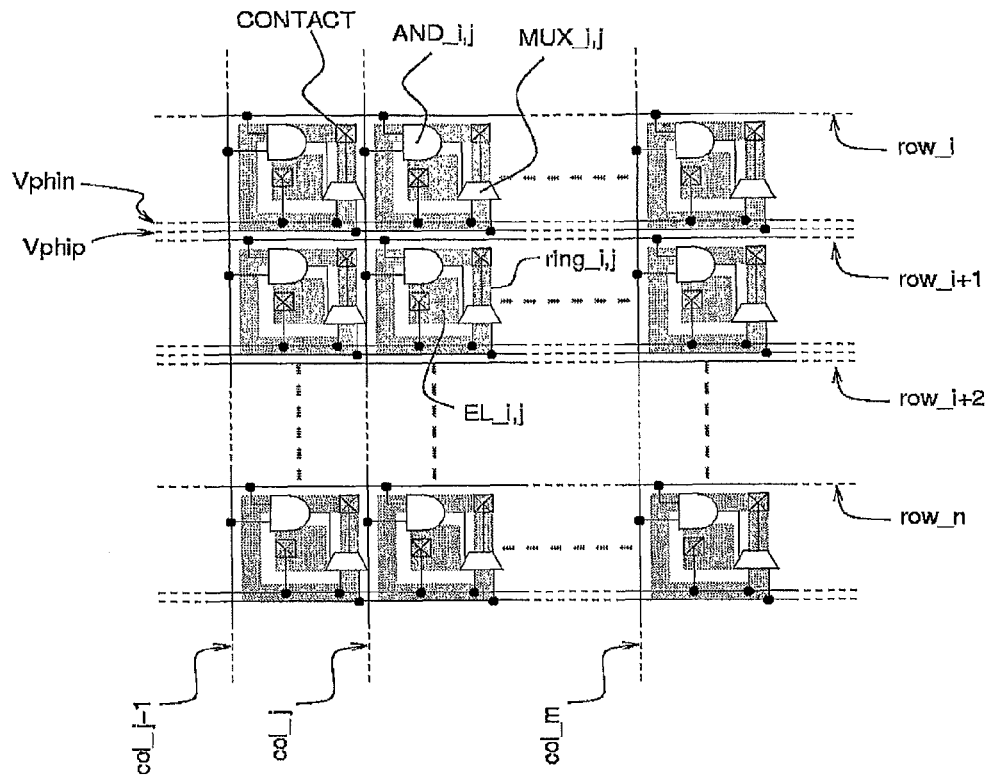
FIG. 18 shows a device for the implementation of the method of manipulation without memory elements, with just one addressable electrode.

FIG. 18 is a top plan view of a possible embodiment of the apparatus according to the present invention. A homogeneous array of blocks (BLOCK_i,j) forms an array of attraction cages of size n×m. Each block (BLOCK_i,j) is constituted by a central electrode (EL_i,j) connected to a signal common to the entire array (Vphin) and an electrode (ring_i,j) connected to the output of a multiplexer, which receives at input two different signals (Vphin, Vphip) and the output of which depends upon the logic combination of row digital control signals (row_i) and column digital control signals (col_j) according to the following table of logic values:

TABLE-US-00001

|  | row i = 0 | Row i = 1 |
| --- | --- | --- |
| col j = 0 | Vphip | Vphip |
| col j = 1 | Vphip | Vphip |

A further signal (Vlid) is connected to the cover (LID), not shown, constituted by a single electrode (ITO). The device consequently requires as a whole two analog signals (Vphin and Vphip) and n+m digital signals for controlling n×m attraction cages, each of which can entrap a single particle (BEAD) or a group of particles. It is evident that a square array (n=m) minimizes the number of control signals with respect to the number of blocks constituting the array (n×m).

Figure 19:
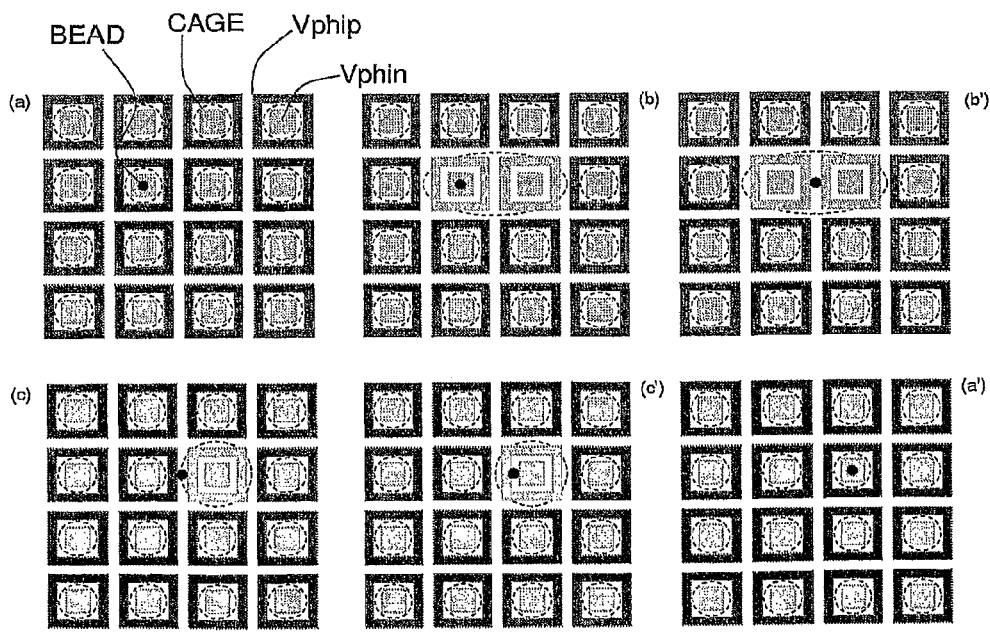
FIG. 19 shows the sequence of the elementary steps for the displacement of a particle by one step to the right without programming of memory elements, with just one addressable electrode.

By applying a logic value 0 to all the signals row_i and col_j and a periodic voltage in phase opposition (Vphin) with respect to the signal Vlid connected to the cover (LID), an attraction cage (CAGE_i,j) is activated in each block (BLOCK_i,j) separate and distinct from all the other in the array. The particle (BEAD) entrapped in each generic block (BLOCK_i,j) can be displaced towards any of the adjacent cages by means of an appropriate sequence of logic values applied to the control signals. By way of example in no way limiting the scope of the invention, FIG. 19 shows the sequence of the steps (a, b, c,) used to displace a particle from the generic block (BLOCK_i,j) into the adjacent block to the right (BLOCK_i,j+1); the sequence of the logic values applied to the signals row i, col j and col j+1 is the following:

TABLE-US-00002

|  | (a) | (b) | (c) | (a') |
| --- | --- | --- | --- | --- |
| col j | 0 | 1 | 0 | 0 |
| col j + 1 | 0 | 1 | 1 | 0 |
| Row i | 0 | 1 | 1 | 0 |

The position of the particle in transient conditions after each step is indicated in FIG. 19b', c', a'.

It is evident that the method applies in a similar way for any direction. In addition, any path that starts from a generic position in the array and terminates in any other position of the array can be broken down into the succession of the elementary steps constituted by displacements of just one position. The implementation of the apparatus according to the present invention can be obtained exploiting different technologies of fabrication of microelectronic circuits according to the known art.

Method for the Manipulation of Particles with Lanes and Parking Cells

Figure 20:
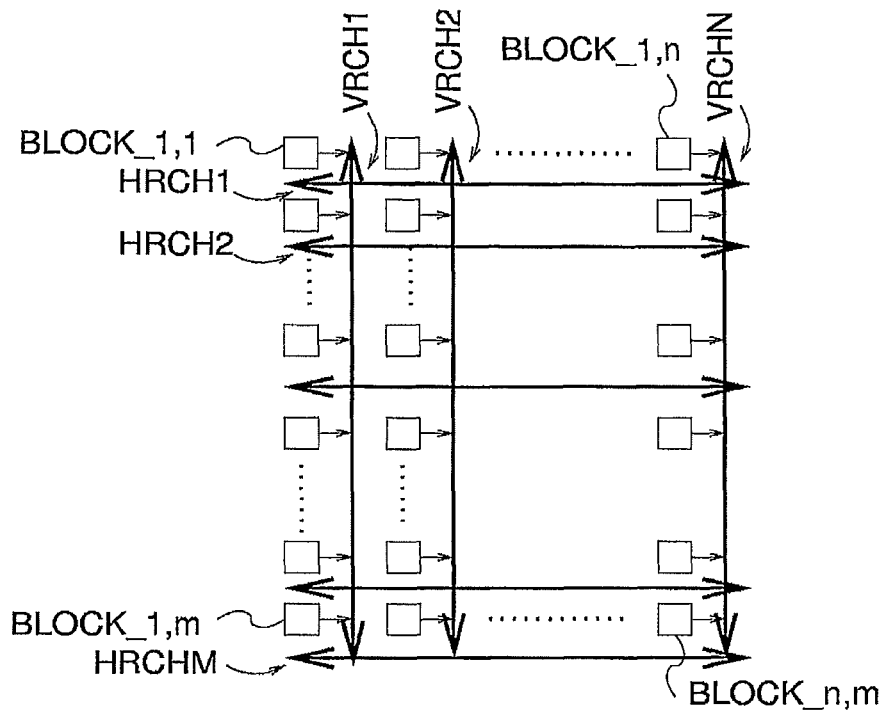
FIG. 20 shows an array of addressable elements for parking particles within dielectrophoresis cages and corridors for conveying said particles from one element to another of the array.
Figure 21:
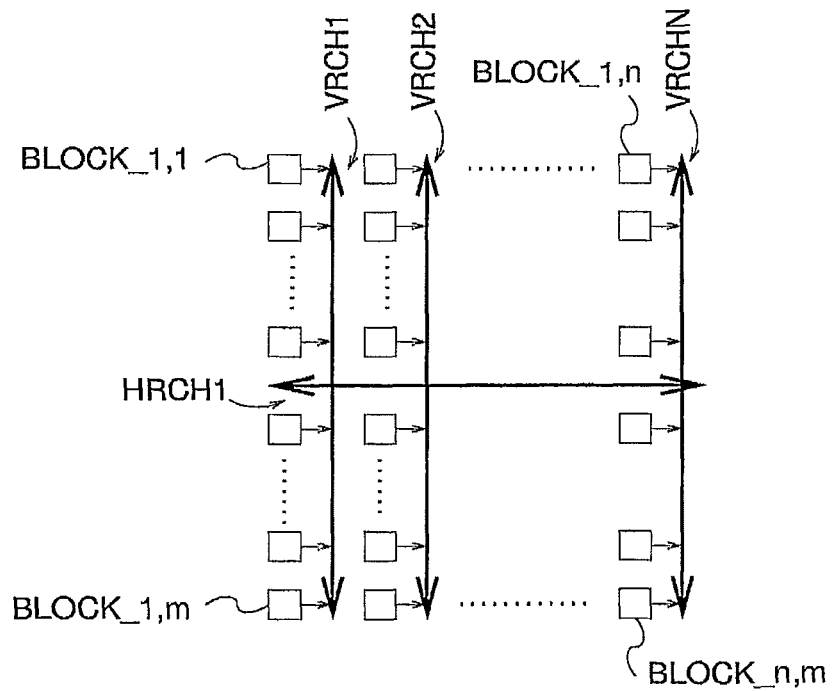
FIG. 21 shows an array of addressable elements for parking particles within dielectrophoresis cages and corridors, in a small number, for conveying said particles from one element to another of the array.
Figure 22:
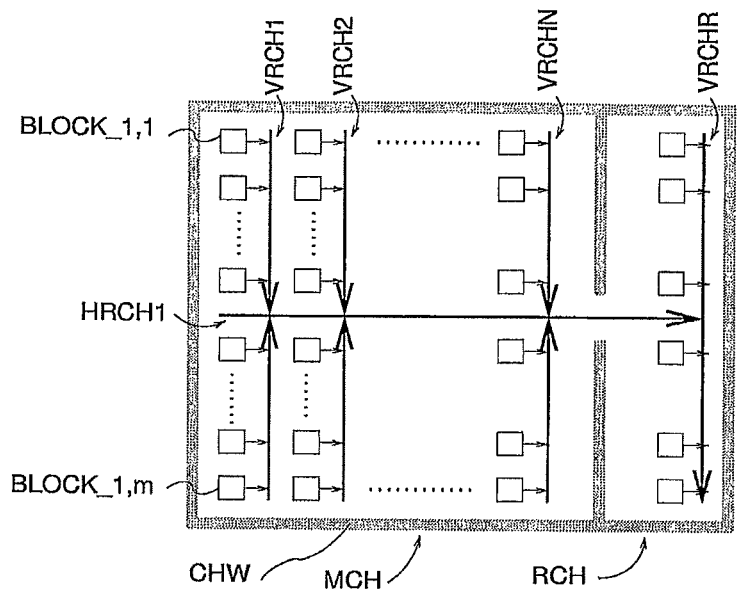
FIG. 22 shows a possible use of the method for selective transport of particles from a first microchamber to a second microchamber.

A further embodiment of the method according to the present invention is illustrated schematically in FIG. 20. The method uses a set of points of stable equilibrium that are static for the force (F) that acts on the particles, located within blocks (BLOCK_i,j), the function of which is that of entrapping stably a particle, and a set of points of stable equilibrium moving along lanes in the horizontal direction (HRCH1-HRCHM) or vertical direction (VRCH1-VRCHN). Each of these blocks (BLOCK_i,j) can be configured for entrapping the particle or pushing it within the basin of attraction of one of the points of stable equilibrium moving along the lanes. This can be obtained exploiting one of the methods described according to the present invention, for example joining the point of stable equilibrium of the block to one of the points of stable equilibrium of the lanes. It is evident that each of the particles present in the sample can consequently be parked within the blocks or else can be displaced from one block to any other one exploiting one or more lanes, in the most convenient direction. The particle can, in fact, enter a lane in motion and, likewise, the particle can exit from these lanes to enter a new block, or to change the direction of motion, passing onto a new lane. It is evident to persons with ordinary skill in the sector that each particle can pass from one block to any other one exploiting the method according to the present invention. The advantage of this technique consists in a reduction in the total number of signals dedicated to control of the entire array as is illustrated in the apparatuses described in what follows. Likewise, FIG. 21 shows a second embodiment of the method with a reduced number of horizontal paths. It is evident that also in this case each particle can pass from one block to any other one exploiting the single horizontal path (HRCH1). This technique enables a further reduction in the number of the signals required and increases the surface useful for providing cages. By way of example in no way limiting the scope of the present invention, FIG. 22 shows a possible application of the method. Present inside a microchamber (CHW) is an array of blocks (BLOCK_i,j) the function of which is the one described previously. The microchamber splits the array into two parts: one part (MCH) provided for containment of the sample to be processed, the other (RCH) provided for containment of the processed sample. For example, this scheme could be used for selecting just one particle retained in the first microchamber ((MCH) and recover it from the second microchamber (RCH). Each block (BLOCK_i,j) is functionally connected to a vertical corridor (VRCHJ), the direction and sense of movement of which is coherent within the entire array and terminates with a single horizontal corridor (HRCH1), the direction and sense of movement of which is chosen so that the particles conveyed can be transferred from the first microchamber (MCH) to the second microchamber (RCH) and then be accumulated in a single area through a final corridor (VRCHR). The selection of a particle from among the n×m retained initially in the first microchamber can be made, for example, by transferring it onto the corresponding lane and conveying it into the second microchamber (RCH), initially free from particles, from which the particle selected can be extracted.

Apparatus for the Manipulation of Particles with Lanes and Parking Cells without Transistors The subject of the present invention is also an apparatus for the production of the field configurations necessary for the manipulation of particles according to the method described previously, based upon the use of parking blocks and lanes. By way of non-limiting example, a possible embodiment is shown based upon the use of passive substrates, in which each block is without any memory elements or transistors.

Figure 23:
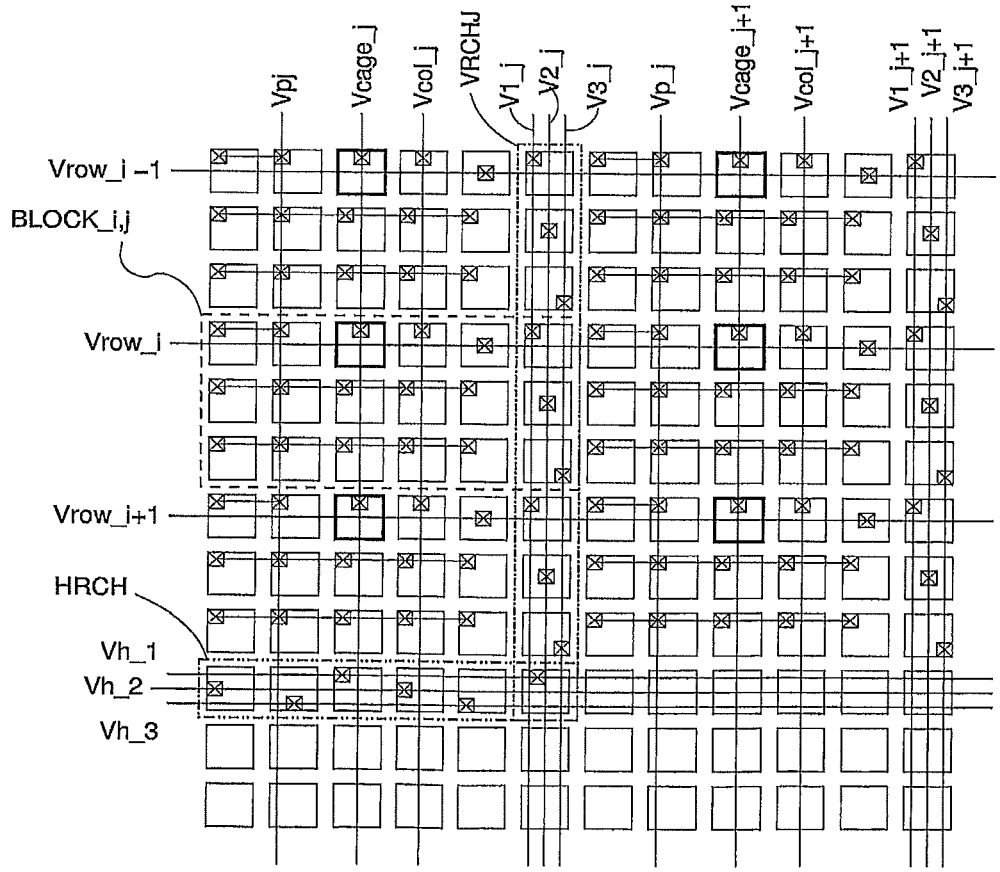
FIG. 23 shows a first apparatus for the implementation of the method of manipulation without transistors, with corridors and parking cells.
Figure 25:
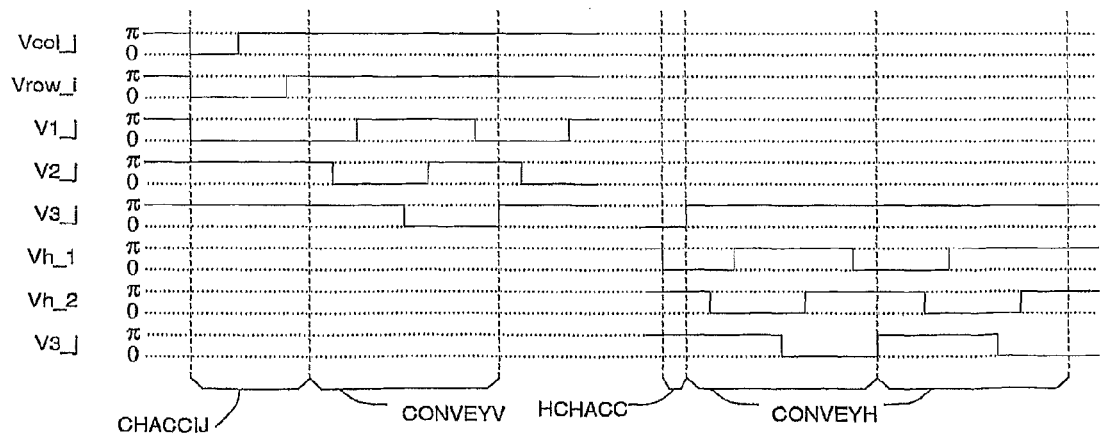
FIG. 25 shows the sequence of the phases of the voltages for carrying out the fundamental steps of the operation of the apparatus with corridors and parking cells.

FIG. 23 is a top plan view of a first embodiment of the apparatus according to the present invention. A homogeneous array of blocks (BLOCK_i,j) forms an array of attraction cages capable of entrapping a particle stably. Each block (BLOCK_i,j) is made up of: a central electrode, connected to a control signal (Vcage_j) common to all the blocks of the same column (or even to the entire array); a set of electrodes connected to a signal (Vpj) common to the entire array, and corresponding to Vphip; an electrode connected to a control signal (Vcol_j) common to all the blocks of the same column; and, finally, an electrode connected to a control signal (Vrow_i) common to all the blocks of the same row. By acting on the phase applied to the signals Vcage_j, Vcol_j and Vrow_i, the point of stable equilibrium for the force that entraps the particle can be displaced from the block (BLOCK_i,j) towards a corridor (VRCHJ) or from the corridor towards the block. Each corridor is made up of an array of electrodes connected to signals common to the entire corridor (V1_j, V2_j and V3_j). By acting on the phase applied to these signals it is possible to create and to displace as desired points of stable equilibrium for the force F along the entire corridor. Likewise, the apparatus can have available one or more corridors oriented in a horizontal direction (HRCH), controlled by three signals common to the entire corridor (Vh_1, Vh_2 and Vh_3), operation of which is altogether similar to that of the corridors oriented vertically (VRCHJ). FIG. 25 shows the voltages applied to the signals involved in the various steps that constitute the sequence for exit from a block (CHACCIJ), for shifting by a position along the vertical corridor (CONVEYV), for entry into the horizontal corridor (HCHACC), and for running along the horizontal corridor (CONVEYH). It is evident that in order to reverse the sense of travel along the horizontal corridor or vertical corridor it is sufficient to reverse the sequence of the phases with respect to that illustrated in FIG. 25.

Figure 24:
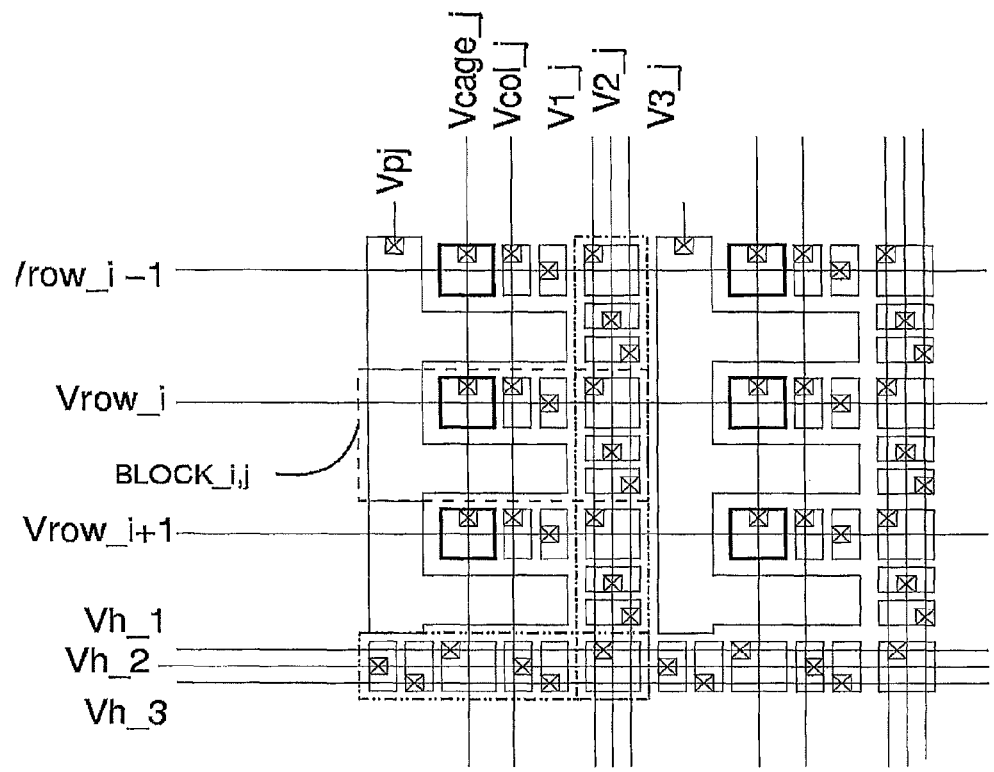
FIG. 24 shows a second apparatus for the implementation of the method of manipulation without transistors, with corridors and parking cells.

FIG. 24 shows the top plan view of a further embodiment of the apparatus for the manipulation with lanes and parking cells according to the present invention. Operation is altogether similar to that of the embodiment described previously, but enables a greater density of attraction cages to be obtained per unit surface in so far as, for each column of blocks BLOCK_ij, the n electrodes at potential Vpj are replaced by a single comb-shaped electrode at potential Vpj.

The number of control signals for both of the implementations without transistors of the apparatus with lanes and parking cells, for an array of n×m blocks with a number of independent horizontal and vertical corridors equal to g and f respectively, is 2n+m+3(g+f)+2. If the signal Vcage_j is shared among all the columns, the number of signals drops to n+m+3(f+g)+2. Typically (as illustrated in the examples), f=m, but it is possible also to share the same vertical lane between two columns of cages, in which case f=m/2. The number of horizontal channels can be chosen as desired. The greater the number of horizontal channels, the greater the flexibility, but the smaller the useful area for the cages and the greater the number of control signals required.

In practice, in the example described above, the parking cells are logically organized in a two-dimensional (row, column) space, and each have access to a vertical lane when the signals of each of the dimensions (row and column) are activated, in the appropriate sequence. According to the present invention, it is also possible to achieve different compromises between the number of control signals and the surface necessary for the transfer of a cage from a parking cell to a lane, by logically organizing the aforesaid parking cells in a number of dimensions higher than two. In fact, the surface dedicated to the transfer from the parking cell to the lane is proportional to the number of logic dimensions (this area is to be considered wasted). The advantage is that the number of parking cells corresponds to the product of the number of control signals by each dimension. By way of example, 10,000 parking cells can require 100 rows and 100 columns, i.e., 200 control signals, in the case of two dimensions or else 22*3=66 control signals, in the case of three dimensions, or 10*4=40 control signals, for organization in four dimensions. The spatial arrangement of the parking cells, can remain obviously two-dimensional, whatever the logic organization.

Figure 49:
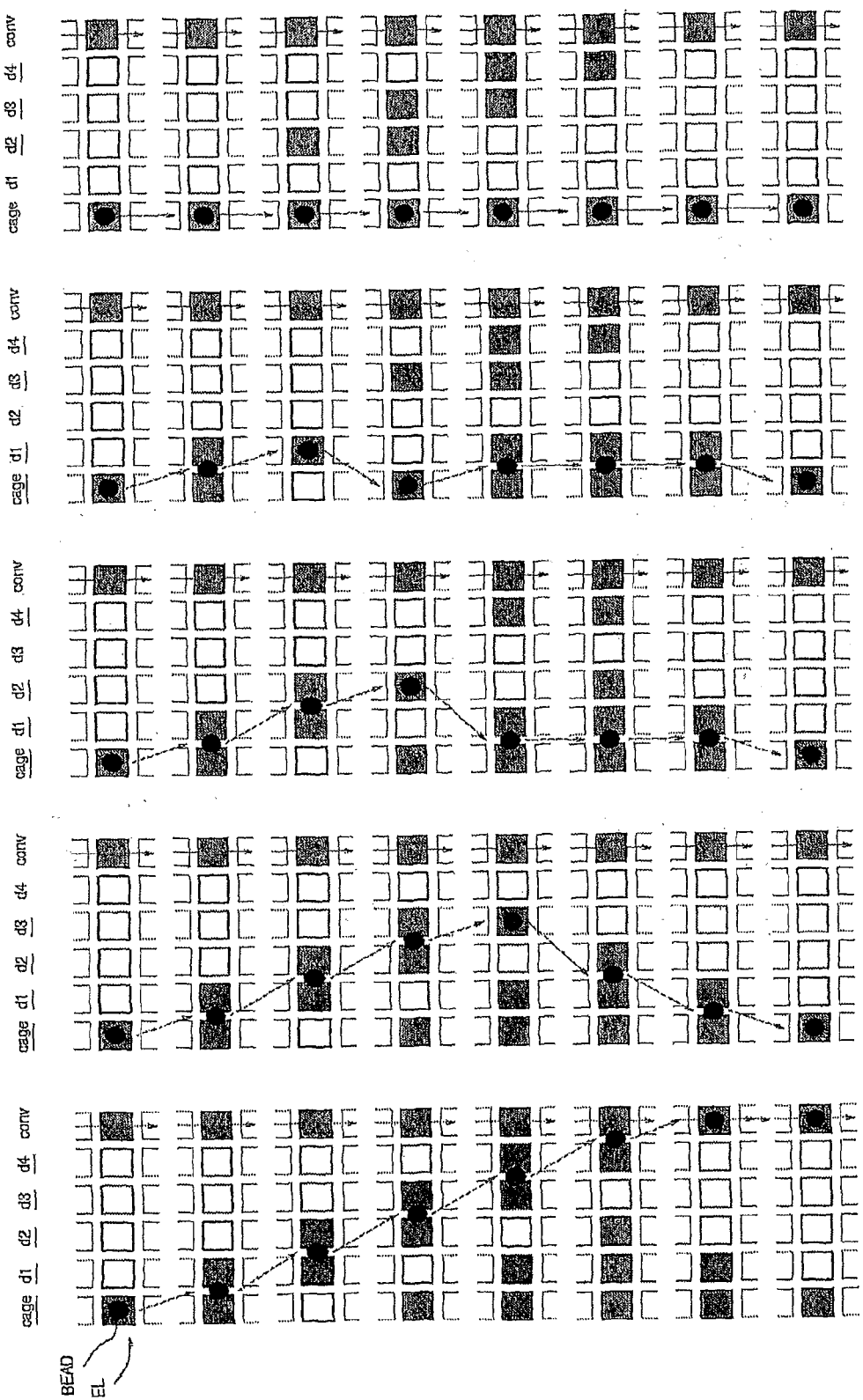
FIG. 49 shows the sequence of steps for carrying out the exchange between a parking cell (or a conveyor) and a conveyor, in the case of logic organization of the parking cells (conveyors) in four dimensions, for the selected parking cells (the conveyor) and for non-selected parking cells (conveyors).

The transfer of the cage from the parking cell to the lane is made in general by means of an appropriate sequence of activation of the control signals. The sequence is chosen so as to push from the parking cell to the lane only the cage that corresponds to the desired location, whilst all the other cages in parking cells make at most a few steps in the direction of the lane, but reverse then the sense of displacement without completing the transfer, and at the end drop back into the original position. FIG. 49 shows the example of a possible sequence of activation of the electrodes (EL), to bring particles (BEAD) from a parking cell (cage) to a conveyor (cony), in the case of a logic organization in four dimensions (d1, d2, d3, d4). The underlining of each signal "di" symbolizes the fact that the cell corresponds to a selected dimension. Consequently, the signals di are programmable both for the negative phase (activation, indicated by a shading) and for the positive phase (empty). The signal cage is in this case programmable, and the number of different signals cage must correspond to the number of addressing signals (D1) of the first dimension d1. In this way, the movement of the particle (BEAD) from the starting cage is repeatable and deterministic, as illustrated in FIG. 49. The number of parking cells addressable with D dimensions is equal to the product of the number of addressing signals of each dimension, i.e., $D1 \times D2 \times \ldots D_D$, whilst the number of necessary control signals amounts to $2 \times D1 + D2 + \ldots + D_D$.

The implementation of the apparatus according to the present invention can be obtained exploiting different technologies according to the known art. By way of example, we may cite photolithographic techniques. Three metal levels are ideal for minimizing the resistance of the paths, in so far as in this case for the row and column lines it is not necessary to have any transition between one level and the other (the ways and the associated resistances are avoided). Two metallizations are, however, sufficient in the case where ways are also used for the row and column signals. The horizontal and vertical pitches (PITCH), i.e., the distance between the centres of two adjacent blocks either horizontally or vertically, in this device is equal, respectively, to five times or twice the pitch between adjacent surface metals. To obtain the electrodes noble metals (gold, platinum, etc.) can be used or else conductive oxides, which are particularly useful in so far as said oxides are transparent (Indium Tin Oxide—ITO). To make the substrate insulators (glass, polycarbonate, etc.) or else semiconductors (silicon, etc.) can be used. To make the cover (LID) an insulating substrate provided with an electrode can be used, which can also be obtained by means of metals or conductive oxides, which are particularly useful when said conductive oxides are partially or totally transparent. It is evident to persons with ordinary skill in the sector that other geometries different from the ones described in the present patent by way of example can be used for the production of the apparatus according to the present invention.

In general, apparatuses with arrays of regular electrodes (i.e., those without rings or the like) are preferable in the use with the EWOD force.

Apparatus for the Manipulation of Particles with Lanes and Parking Cells with Transistors and/or Memory Elements By way of non-limiting example, a further possible embodiment is shown based upon the use of active substrates, in which transistors and/or memory elements are used.

Apparatus for the Manipulation of Particles with Conditioning Circuits for Lanes Each of the signals (Vh_1, Vh_2, Vh_3) used for supplying the electrodes of the corridors oriented horizontally (HRCH), and each of the signals (V1_j, V2_j and V3_j) used for supplying the electrodes of the corridors oriented vertically (VRCHJ) can be connected to signals common to the entire apparatus (Vphin, Vphip) through electronic circuits that form multiplexers. Said multiplexers can be programmed through digital signals or by means of individually addressable memory elements. The circuit embodiment that implements this scheme can be obtained according to any of the methods known to persons with ordinary skill in the sector. This technique enables a reduction in the total number of signals necessary for driving and/or programming the entire apparatus.

Apparatus for the Manipulation of Particles with Conditioning Circuits for Parking Cells Likewise, each of the signals (Vcage_j, Vcol_j, Vrow_i) used for supplying the electrodes of the parking cells can be connected to signals common to the entire apparatus (Vphin, Vphip) through electronic circuits that form the multiplexers. Said multiplexers can be programmed through digital signals or by means of individually addressable memory elements. The circuit embodiment that implements this scheme can be obtained according to any of the methods known to persons with ordinary skill in the sector. This technique enables a reduction in the overall number of signals necessary for driving and/or programming the entire apparatus.

Method for the Manipulation of Particles with Lanes

In a further embodiment of the method according to the present invention the points of equilibrium are constrained, in groups, to move in a synchronous way, along pre-set paths referred to as "lanes". Points of exchange between the groups enable the particles to pass from one group to another, i.e., to change lane. Notwithstanding these additional constraints, the method enables in any case manipulations of individual particles, and, after a series of steps, displacement of a single particle, leaving the position of all the others unaltered.

Figure 26:
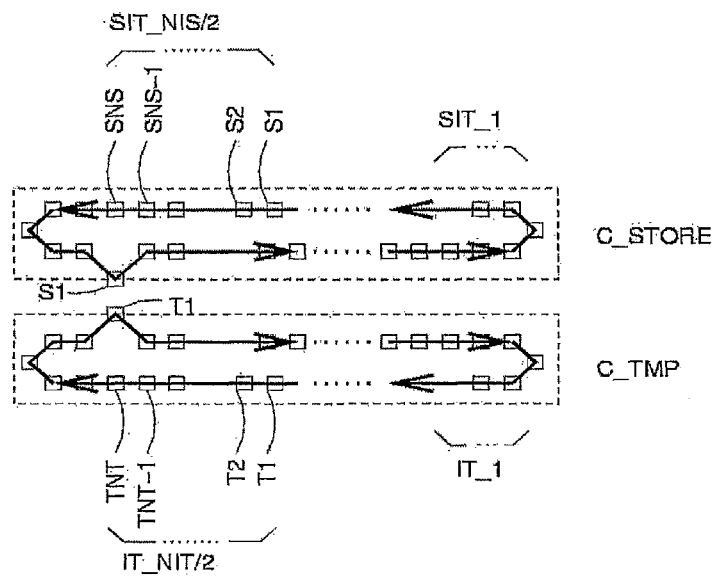
FIG. 26 shows an implementation of the method for the manipulation of particles with two lanes that close in a circle.
Figure 27:
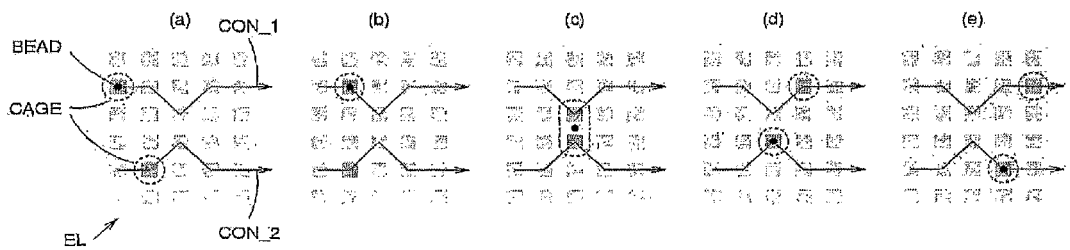
FIG. 27 shows the sequence of the steps necessary for exchange of a particle between two lanes in the case of an array of square electrodes.
Figure 28:
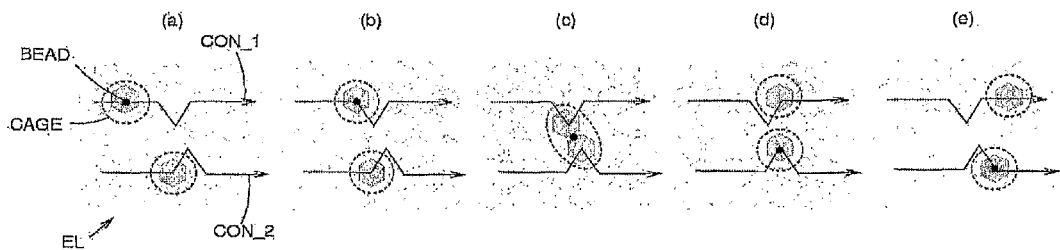
FIG. 28 shows the sequence of the steps necessary for exchange of a particle between two lanes in the case of an array of hexagonal electrodes.

An example of the working principle of the method is illustrated in FIG. 26. Two lanes, that are closed in a circle, are sufficient. In the first lane (C_STORE), driven by NS phases $S_1 \cdot S_{NS}$, repeated NIS times, particles can be introduced, possibly even in a random order. By transferring one or more particles onto the second lane (C_TMP), driven by NT phases $T_1 \cdot T_{NT}$, repeated NIT times, it is possible to re-order the particles on the first lane. The minimum number of phases for each lane is 3. Consequently, with 6 phases it is possible to control an arbitrary distribution of particles. The exchange between two lanes can be obtained with a sequence of steps as illustrated in FIG. 27a-e, which shows a particle (BEAD) in an attraction cage (CAGE) on a first lane (CON_1) whilst it is being carried into the point of exchange with the other lane [FIG. 27c], by changing the programming of the electrodes (EL). By moving away [FIG. 27d] the cage of the first lane when a cage is present in the point of exchange on the second lane (CON_2), the particle passes onto the latter. FIG. 28 shows a similar sequence in the case of an array of hexagonal electrodes. This embodiment is particularly suited to use with the EWOD force. However, it is possible to obtain the exchange between lanes using more complex configurations of electrodes, exploiting one of the methods described for the purposes of the present invention.

In a further embodiment of the method according to the present invention, just a single lane is used for causing all the particles to shift in order to reposition a given particle in a given position. It is evident that said method applies to the generic case of a number of lanes, without, however, envisaging any exchange between lanes. In this case, it is useful for the lanes not to be constrained to one another.

Apparatus for the Manipulation of Particles with Lanes without Transistors

Apparatus for the Manipulation of Particles with 9 Control Signals

Figure 29:
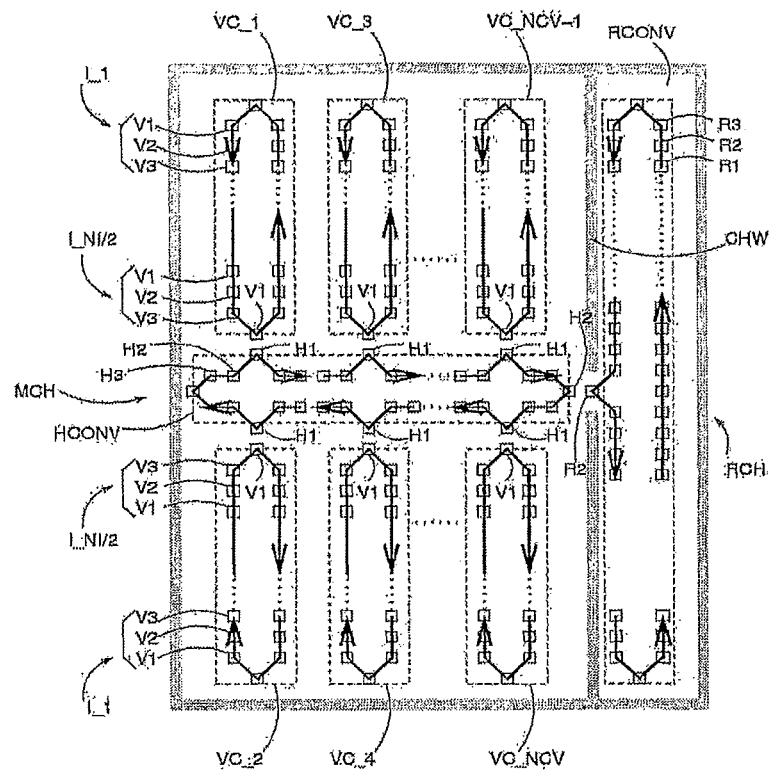
FIG. 29 shows an apparatus for the manipulation of particles with lanes and without transistors, based upon 9 control signals.

FIG. 29 shows a preferential embodiment of an apparatus for the manipulation of particles with lanes, without the use of transistors. NCV vertical circular lanes VC_1. VC_NCV each form NI cages (CAGES), by means of 3 phases, V1, V2 and V3. Said phases are connected repeatedly at each iteration I_1 . . . I_NI of a group of 3 electrodes. Said phases are common to all the lanes. A second horizontal circular lane (HCONV), driven by three phases H1, H2 and H3, comprises NCV points of exchange with the vertical conveyors, active in the phase V1+H1, so that it is possible to transfer simultaneously the contents of NCV cages from the vertical lanes to the horizontal lane. Said vertical and horizontal lanes are obtained in a first microchamber (MCH). A third lane (RCONV), driven by the phases R1, R2 and R3, is obtained in a second microchamber (RCH), separated from the first by a diaphragm (CHW). Said third lane comprises a point of exchange active during the phase H2+R2.

This apparatus is particularly suitable, for example, for isolating individual particles, for example cells suspended in a liquid. A multitude of particles can be injected into the first microchamber (MCH). A liquid without particles is injected in the second microchamber (RCH). One or more particles of interest can be selected and conveyed from the vertical lanes of the first microchamber (MCH) to the horizontal lane and from here to the third lane in the second microchamber. From here the particles can be made to flow out and recovered separately.

Apparatus for the Manipulation of Particles with 7 Control Signals

Figure 30:
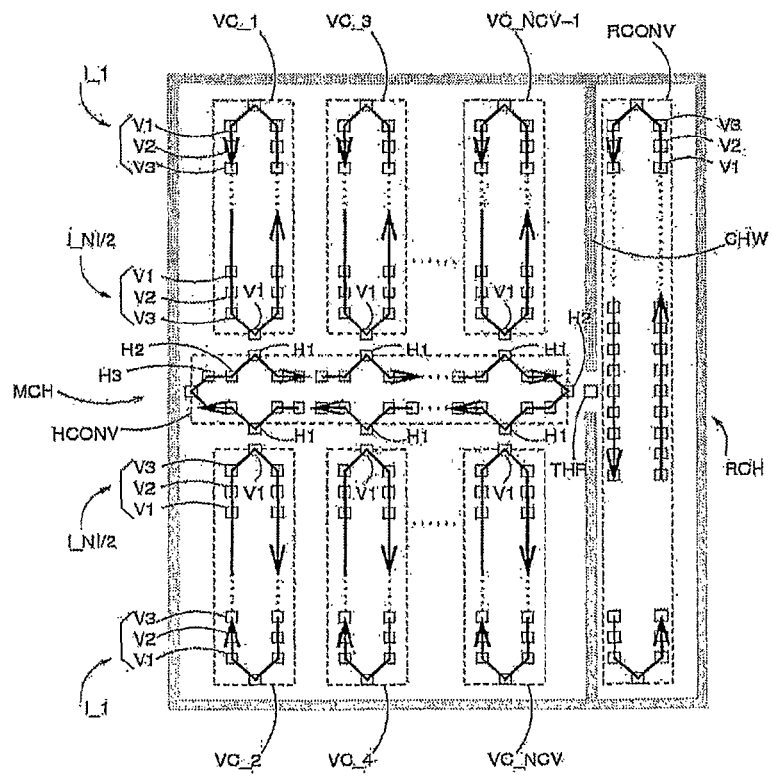
FIG. 30 shows an apparatus for the manipulation of particles with lanes and without transistors, based upon 7 control signals.

The embodiment of the apparatus can be further simplified, for the isolation of individual particles, by constraining the third lane (RCONV) to move in a synchronous way with the vertical lanes so as to share the phases V1, V2 and V3 thereof, as illustrated in FIG. 30. In this case, however, a phase (THR) is to be added for controlling the transfer from the horizontal conveyor (HCONV) to the third conveyor (RCONV). The total number of phases is thus reduced to 7. Notwithstanding the constraints of this apparatus with the use of lanes alone, it should be noted that the number of steps to bring an individual particle from a point of the first microchamber (MCH) into a point of the second microchamber (RCH) is, to a first approximation, approximately equal to the number of steps of an apparatus that enables independent movement of all the particles.

Apparatus for the Manipulation of Particles with Separate Lanes and Chambers

Figure 31:
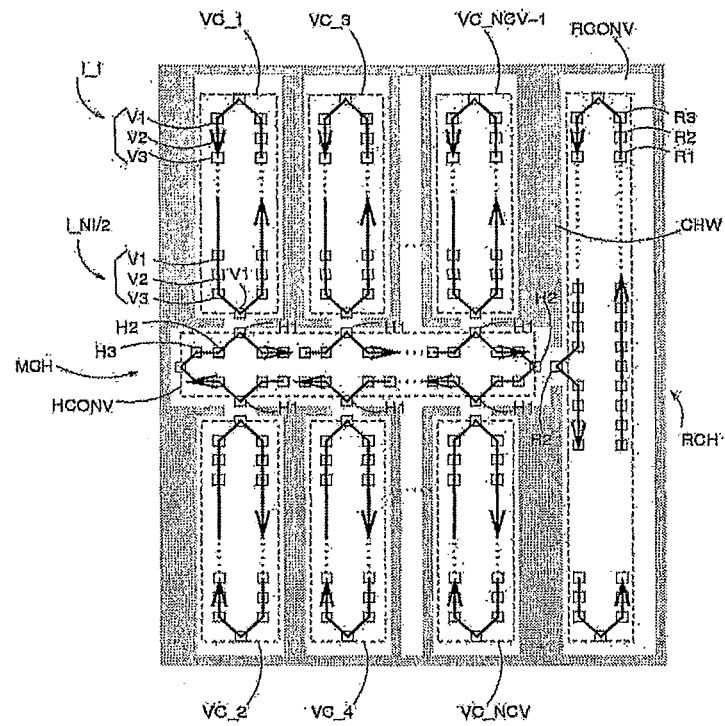
FIG. 31 shows an apparatus for the manipulation of particles with separate lanes and chambers, without transistors.

A preferential embodiment of the apparatus for management of particles of a different type is shown in FIG. 31. In this case, each vertical lane is obtained in a separate microchamber and is controlled by separate signals. For example, in different vertical chambers different particles can be injected. It is thus possible to transfer in an orderly way, onto the horizontal lane (HCONV), particles of different types, or else it is possible to bring particles of one type to interact with particles of a second type coming from a second microchamber.

Apparatus for the Manipulation of Particles with Lanes with Transistors and/or Memory Elements Each of the signals used for supplying the electrodes of the corridors (C_STORE, C_TEMP, VC_i, HCONV, RCONV) can be connected to signals common to the entire apparatus (Vphin, Vphip) through electronic circuits that form multiplexers. Said multiplexers can be programmed through digital signals or by means of individually addressable memory elements. The circuit embodiment that implements this scheme can be obtained according to any of the methods known to persons with ordinary skill in the sector. This technique enables reduction in the overall number of signals necessary for driving and/or programming the entire apparatus.

Figure 32:
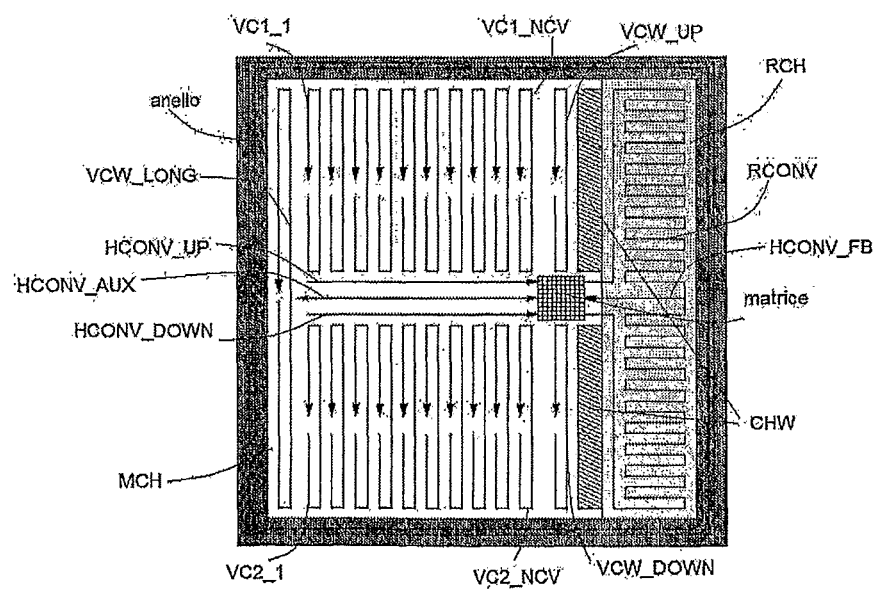
FIG. 32 shows an apparatus for the manipulation of particles with lanes, a completely programmable matrix array and separate chambers, without transistors.

Apparatus for the Manipulation of Particles with Lanes and Completely Programmable Array In a further embodiment of the present invention, the technology of the apparatus of FIG. 23, implemented, according to techniques similar to those used in the apparatuses of FIGS. 29, 30, 31 already described, is used to obtain the complex apparatus illustrated in FIG. 32, which enables optimization of the possibilities and times of manipulation of the particles and at the same time containment of the number of control signals necessary. According to what is illustrated in FIG. 32, this apparatus according to the invention is divided by a diaphragm (CHW) made of polymeric material into two microchambers (MCH, RCH).

The first microchamber (MCH) is substantially constituted by:

a. a first multiplicity and a second multiplicity of vertical circular lanes (definable also as "conveyors") (i.e., ones forming a closed loop, albeit elongated) $VC1\_1 \ldots VC1\_NCV$, and $VC2\_1 \ldots VC2\_NCV$ each forming NI cages (CAGES), by means of three phases V1, V2 and V3, connected repeatedly at each iteration $I\_1 \ldots I\_NI$ of a group of three electrodes;

b. a first horizontal circular lane and a second horizontal circular lane HCONV_UP, HCONV_DOWN (or even simply a linear lane, i.e., with electrodes arranged to form a portion of array in a straight line instead of in a loop), driven by four phases H1, H2, H3 and H4 comprising NCV points of exchange with the vertical lanes (conveyors), active in the phase V2+H3, so that it is possible to transfer simultaneously the contents of one or more cages from the vertical lanes to the first horizontal lane;

c. a third circular horizontal (or simply linear) lane HCONV_AUX, driven by four phases AUX1, AUX2, AUX3 and AUX4, which comprises NCAUX1 points of exchange with the conveyor or an upper horizontal lane HCONV_UP and an identical number NCAUX2 of points of exchange with the conveyor or lower horizontal lane HCONV_DOWN, situated in positions corresponding to one another;

d. a completely programmable matrix array of electrodes, for example a square array of 5×5 electrodes, each controlled individually through special dedicated phases, or yet again using electrodes of a completely active type, as in the known art, each equipped with programmable memory elements and transistors, so as to form in use a matrix array of individually programmable attraction cages;

e. a first circular vertical dump lane VCW_UP and a second circular vertical dump lane VCW_DOWN driven by 3 phases in a way substantially similar to what has already been described for the vertical lanes $VC1\_i$ and $VC2\_j$, which have the function of removing undesired particles from the array;

f. a long circular vertical dump lane VCW_LONG, having a dimension approximately twice that of the vertical lanes $VC1\_i$ and $VC2\_j$, which is also driven by three phases in a way substantially similar to what has already been described for the vertical lanes $VC1\_i$ and $VC2\_j$, set in the portion of the microchamber MCH on the side opposite to the array.

The second microchamber (RCH) is substantially constituted by an exit lane RCONV, driven by the four phases R1, R2, R3 and R4, for conveying the particles leaving the array of interest into the second microchamber, through a discontinuity of the diaphragm made of polymeric material CHW constituting a passage of communication between the two microchambers. There is moreover provided a horizontal feedback lane HCONV_FB, driven by four phases FB1, FB2, FB3 and FB4, lying substantially on the same straight line identified by the auxiliary horizontal lane, by means of which it is possible to bring a particle back from the exit lane RCONV, and hence from the microchamber RCH, into the array, once again through the aforesaid passage in the diaphragm CHW.

In a particular embodiment of the present invention, the vertical circular lanes are 400, arranged in 20 groups of 20 elements. Since the first microchamber MCH is fundamentally divided by the horizontal lanes into two half-chambers, a top one and a bottom one, the vertical lanes are 200 in the top half and 200 in the bottom half. The structure is hence completely symmetrical.

Figure 33:
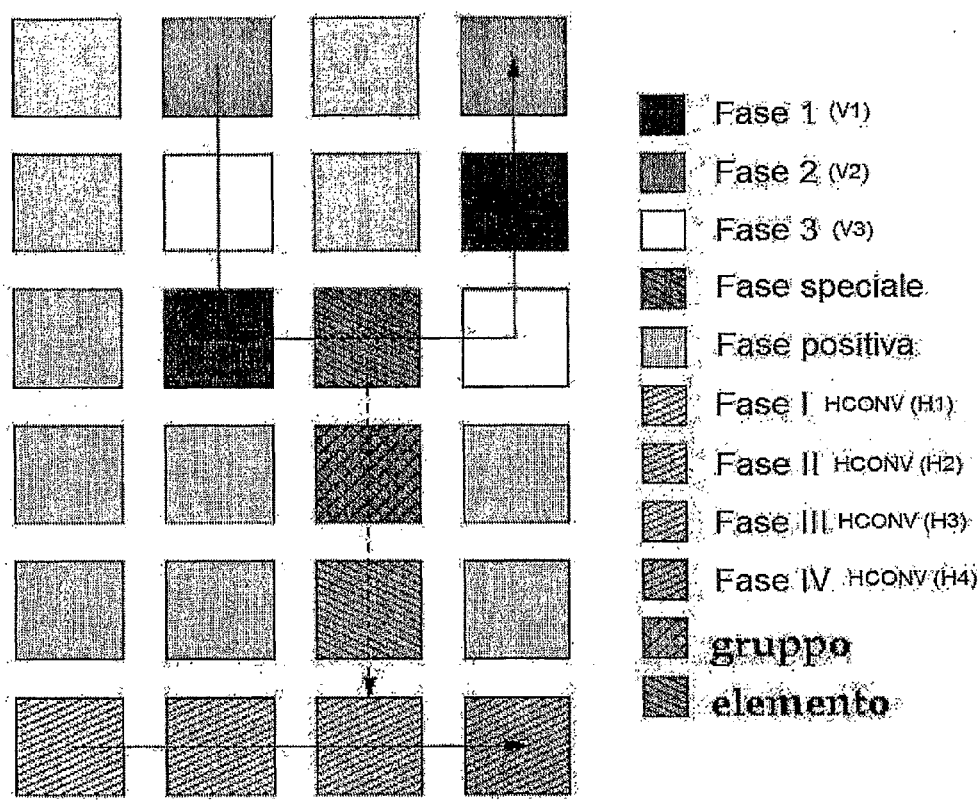
FIG. 33 shows the point of exchange for the passage of a particle between a vertical lane and a horizontal lane of the apparatus for the manipulation of particles of FIG. 32.

Each individual lane is able to displace a particle and rotate it using a three-phase protocol. It is possible in any case to extract from a lane a particle of interest using one of the (controllable) NCV points of exchange, positioned immediately on top of the horizontal lane HCONV_UP for the vertical lanes upwards and immediately underneath the horizontal lane HCONV_DOWN for the vertical lanes downwards. Each point of exchange is defined by a pair of electrodes, referred to, respectively, as "element" and "group" (FIG. 32). Since the group electrodes and element electrodes are 20, the number of the addressable exchanges is 400, equal to the number of the vertical lanes. The special-phase signal is the same for each lane within a group, so that the behaviour of the signal special phase and of the signals of a group electrode are the same for each conveyor of the group. The same does not apply to element electrodes. It is always possible, in this way, to transfer a particle of interest from a vertical conveyor to a horizontal conveyor in order to convey it as far as the programmable array and possibly to the exit point, without loading any other particle into the horizontal conveyor. The change of direction, i.e., the transfer from a vertical lane to a horizontal lane is made possible by an electrode guided by a special phase (FIG. 33). Usually, said electrode is located in the same phase as the signal of Phase 2, but in the case of a particle of interest, when all the other signals of Phase 2 remain negative (i.e., active) also the special signal becomes negative (FIG. 34), thus leaving the cell to be transferred through the point of contact if the element electrode and group electrode are active. When, instead, the signal of the element is not in the negative phase (what is instead true for all the other 19 lanes not concerned in the exchange), the operation is the one illustrated in FIG. 35.

Figure 35:
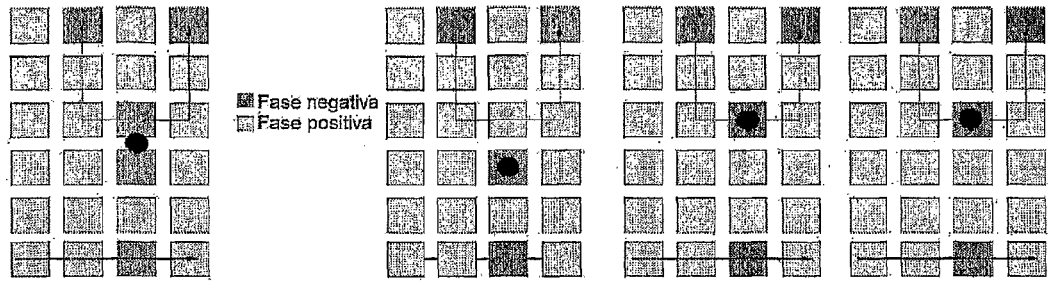
FIG. 35 shows the operation, during the exchange between a vertical conveyor and a horizontal conveyor of a certain group and element, for a vertical conveyor belonging to a different element of the same group, of the apparatus for the manipulation of particles of FIG. 32.

In this way, the particles can be joined to the conveyors upwards and downwards. The operation illustrated in FIG. 35 is moreover useful when it is desired to modify the order of the particles within one and the same vertical lane, in so far as it makes possible temporary deposit of a particle at the group electrode external to the vertical lane, and then get it to come back into the vertical lane itself.

In a way similar to what was illustrated previously in the description of the apparatus with lanes and parking cells without transistors, also in this case of the apparatus with lanes and programmable array it is possible to adopt a logic organization of the conveyors not in two dimensions (as described above) but in D dimensions. By way of example, reference may be made once again to FIG. 49, described previously, as representation of the transfer of a particle (BEAD) from the end of a vertical conveyor (cage) to a horizontal conveyor (cony). To persons with ordinary skill in the sector it is clear how it is possible to generalize the sequence of operations for performing the exchanges from vertical lanes to the horizontal lane only for the lane selected, i.e., only for that for which all the D (=4, in the example) signals of exchange of each dimension are selected.

With the horizontal lanes (HCONV_UP, HCONV_DOWN), the particles of interest can be transferred into the completely programmable matrix array, in which it is possible to carry out complex operations, such as for example the division of clusters of particles. This is particularly useful, for example, when the mean density of cells per cage in the sample injected is equal to or greater than one. In this case, the probability of having a single cell in the cage decreases, and consequently it is likely for the cells of interest to form part of a cluster. The presence of the completely programmable matrix array enables segregation in different cages of the cells forming part of a cluster.

Figure 36:
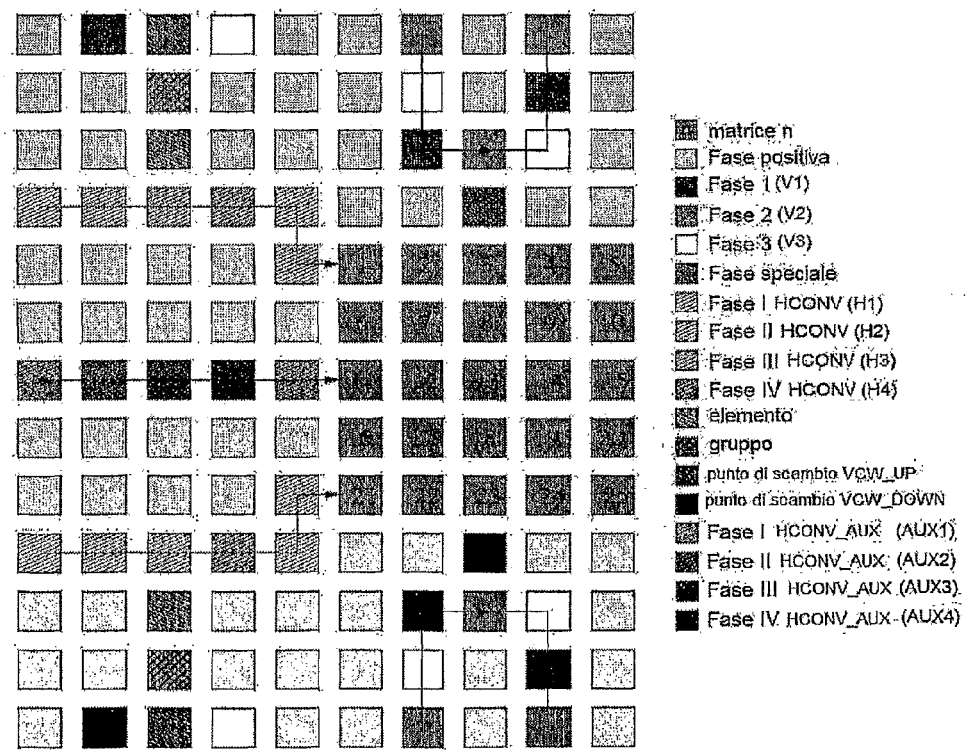
FIG. 36 shows a portion of the apparatus for the manipulation of particles of FIG. 32 in the immediate vicinity of the completely programmable matrix array.

In the preferential embodiment, a matrix array is a square of 5×5 completely programmable electrodes, as illustrated in FIG. 36, which shows the relative interaction thereof with the horizontal conveyors and auxiliary conveyor.

Figure 37:
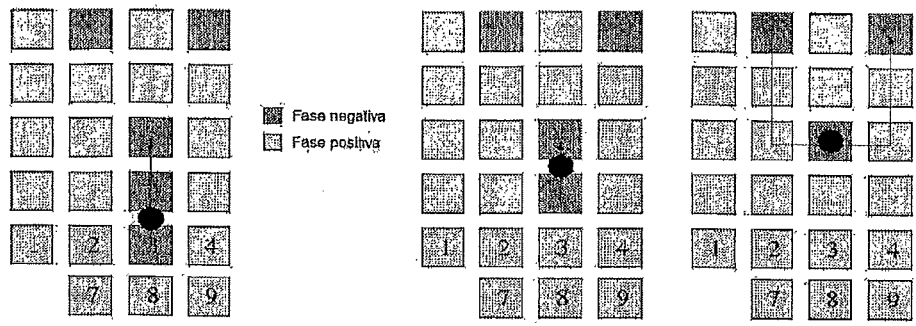
FIG. 37 shows the sequence of steps necessary for the passage of a particle from the completely programmable matrix array to a waste lane.

By means of the matrix array it is possible to select and withhold the particles of interest, whilst, after the segregation in separate cages, the others can be moved away after being transferred to the dump lanes. The points of exchange between array and dump lanes function like the other points of exchange, but without the two element and group electrodes (FIG. 37).

Figure 38:
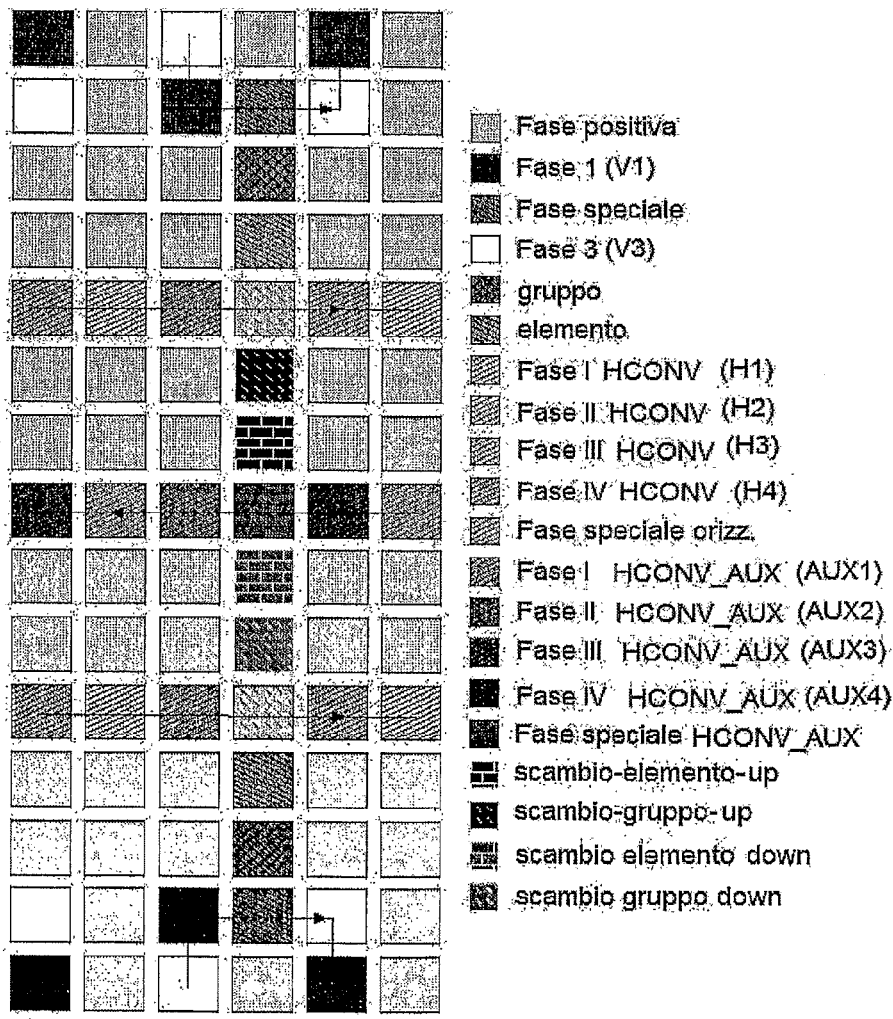
FIG. 38 shows the point of exchange for the passage of a particle from the completely programmable matrix array to the auxiliary lane.

The auxiliary lane HCONV_AUX can be used as support for the two horizontal lanes HCONV_UP and HCONV_DOWN, for example in the case of any malfunctioning due to clogging of particles, etc. In a preferred embodiment of the apparatus, between the three horizontal lanes 12 points of exchange are provided, made with a double point of exchange, as illustrated in FIG. 38.

Figure 39:
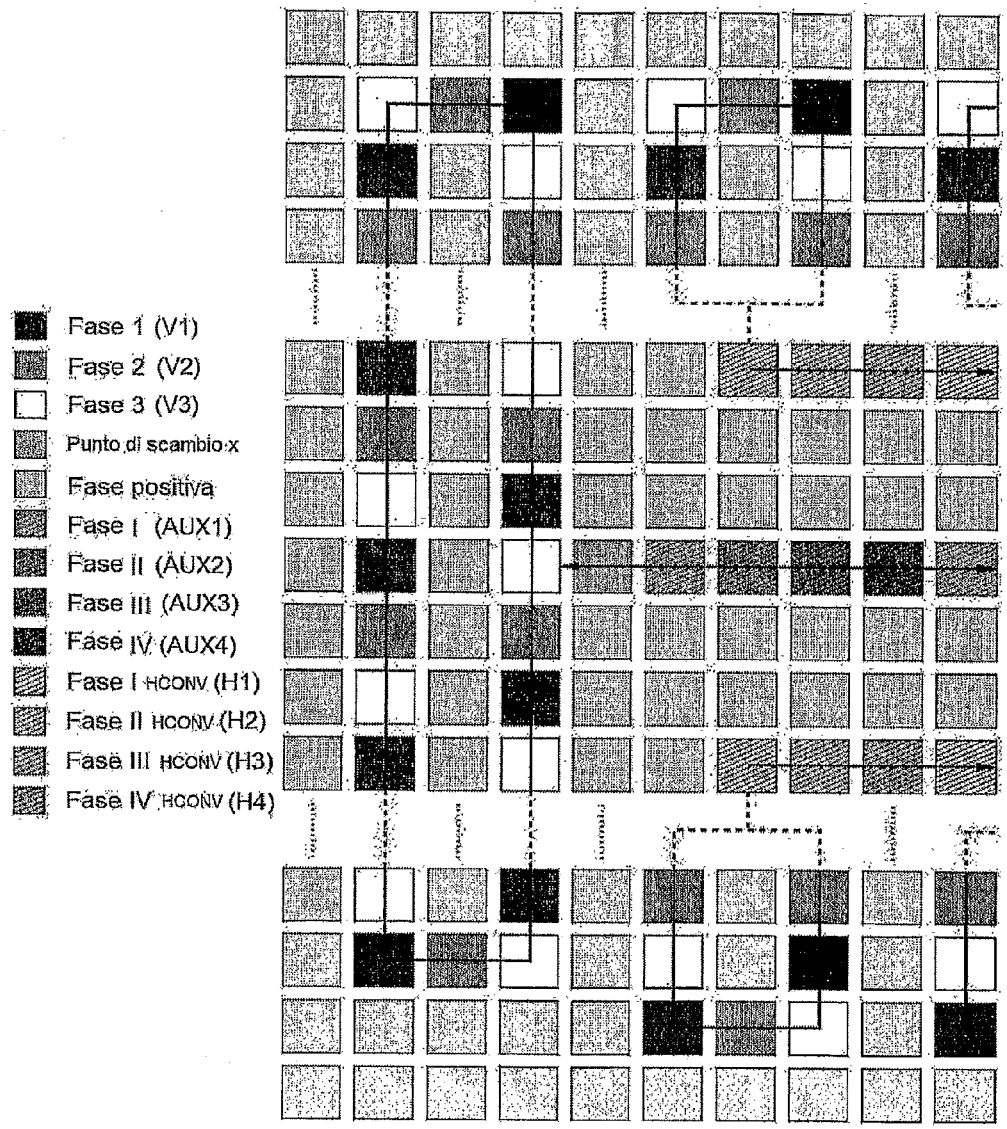
FIG. 39 shows the exchange gate for the passage of a particle from the auxiliary lane to the waste lane long.

The auxiliary lane can also be used to eliminate the undesired particles, particularly during the step of start-up of the apparatus. FIG. 39 shows the left-hand end of the auxiliary lane, where it is possible to transfer the particles in the long dump lanes through an individual point of exchange.

Located at exit from the matrix array (FIG. 40) are the dump lane upwards VCW_UP and the dump lane downwards VCW_DOWN. The exit lane RCONV is a 4-phase lane, which conveys the cells of interest out of the microchamber MCH and into the microchamber RCH. In order to have the highest possible number of cages, the path towards the exit point proceeds by zigzagging (FIG. 41) all the way through the microchamber RCH. When the particles are in the exit lane, they can be brought back into the array by means of the horizontal feedback lane HCONV_FB.

The latter splits the exit lane in a symmetrical way, identifying in effect a top exit half-lane and a bottom exit half-lane. It should be noted that said half-lanes are completely independent of the operative standpoint, and it is consequently possible to use even just one of them.

The active area of the apparatus is surrounded by a ring (FIG. 42), in turn made up of two concentric rings of electrodes in positive phase, followed by a ring of electrodes in positive phase alternating with dummy electrodes (for example floating electrodes), which are in turn followed by two rings of electrodes in positive phase. The dummy electrodes are aligned with the columns of the conveyors.

It should be noted that the embodiment of the invention just described advantageously enables combination of the simplicity of programming and management (number of phases for control of the lanes downwards) with the precision (possibility of carrying out complex manipulations of the particles of interest inside the array, having the possibility of intervening independently on each of the individual cages that constitute it).

Apparatus for Recognition and Counting of Particles

To each of the methods for manipulation of particles according to the present invention, both with homogeneous arrays and with parking cells and lanes or even with just lanes a part for detection of the particles can be added in order to distinguish, recognize, characterize, or count cells/particles. The distinction or recognition can be obtained according to the known art in different ways:

1. distinguishing/recognizing different particles/cells that have the same reactive behaviour to the impressed forces F, but that affect differently reading of the sensor; for example, particles with a different index of transparency affect differently reading of the intensity of light of a photodiode;

2. distinguishing/recognizing particles/cells that have a different behaviour to the impressed forces F, but the same behaviour for the sensor; for example, cells of different dimensions can have a different rate of displacement, and it is hence possible to recognize them by monitoring the time used to pass from one block (BLOCK_i,j) to the adjacent one (BLOCK_i,j+1);

3. distinguishing/recognizing particles/cells that have a different reactive behaviour to the impressed forces F and in any case a different behaviour for the sensor.

Recognition can be combined with a method for counting cells obtained by combining the effect of the forces (F), through which to position each cell (or group of cells) in a point corresponding to an element of an array of sensors, and the capacity of identifying the presence of each cell (or group of cells) by means of said sensors. In this way it is possible, in addition to recognizing, also to count the particles of each type.

In each embodiment of apparatus for the manipulation of particles according to the present invention, both with homogeneous arrays and with parking cells and lanes or also with just lanes, it is consequently possible to add a part for detection of the particles.

Different embodiments are possible so that the detection is made via impedance meter or optical sensors. Of particular interest is the possibility of detecting the particles even without an active substrate, i.e., without transistors.

Apparatus for the Manipulation of Particles without Transistors with Impedance Meter Sensors It is hence possible to monitor the perturbation imposed by the presence of a particle on the electrical field that is created between adjacent elements of an array of electrodes for the purpose of individuating, quantifying and/or qualifying the presence of particles. In the case of homogeneous arrays, a measurement can be made of the presence of one (or more) particles and possibly its (their) characterization by means of measurement of the impedance between the paths normally used to carry the row signals and column signals.

With reference to FIG. 5, it may be understood how the impedance between, for example, Vrow_i and Vcol_j is markedly affected by the presence or absence and by the type of particles possibly entrapped in the cage CAGE_i,j, and slightly affected by the possible presence of particles in surrounding cages.

A similar measurement can be made in the case of an apparatus with lanes and parking cells. With reference to FIG. 23, it may be understood how the impedance between, for example, Vrow_i and Vcol_j, is markedly affected by the presence or absence and by the type of particles possibly entrapped in the cage of the block BLOCK_i,j, and only slightly affected by the possible presence of particles in surrounding cages.

Of course, it is possible to add row and column paths specifically for detection, without thus having to multiplex the actuation and the detection.

Figure 43:
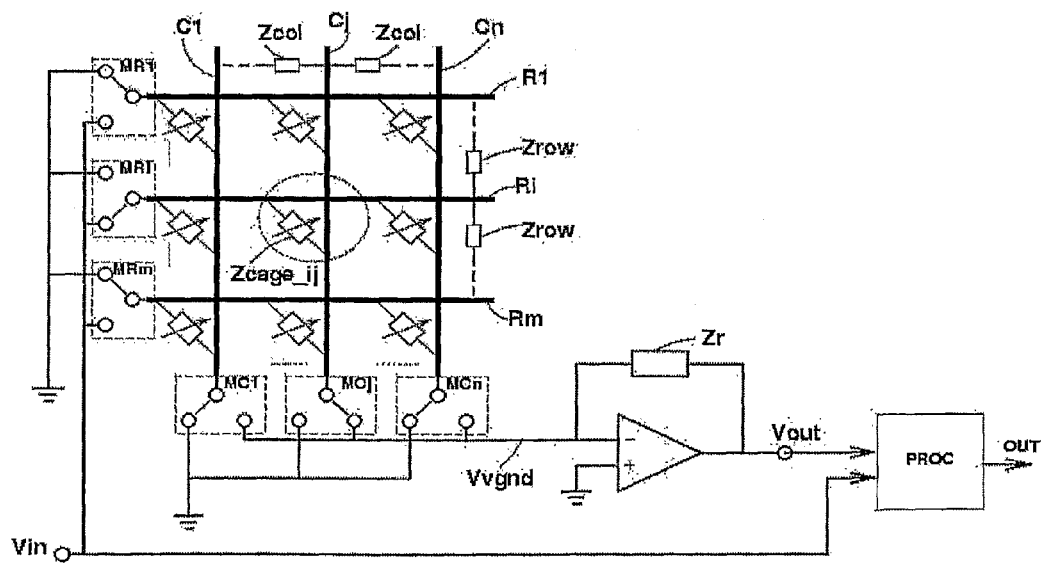
FIG. 43 shows an apparatus for the manipulation of particles without transistors and with impedance meter sensors.

FIG. 43 shows a reading scheme according to the present invention for detecting the impedance of the individual intersections (Zcage_ij) between generic lines of row signals (Ri) and column signals (Cj), without undergoing the influence of the coupling between adjacent rows (Zrow) and columns (Zcol), which otherwise would render detection impossible, in so far as their value is typically dominant with respect to Zcage_ij. This reading scheme can be obtained with an electronic system with components external to the microfabricated chip, and hence compatible with the use of substrates without transistors, but can also be integrated on the chip in the case where transistors are available.

An input stimulus (Vin), with zero mean value, is applied selectively to a row (Ri), enabling only its multiplexers MRi. The other row multiplexers MR1 ... MRi-1, MRi+1 ... MRm connect the remaining rows to ground. Just one column (Cj) corresponding to the co-ordinate of the intersection impedance (Zcage_ij) to be measured, is multiplexed on the virtual ground (Vvgnd) of a transimpedance amplifier, the output of which (Vout) is inversely proportional to the unknown impedance:

$$Vout = -Vin * Zr/Zcage\_ij$$

Said output voltage (Vout) can hence be used to derive Zcage_ij, with Vin and Zr known. The output Vout, in general, can be processed, possibly together with the input Vin, by a block for processing the signal (PROC), of an analog or digital type, to produce one or more additional—analog or digital—outputs (OUT), representing the measurement of the impedance and hence of the presence or otherwise or also of the type of particle in the measurement point.

By way of example, we cite the case where the input (Vin) is a sinusoid at a known frequency. In this case, by processing the output of the amplifier (Vout) together with Vin it is readily possible to obtain with known techniques an accurate measurement of Zcage_ij. For example, techniques of filtering such as lock-in amplifier filtering can possibly be used in the block for processing the signal (PROC). Once again by way of example we cite the possibility of applying an input voltage (Vin) formed by the sum of a number of sinusoids at different frequencies. On account of the superposition of the effects, by separating the spectral components of the output voltage (Vout) using analog or digital filters in the processing block (PROC), it is possible to detect simultaneously, at all the frequencies which make up the input (Vin), the impedance (Zcage_ij) of the cage addressed by the row and column multiplexers (MRi) (MCj).

To speed up the reading operation it is possible to read in parallel all the columns, replicating the amplifier and the processing block for each column. In this case, it is not necessary to use any column multiplexers (MCj).

Method and Apparatus for the Detection of Particles with Impedance Meter Sensors According to the present invention, a detection apparatus can be provided also independently of the use of the chip as actuator. In this case, it is generally possible to increase the spatial resolution of detection points (at the limit obtaining a resolution equal to the pitch of the top metallization), obtaining an impedance meter image of the sample that enables resolution of individual cells.

Particularly useful is the study of the morphology of tissues formed by cell clusters in order to evaluate the roughness, humidity or other parameters useful for cosmetic applications or for dermatological studies. In this case, the measurement of impedance does not entail the use of forces and can be effected between adjacent electrodes arranged in a regular way in a two-dimensional space by positioning the tissue in contact with the substrate on which the array of electrodes is located.

The subject of the present invention is an apparatus that implements this technique by means of an array of blocks of electrodes, each constituted by at least one electrode connected to row signals and at least one electrode connected to column signals, such that the impedance between said electrodes can be evaluated by measuring the impedance between row and column. A possible particle located in the neighbourhood of each row and column intersection can in this way be detected by measuring the impedance between the row and column.

By way of example that by no means limits the scope of the present invention, we provide a possible implementation of said apparatus which is particularly useful when the rows are formed on a substrate (SUB) whilst the columns are formed on the cover (LID) facing and set at a distance from the first substrate, or vice versa. In this way, in fact, it is possible to provide parallel rectangular electrodes equal to the entire length of the apparatus arranged horizontally on the substrate (SUB), to obtain row signals, and arranged on the cover (LID), to obtain column signals. In this way, the measurement is made by evaluating the impedance between each row and column in order to determine the presence of a particle set between the row electrode and the column electrode at the intersection between the two signals. The resulting apparatus can be obtained with just one level of metallization on the substrate (SUB) and one level of metallization on the cover (LID).

Figure 44:
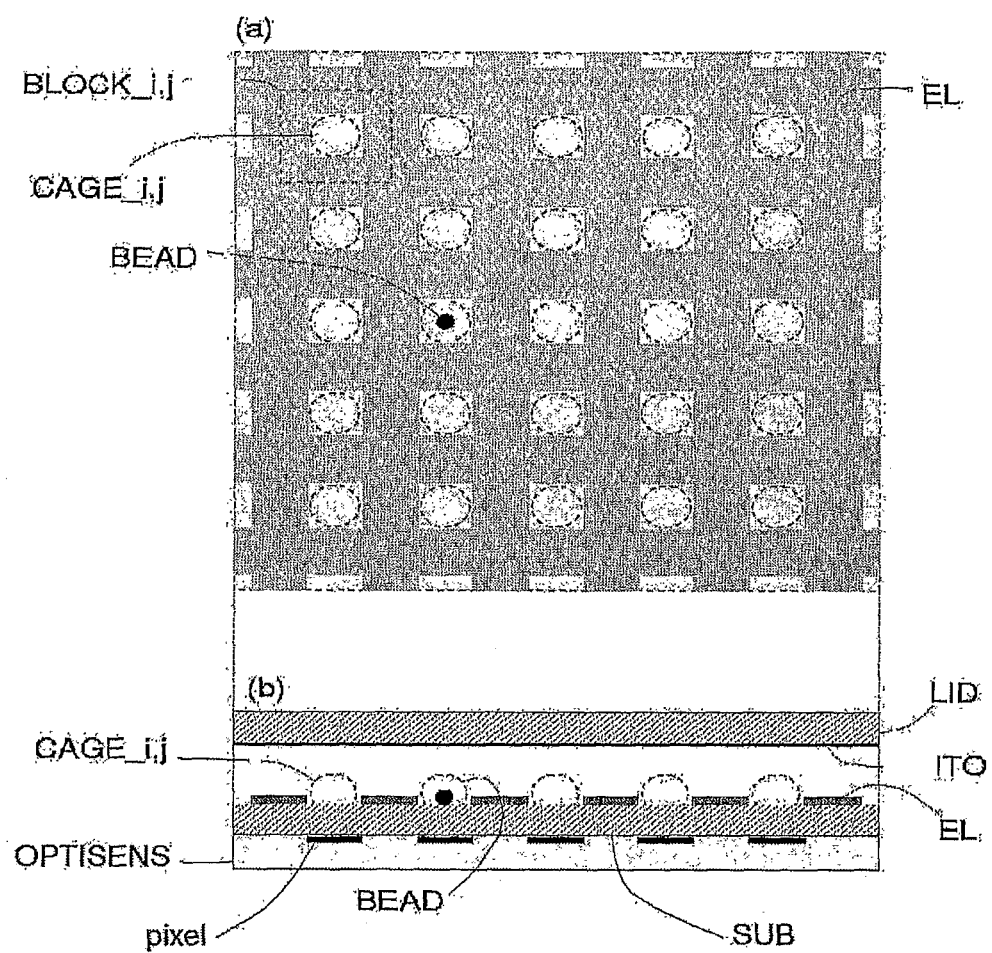
FIG. 44 shows an apparatus for the manipulation and detection and/or identification of particles formed by a grid electrode and an array of optical sensors.

Apparatus for the Manipulation of Particles without Transistors with Optical Sensors and Transparent Electrodes A further possibility of detection of the particles is constituted by the use of optical sensors underneath the device, combined to the use of transparent electrodes (such as Indium Tin Oxide—ITO). In this case, when the device is illuminated from above, the particles are detected by the variations of optical power incident on the external detection array, underneath the device. As illustrated in FIG. 44, the underlying detection system can be constituted by an array of optical sensors (pixel), for example photodiodes or CCDs, in which the distance between adjacent elements of the array of sensors is 1/N times the distance between two adjacent blocks (BLOCK_i,j), with N=1 integer. The main characteristic of this technique lies in the possibility of aligning the particles to be detected with the elements (pixel) of the sensor, improving the sensitivity of the measurements and obtaining a biunique correspondence between particle and sensor element. This technique guarantees in fact that each particle can be located only and exclusively in the sensor area of just one element of the array of sensors.

As an alternative, it is possible to use an array of external sensors set at a distance from the actuation device, in which the light reflected from above or transmitted from beneath is conveyed and focused by a series of lenses towards the sensor, the elements (pixel) of which are, however, aligned optically with the blocks of the array.

Apparatus for the Manipulation of Particles without Transistors with Optical Sensors and Non-Transparent Electrodes A further possibility of detection of the particles is constituted by the use of optical sensors (OPTISENS) underneath the device, combined with the use of non-transparent electrodes. In this case, the potential holes (CAGE) can be obtained in the proximity of the substrate, in the regions not coated with the metal of the electrodes. Shown as a particular case in FIG. 44 is a simple embodiment of the apparatus forming the subject of the present invention, in which the array of electrodes (EL) is constituted by just one electrode in the form of a square grid (other geometrical shapes are obviously possible, such as rectangles, circles, hexagons, or triangles). In this case, blocks (BLOCK_i,j) are obtained, constituted (FIG. 44a) by regions not coated with the metal of the electrode, where points of stable equilibrium (CAGE_i,j) are provided. In this way, if the substrate is transparent, it is possible to apply, underneath the apparatus (FIG. 44b), a sensor (OPTISENS) constituted by an array of photosensitive elements (pixel) for the detection of the presence of entrapped particles in each of the points of stable equilibrium. In this connection, it is preferable for the elements (pixel) of the array of sensors to be aligned optically with the array of points of stable equilibrium (CAGE_i,j), in which the distance between adjacent elements of the array of sensors is 1/N times the distance between two adjacent blocks (BLOCK_i,j), with N=1 integer. This apparatus is particularly useful for counting the particles contained in a liquid sample. In this case, the embodiment is limited to the alignment of the particles (BEAD) with the elements (pixel) of the array of sensors.

Figure 45:
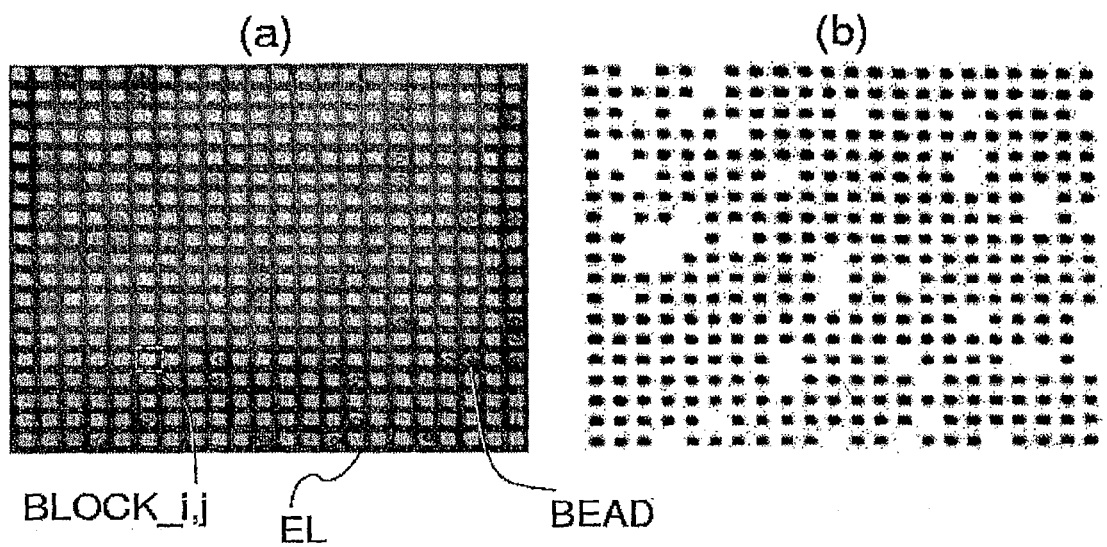
FIG. 45 shows the result of an experiment of manipulation and detection obtained by means of a prototype device formed by a grid electrode and an external optical sensor.

Given in FIG. 45, purely by way of example that in no way limits the scope of the present invention, are the results of an experiment conducted by means of a prototype obtained from a transparent-glass substrate with an electrode constituted by: a metal grid supplied with a sinusoidal signal (Vphip); a cover lid, the bottom face of which is conductive and transparent (supplied with a signal in phase opposition Vphin); an external sensor, which detects the light collected by the bottom part of the device by means of the lenses of a microscope; and a light source that irradiates the device from above. In this case, optically associated to each element of the array of points of stable equilibrium (CAGE_i,j) is a multiplicity of pixels of the sensor. In the case where an external sensor is used, as described previously it is not indispensable for the substrate (SUB) to be transparent since it is possible to use the image collected from above, irradiating the device with reflected light.

Figure 46:
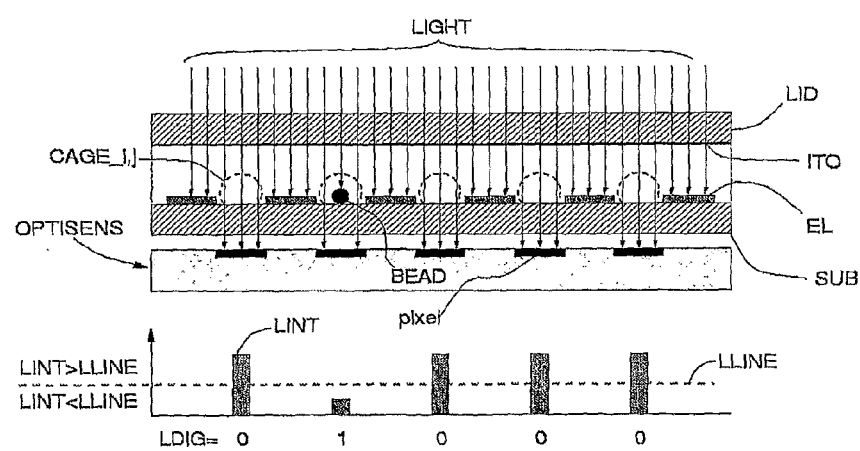
FIG. 46 shows an apparatus for the manipulation and detection and/or identification of particles by means of contact optical sensors and transmitted light.

With reference to the bottom part of FIG. 46, the signal (LINT) coming from each pixel of the sensor is converted into a digital signal by means of a hardware/software comparator that compares the signal coming from the sensor with a threshold (LLINE) appropriately fixed such that the logic value LDIG=0 (black) corresponds to the absence of any particle in the cell (BLOCK_i,j), whereas the logic value LDIG=1 (white) corresponds to the presence of a particle in the cell (BLOCK_i,j). Illustrated in FIG. 45a is an enlarged image of the device, in which the blocks (BLOCK_i,j) and the microspheres (BEAD) entrapped in the points of stable equilibrium (CAGE_i,j) are clearly visible, whilst illustrated in FIG. 45b is the processed signal corresponding to the same portion of device. In the example shown, the processing consists in an inversion of the levels of grey, followed by a blurring and a thresholding. From the resulting image an automatic count may be readily obtained. Similar results can be obtained using a contact sensor that gathers the light from beneath, as illustrated in FIG. 46, or integrated within the substrate itself. The advantage of the use of contact sensors lies in the fact that the use of the lenses of a microscope is not required. The result is an apparatus of reduced dimensions and hence portable.

It is evident to persons with ordinary skill in the sector that many other possibilities exist of integration of sensors, which are generally also simpler if it is possible to use an active substrate with transistors, which can be used for coupling an array of optical and impedance meter sensors to the attraction cages.

Figure 47:
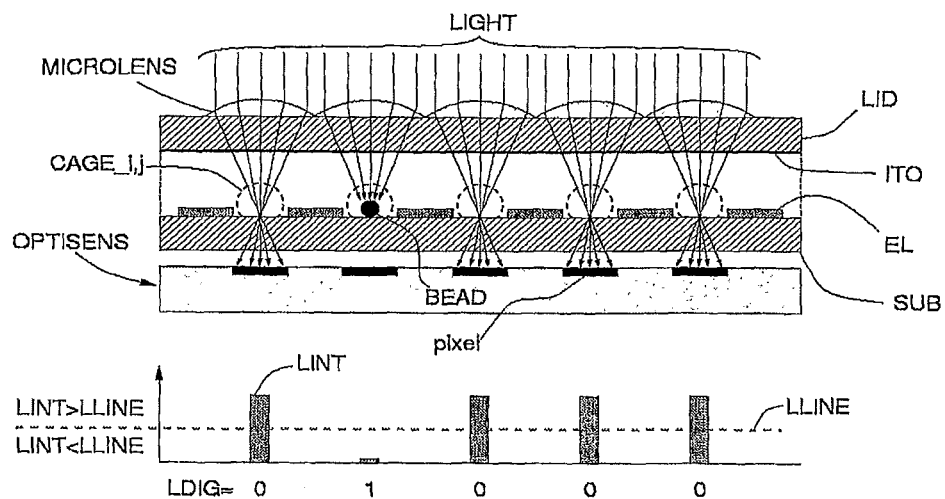
FIG. 47 shows an apparatus for the manipulation and detection and/or identification of particles by means of contact optical sensors and transmitted light that makes use of microlenses to increase the sensitivity of the measurement.

In order to improve the performance due to the use of optical sensors microlenses (MICROLENSE) can be used, which can for example be provided on the top part of the cover (LID) for conveying the light onto the entrapped particle. Illustrated in FIG. 47 is an example of this idea, in which it is shown schematically how the use of microlenses can improve the sensitivity of the measurement (gathering the light that otherwise would end up outside the sensitive region) and increase the contrast between the different levels of signal associated to the presence or absence of a particle (conveying all the rays of light into the centre of force of the cage, where the particle is positioned). It is moreover evident to persons skilled in the sector that the effects of lenses, parabolic dishes, prisms, minors, filters or polarizers can be combined for irradiating the apparatus.

As an alternative to the use of a two-dimensional array of optical sensors (pixel) it is possible to use (FIG. 48) a one-dimensional array (SENSHEAD) with sensor elements (pixel) aligned optically with a row (or with a column) of the array of points of stable equilibrium (CAGE_i,j), in which the distance between adjacent elements of the array of sensors is 1/N times the distance between two adjacent blocks (BLOCK_i,j) on the same row (or column), with N=1 integer. To acquire information on the presence/absence of particles on the whole array, an acquisition is effected in time sequence for each row (or column) of the array, displacing by a pitch (PITCH), after each acquisition, the array of sensors (pixel) with respect to the array of blocks or vice versa in the direction (HEADIR) parallel to the columns (or to the rows).

Figure 48:
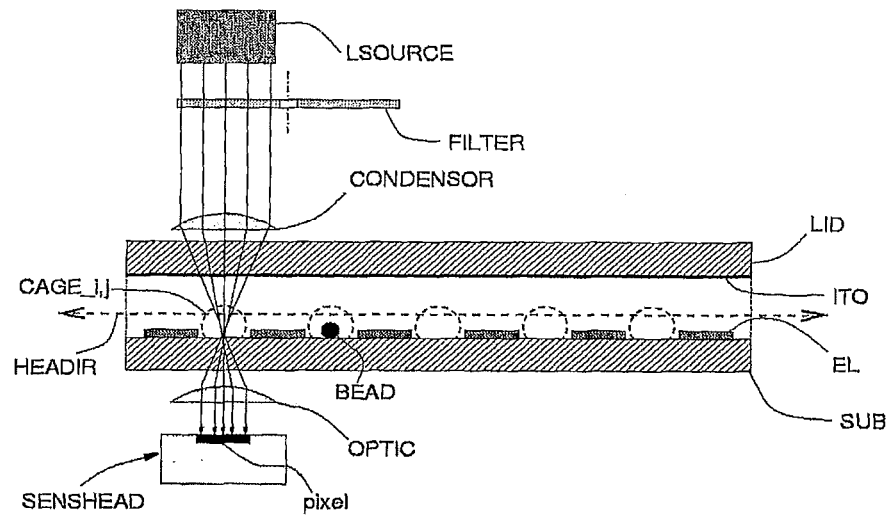
FIG. 48 shows an apparatus for the manipulation and detection and/or identification of particles by means of optical sensors in which the measurement is made by measuring portions of the array in time sequence.

Shown in FIG. 48 purely by way of example that in no way limits the scope of the present invention is a possible embodiment of this idea. In this case, it is the device that moves, whilst the sensor (SENSHEAD), the light condenser (CONDENSOR), the precision optics (OPTIC), possible filters (FILTER) and the light source (LSOURCE) remain fixed.

Finally, it is possible to use a single photosensitive element to carry out a scan in time sequence of the entire array. In this case, after each acquisition, a displacement of the sensor (SENSHEAD) is effected in the direction parallel to the rows, by a distance equal to the pitch between elements of the row. Next, at the end of each row a displacement of the sensor is effected in the direction parallel to the columns, by a distance equal to the pitch between elements of the column. Then a further row is scanned, proceeding in the same manner up to completion of the entire array.

Finally, it is evident that the acquisition method and/or apparatuses described previously can be applied to all of the methods and/or apparatuses forming the subject of the present invention, which is particularly useful when the use of sensors is combined with the manipulation of particles or cells.

Aspects of the Disclosure

Aspect 1. A method for the manipulation of particles (BEAD) by means of an at least two-dimensional array of groups (BLOCK_i,j) of electrodes, comprising the steps of:

i. generating a first configuration of field of force (F_i), which presents at least one first point (CAGE_i,j) and at least one second point (CAGE_i,j+1) of stable equilibrium for said particles (BEAD), said points being positioned, respectively, on a first group (BLOCK_i,j) and on a second group (BLOCK_i,j+1) of said array immediately adjacent to the first, and being such that at least one particle (BEAD) is entrapped in said first point of stable equilibrium (CAGE_i,j);

ii. generating at least one second configuration of field of force (F_ii) such that a particle (BEAD) is pushed within a basin of attraction of said at least one second point of stable equilibrium (CAGE_i,j+1); and iii. generating again said first configuration of field of force (F_i), such that said particle (BEAD) is attracted towards the second point of stable equilibrium (CAGE_i,j+1); said method being characterized in that said first configuration (F_i) and said second configuration (F_ii) of field of force are generated by means of at least two different configurations of first voltages (Vrow_i[p] and Vcol_j[q]) applied to the electrodes of the first group of the array (BLOCK_i, j) and of second voltages (Vrow_i[p] and Vcol_j+1[q]) applied to the electrodes of the second group of the array (BLOCK_i,j+1).

Aspect 2. The method according to aspect 1, comprising an iterative execution of steps i) to iii) on a plurality of said groups of electrodes of said array arranged adjacent to one another two by two so as to displace at least one particle (BEAD) present in at least one of said groups of electrodes (BLOCK_i,j) along paths constituted by a succession of said adjacent groups of electrodes.

Aspect 3. The method according to aspect 1, characterized in that each group of electrodes (BLOCK_i,j) of the array is constituted by: at least one first set of electrodes connected to voltages (Vphip, Vphin) by means of row signals (Vrow_i[p]); at least one second set of electrodes connected to voltages (Vphip, Vphin) by means of column signals (Vcol_j[q]); and at least one electrode connected to voltages (Vphip, Vphin) by means of a signal (Vcore) common to all the groups of electrodes of the array and such that each pair of adjacent groups of electrodes (BLOCK_i,j and BLOCK_i,j+1) can assume said at least one second configuration of field of force (F_ii) whilst all the other groups of electrodes of the array maintain said first configuration (F_i), by means of modification of the voltages applied via said row signals (Vrow_i[p]) and column signals (Vcol_j[q]) connected to said pair of adjacent groups (BLOCK_i,j and BLOCK_i, j+1) of electrodes.

Aspect 4. The method according to aspect 1, characterized in that each group of electrodes (BLOCK_i,j) of the array is constituted by at least one first set of electrodes connected to voltages (Vphip, Vphin) by means of electronic circuits (MUX_i,j and AND_i,j) controlled by means of a first set of digital row signals (row_i) and column signals (col_j) and by at least one electrode connected to voltages (Vphip, Vphin) by means of a second set of signals (Vcore) common to all the groups of electrodes (BLOCK_i,j) of the array such that each pair of adjacent groups of electrodes (BLOCK_i,j and BLOCK_i,j+1) can assume said second configuration of field of force (F ii) whilst all the other groups of electrodes of the array maintain said first configuration (F_i), by means of modification of the voltages applied to said pair of adjacent groups (BLOCK_i,j and BLOCK_i,j+1) of electrodes via said first set of row signals (row_i) and column signals (col_j), which are connected to the electronic circuits (MUX_i,j and AND_i,j) of said groups (BLOCK_i,j and BLOCK_i,j+1) of electrodes.

Aspect 5. A method for the manipulation of particles (BEAD) by means of an array of first groups of electrodes that form at least one lane (C_STORE; VRCHJ), comprising the steps of:

i. generating a first configuration of field of force designed to create at least one point of stable equilibrium (CAGE_i, j) for said particles (BEAD), said point being positioned on at least one lane (C_STORE; VRCHJ) and being such that at least one particle (BEAD) is entrapped in said at least one point of stable equilibrium (CAGE_i,j); and ii. displacing by one or more positions, each defined by at least one electrode or by a first group of electrodes, all of said points of stable equilibrium previously generated along said at least one lane (C_STORE; VRCHJ);

said method being characterized in that the points of stable equilibrium present on said lanes are generated and moved by means of the application to the electrodes of the first groups of electrodes forming said at least one lane (C_STORE; VRCHJ) of at least three different configurations of voltages (V1_j, V2_j, V3_j).

Aspect 6. The method according to aspect 5, characterized in that it envisages manipulation of said particles (BEAD) by means of a plurality of lanes and by means of second groups of electrodes of said array that form parking cells (BLOCK_i,j) arranged alongside one another and/or alongside said lanes, said method comprising the steps of:

i. generating a second configuration of field of force designed to create at least one point of stable equilibrium (CAGE_i,j) for said particles (BEAD), which is positioned on a parking cell (BLOCK_i,j) and is such that at least one particle (BEAD) is entrapped in said at least one point of stable equilibrium (CAGE_i,j);

ii. generating a third configuration of field of force such that a particle (BEAD) entrapped in a parking cell (BLOCK_i, j) can be pushed into a basin of attraction of a point of stable equilibrium adjacent to the parking cell and formed by means of the electrodes of said lanes (VRCHJ); and iii. displacing by one or more positions all the points of stable equilibrium present in said lanes (VRCHJ) along them;

where the points of stable equilibrium of said lanes are generated and moved by means of at least three different configurations of voltages (V1_j, V2_j, V3_j) applied to the electrodes of said lanes (VRCHJ); and in which the different field configurations for pushing a particle (BEAD) from the point of stable equilibrium of one parking cell (BLOCK_i,j) to one of the points of stable equilibrium of the lanes (VRCHJ) or vice versa are generated by means of row voltages (Vrow_i) and column voltages (Vcol_j and Vcage_j) applied to the electrodes of the second groups (BLOCK_i,j) and by means of voltages (V1_j, V2_j, V3_j) applied to the electrodes of the first groups of electrodes forming said lanes (VRCHJ).

Aspect 7. The method according to aspect 6, comprising the further step of: generating a fourth configuration of field of force such that a said particle (BEAD) can be pushed from a lane into a basin of attraction (CAGE_i+1) of a point of stable equilibrium belonging to a parking cell (BLOCK_i+1,j) different from the one in which said particle was before being displaced on the lane.

Aspect 8. The method according to aspect 7, characterized in that said movements of points of stable equilibrium and said field configurations necessary for pushing the particle (BEAD) from the point of stable equilibrium of a parking cell (BLOCK_i,j) to one of the points of stable equilibrium of the lanes (VRCHJ) and vice versa act on any number of particles simultaneously, to displace each particle along a different path.

Aspect 9. The method according to aspect 5, characterized in that for the manipulation of said particles (BEAD) by means of said array of first groups of electrodes, the latter are pre-arranged for providing at least two lanes (C_STORE and C_TEMP); and in that it comprises the steps of:

i. generating at least one point of stable equilibrium (CAGE_i,j) for said particles (BEAD), which is positioned on at least one first lane (C_STORE) and is such that at least one particle (BEAD) is entrapped in said at least one point of stable equilibrium (CAGE_i,j);

ii. displacing by one or more positions all the points of stable equilibrium along one or more lanes (C_STORE) so that said at least one point of stable equilibrium (CAGE_i,j) can be shared by at least one second lane (C_TEMP); and iii. displacing by one or more positions all the points of stable equilibrium along one or more lanes (C_STORE) so that said particle (BEAD) is entrapped in at least one point of stable equilibrium (CAGE_i,j) belonging to said at least one second lane (C_TEMP); in which said points of stable equilibrium of said lanes are generated and moved by applying to the electrodes of said first groups of electrodes of the array at least three different configurations of voltages (V1_j, V2_j, V3_j) for each of said lanes.

Aspect 10. The method according to aspect 1, characterized in that it comprises, in sequence, a plurality of steps of entrapping of said particles in points of stable equilibrium and of displacement of said points of stable equilibrium combined in such a way as to select one or more particles (BEAD).

Aspect 11. The method according to aspect 1, characterized in that it comprises, in sequence, a plurality of steps of entrapping of said particles in points of stable equilibrium and of displacement of said points of stable equilibrium combined in such a way as to reorder the arrangement of two or more particles (BEAD).

Aspect 12. The method according to aspect 1, characterized in that it comprises, in sequence, a plurality of steps of entrapping of said particles in points of stable equilibrium and of displacement of said points of stable equilibrium combined in such a way as to displace one or more particles (BEAD) present on one and the same group of electrodes (BLOCK_i,j).

Aspect 13. The method according to aspect 1, characterized in that it comprises, in sequence, a plurality of steps of entrapping of said particles in points of stable equilibrium and of displacement of said points of stable equilibrium combined in such a way as to separate and/or move away two or more particles (BEAD) positioned on one and the same group of electrodes (BLOCK_i,j) towards at least two different positions.

Aspect 14. The method according to aspect 1, characterized in that said field of force (F) comprises at least one of the following forces:

i. positive dielectrophoresis (PDEP);
ii. negative dielectrophoresis (NDEP);
iii. electrophoresis (EF);
iv. electrohydrodynamic flows (EHD); and
v. electrowetting on dielectric (EWOD)

Aspect 15. A method for detection and/or characterization and/or quantification and/or recognition of cells or particles (BEAD) in aqueous suspension or aggregated in tissues comprising a measurement of impedance between at least one first electrode connected to at least one first row signal and at least one second electrode adjacent to said first electrode, said second electrode being connected to at least one first column signal, said method being characterized in that said measurement between said at least two adjacent electrodes is made by evaluating the impedance between said first row signal and said first column signal.

Aspect 16. The method according to aspect, 15 characterized in that it is carried out further a detection and/or characterization and/or quantification and/or recognition of cells or particles (BEAD) in aqueous suspension comprising a measurement of impedance between at least one first electrode connected to at least one first row signal and at least one second electrode adjacent to said first electrode, said second electrode being connected to at least one first column signal, said method being characterized in that said measurement between said at least two adjacent electrodes is made by evaluating the impedance between said first row signal and said first column signal.

Aspect 17. An apparatus for the manipulation of particles (BEAD), characterized in that it comprises:

i. an array of electrodes forming an array of blocks of groups (BLOCK_i,j) of electrodes arranged in rows and columns, each block comprising: a first group of electrodes connected to column signals (Vcol_j[q]) common to all the first groups of the same column of blocks; a second group of electrodes connected to row signals (Vrow_i[p]) common to all the second groups of the same row of blocks; and a third group of electrodes connected to signals common to all the blocks of groups of electrodes (BLOCK_i,j) of the array of electrodes;

ii. means for generating at least two different voltages (Vphin, Vphip); and iii. means for distributing said voltages (Vphin, Vphip) to said row signals (Vrow_i[p]) and to said column signals (Vcol_j[q]) and to said common signals;

in which said means for distributing said voltages (Vphin, Vphip) are such that for each pair formed by a first block (BLOCK_i,j) of groups of electrodes and by a second block (BLOCK_i,j+1) of groups of electrodes adjacent to the first block, at least one first configuration (F_i) and one second configuration (F_ii) of field of force are generated obtained by applying two different configurations of said two voltages (Vphin, Vphip) to the row signals (Vrow_i[p]) and column signals (Vcol_j[q] and Vcol_j+1[q]); said first configuration (F_i) of field of force being designed to create at least one first point (CAGE_i,j) and at least one second point (CAGE_i,j+1) of stable equilibrium for said particles (BEAD), said points being positioned, respectively, on said first block (BLOCK_i,j) and on said second block (BLOCK_i,j+1) of groups of electrodes of the array; and said second configuration (F_ii) of field of force being designed to push said particle (BEAD) possibly entrapped in said first point of stable equilibrium (CAGE_i,j) into a basin of attraction of said at least one second point of stable equilibrium (CAGE_i,j+1).

Aspect 18. The apparatus according to aspect 17, characterized in that said first group of electrodes of each said block (BLOCK_i,j) comprises at least one first electrode (ring_i,j_1) connected to a column signal (Vcol_j) common to all the groups of the same column; said second group of electrodes of each block comprises at least one second electrode (ring_i,j_2) connected to a row signal (Vrow_i) common to all the groups of the same row; and said third group of electrodes of each block comprises at least one third electrode (EL_i,j) connected to a common signal (Vcore), in which said third electrode (EL_i,j) is surrounded by said first electrode (ring_i,j_1) and said third electrode (EL_i,j) and said first electrode (ring_i,j_1) are surrounded by said second electrode (ring_i,j_2);

Aspect 19. The apparatus according to aspect 17, characterized in that said first group of electrodes of each said block (BLOCK_i,j) comprises at least one first electrode (elle_j) connected to a column signal (Venable_j) common to all the groups of the same column; said second group of electrodes of each block comprises at least one second electrode (wallx_i) connected to a row signal (Vrow_i[x]) common to all the groups of the same row; and said third group of electrodes of each block comprises at least one third electrode (EL_i,j) connected to a common signal (Vcore); in which said second group of electrodes of each block moreover comprises at least one fourth electrode (wally_i) connected to a row signal (Vrow_i[y]) common to all the groups of the same row; and where said third electrode (EL_i,j) is flanked in two directions adjacent by said first electrode (elle_j), and said first electrode (elle_j) is flanked by said second electrode (wallx_i) and said fourth electrode (wally_i).

Aspect 20. The apparatus according to aspect 17, characterized in that said first group of electrodes of each said block (BLOCK_i,j) is distinguished into electrodes with even column index and odd column index, whilst said second group of electrodes of each said block (BLOCK_i, j) is distinguished into electrodes with even row index and odd row index; in which said third group of each block comprises at least one third electrode (EL_i,j) connected to a common signal (Vcore); and in which said first group comprises at least one first electrode connected to a column signal (Vcol_i[D1]) common to the blocks of the same column with even column index or to a column signal (Vcol_i[D2]) common to the blocks of the same column with odd column index; and at least one second electrode connected to a column signal (Vcol_i[U1]) common to the blocks of the same column with even column index or to a column signal (Vcol_i[U2]) common to the blocks of the same column with odd column index; and in which said second group comprises at least one fourth electrode connected to a row signal (Vrow_i [R1]) common to the blocks of the same row with even row index or to a row signal (Vrow_i[R2]) common to the blocks of the same row with odd row index and at least a fifth electrode connected to a row signal (Vrow_i[L1]) common to the blocks of the same row with even row index or to a row signal (Vrow_i[L2]) common to the blocks of the same row with odd row index.

Aspect 21. An apparatus for the manipulation of particles (BEAD), comprising:

i. an array of electrodes forming an array of blocks of groups (BLOCK_i,j) of electrodes arranged in rows and columns, each block comprising: a first group of at least one first electrode (EL_i,j) connected to a signal common to all the blocks; and a second group of at least one second electrode (ring_i,j) connected to an output signal of a circuit (MUX_i,j), driven by at least one second circuit (AND_i, j);

ii. means for generating at least two different voltages (Vphin, Vphip); and iii. means generating row signals (row_i) common to all the blocks (BLOCK_i,j) of the same row and column signals (col_j) common to all the blocks (BLOCK_i,j) of the same column for driving said circuits (AND_i,j) and by means of which the voltage (Vphin, Vphip) to connect to said at least one second electrode (ring_i,j) of each block (BLOCK_i,j) is selected;

where for each pair formed by a first block (BLOCK_i,j) and a second block (BLOCK_i,j+1) adjacent to the first block said means for generation of signals determine the creation of at least one first configuration (F_i) and one second configuration (F_ii) of field of force by applying two different configurations of values to the row signals (Vrow_i) and column signals (Vcol_j and Vcol_j+1) such that said first configuration (F_i) of field of force presents at least one first point (CAGE_i,j) of stable equilibrium and at least one second point (CAGE_i,j+1) of stable equilibrium for said particles (BEAD), said points being positioned, respectively, on said first block (BLOCK_i,j)

and on said second block (BLOCK_i,j+1) of the array, and being such that said second configuration (F_ii) of field of force is designed to push said particle (BEAD) that is possibly entrapped in said first point of stable equilibrium (CAGE_i,j) into a basin of attraction of said at least one second point of stable equilibrium (CAGE_i,j+1).

Aspect 22. The apparatus according to aspect 21, characterized in that said first group of electrodes of each said block (BLOCK_i,j) comprises at least one first electrode (EL_i,j) connected to a signal common to all the blocks constituted by one (Vphin) of said different voltages; and in that said second group of electrodes comprises at least one second electrode (ring_i,j) connected to the output signal of a circuit that constitutes a deviator (MUX_i,j), such that just one of two different signals (Vphin, Vphip) at input to the deviator can be connected at output from the deviator according to the value of the output signal of a further circuit (AND_i,j), which performs a logic function between the values of the row signals (row_i) and column signals (col_j); and in which said first electrode (EL_i,j) is surrounded by said second electrode (ring_i,j).

Aspect 23. An apparatus for the manipulation of particles (BEAD), comprising:
i. an array of electrodes comprising first groups of electrodes, each of which is constituted by at least one first electrode connected to a first signal (V1_j; S1), by at least one second electrode connected to a second signal (V2_j; S2) and by at least one third electrode connected to a third signal (V3_j; S3) such that the set of said first groups of electrodes forms at least one first lane (VRCHJ; C_STORE), designed to move said particles (BEAD) in a chosen direction;
ii. means for generating at least two different voltages (Vphin, Vphip); and
iii. means for distributing said voltages (Vphin, Vphip) to said at least one first signal (V1_j; S1), second signal (V2_j; S2) and third signal (V3_j; S2);
so that each lane (VRCHJ; C_STORE) can generate at least one first configuration (F_i) of field of force designed to create at least one first point of stable equilibrium (CAGE_i,j) for said particles (BEAD), which is positioned on said at least one first lane (VRCHJ; C_STORE) and is such that at least one particle (BEAD) is entrapped in said at least one point of stable equilibrium (CAGE_i,j) and can be displaced along said first lane (VRCHJ; C_STORE), simultaneously displacing all of said first points of stable equilibrium present on the first lane by applying to the electrodes of said first groups of electrodes at least three different configurations of voltages on said signals (V1_j, V2_j, V3_j; S1, S2, S3).

Aspect 24. The apparatus according to aspect 23, characterized in that said array of electrodes moreover comprises an array of blocks (BLOCK_i,j) of groups of electrodes arranged in rows and columns for the manipulation of said particles (BEAD), each block (BLOCK_i,j) of the array comprising:
i. a second group of electrodes of said array connected to column signals (Vcage_j, Vcol_j) common to all the blocks (BLOCK_i,j) of the same column;
ii. a third group of electrodes of said array connected to row signals (Vrow_i) common to all the groups of the same row; and
iii. and a fourth group of electrodes of said array connected to signals (Vp_j) common to all the blocks (BLOCK_i,j);
such that each block (BLOCK_i,j) can constitute a parking cell (CAGE_i,j) for said particles arranged alongside one another and/or alongside said at least one first lane;

said apparatus comprising moreover means for distributing said voltages (Vphin, Vphip) to said row signals (Vrow_i) and to said column signals (Vcage_j, Vcol_j) and to said common signals (Vp_j) so that each block (BLOCK_i,j) of the array can generate at least one first configuration (F_i) and one second configuration (F_ii) of field of force by applying two different configurations of voltages (Vphin, Vphip) to the row signals (Vrow_i) and column signals (Vcage_j, Vcol_j) such that said first configuration (F_i) of field of force presents at least one second point of stable equilibrium (CAGE_i,j) for said particles (BEAD) positioned on said block (BLOCK_i,j) and such that said second configuration (F_ii) of field of force pushes said particle (BEAD) into a basin of attraction of said at least one first point of stable equilibrium formed by means of the electrodes of said at least one first lane (VRCHJ) and displaceable along said lane (VRCH_j).

Aspect 25. The apparatus according to aspect 24, characterized in that said means for distributing said voltages (Vphin, Vphip) to said row signals (Vrow_i) and/or to said column signals (Vcage_j, Vcol_j) and/or to said common signals (Vp_j) are constituted by signal-conditioning circuits and/or memory elements.

Aspect 26. The apparatus according to aspect 25, characterized in that said means for distributing said voltages (Vphin, Vphip) to said at least one first signal (V1_j), one second signal (V2_j), and one third signal (V3_j) are constituted by signal-conditioning circuits and/or memory elements.

Aspect 27. The apparatus according to aspect 23, characterized in that said array of electrodes moreover comprises:
i. second groups of electrodes, each of which is constituted by at least one first electrode connected to a fourth signal (T1), by at least one second electrode connected to a fifth signal (T2), and by at least one third electrode connected to a sixth signal (T3) such that the set of said second groups of electrodes forms at least one second lane (C_TMP), designed to move said particles (BEAD) in a chosen direction;
ii. at least one point of exchange formed by means of adjacent electrodes belonging to said first and, respectively, said second at least one lane; and
iii. means for distributing said voltages (Vphin, Vphip) to said at least one fourth signal (T1), fifth signal (T2) and sixth signal (T3);
so that each at least one first and second lanes (C_STORE and C_TEMP) is designed to generate selectively at least one first configuration (F_i) and one second configuration (F_ii) of field of force such that said first configuration (F_i) of field of force presents at least one first and one second point of stable equilibrium on said first and second lane (C_STORE or C_TEMP), respectively, said points being such that at least one particle (BEAD) is entrapped in said at least one first or second point of stable equilibrium and can be displaced along said lanes (C_STORE or C_TEMP), simultaneously displacing all of said first or second points of stable equilibrium present on the first or second lane by applying to the electrodes of said first and second groups of electrodes at least three different configurations of voltages on said signals (S1 and/or S2 and/or S3 and/or T1 and/or T2 and/or T3) and such that said second configuration (F_ii) of field of force is formed at said point of exchange and is designed to push said particle (BEAD) into a basin of attraction of said at least one second point of stable equilibrium obtained by means of the electrodes of the second lane (C_TEMP).

Aspect 28. The apparatus according to aspect 27, characterized in that it comprises at least one first microchamber (MCH) comprising: one or more first lanes (VC_1), driven by at least three voltages (V1, V2 and V3), and at least one second (HCONV) lane, driven by at least three signals (H1, H2 and H3) with at least one first point of exchange between said first lane (VC_1) and said second lane (HCONV); and at least one second microchamber (RCH); characterized in that it comprises at least one third lane (RCONV), driven by at least three signals (R1, R2 and R3) and at least one second point of exchange between said second lane (HCONV) and said third lane (RCONV) such that it is possible to bring a particle from said first microchamber (MCH) into said second microchamber (RCH) through a said first (VC_1) and said second lane (HCONV), and said at least one first and at least one second point of exchange.

Aspect 29. The apparatus according to aspect 27, characterized in that it comprises at least one first microchamber (MCH) comprising at least one first lane (VC_1), driven by at least three signals (V1, V2 and V3) and at least one second (HCONV) lane driven by at least three signals (H1, H2 and H3) with a first point of exchange between said first lane (VC_1) and said second lane (HCONV), and at least one second microchamber (RCH); characterized in that it comprises at least one third lane (RCONV) synchronous with said first lane and driven by said at least three signals (V1, V2 and V3) and at least one second point of exchange between said second lane (HCONV) and said third lane (RCONV) obtained by means of an electrode driven by a signal (THR) such that it is possible to bring a particle from said first microchamber (MCH) into said second microchamber (RCH) through said first lane (VC_1) and said second lane (HCONV) and said first and said second points of exchange.

Aspect 30. The apparatus according to aspect 27, characterized in that said means for distributing said voltages (Vphin, Vphip) to said signals are obtained by means of signal-conditioning circuits and/or memory elements.

Aspect 31. The apparatus according to aspect 27, characterized in that it is divided by a diaphragm (CHW) made of polymeric material into two microchambers (MCH, RCH), a first microchamber (MCH) comprising:
a. a first multiplicity and a second multiplicity of lanes forming a vertical closed loop (VC1_1 ... VC1_NCV and VC2_1 ... VC2_NCV), designed to form each a plurality (NI) of said points of stable equilibrium (CAGES) for entrapping said particles (BEAD), by means of three phases (V1, V2 and V3), connected repeatedly at respective iterations (I_1 ... I_NI) of groups of three electrodes on each lane;
b. a first horizontal lane and a second horizontal lane (HCONV_UP, HCONV_DOWN), respectively, an upper one and a lower one, driven by four phases (H1, H2, H3 and H4) and comprising a plurality (NCV) of points of exchange with the vertical lanes, active in one of said phases (V2+H3), so that it will be possible to transfer simultaneously the contents of at least one point of stable equilibrium from the vertical lanes to the first horizontal lane or second horizontal lane;
c. a third horizontal lane (HCONV_AUX), driven by four phases (AUX1, AUX2, AUX3 and AUX4), which comprises a plurality (NCAUX1) of points of exchange with the upper horizontal lane (HCONV_UP) and an identical number (NCAUX2) of points of exchange with the lower horizontal lane (HCONV_DOWN), situated in positions corresponding to one another;
d. a completely programmable array of electrodes designed to form in use an array of individually programmable attraction cages for said particles defined by points of stable equilibrium of a field of force generated via said electrodes;
e. a first vertical dump lane and a second vertical dump lane (VCW_UP and VCW_DOWN), driven by three phases in a way substantially similar to said vertical lanes (VC1_i and VC2_j), which have the function of removing undesired particles from the array; and
f. a vertical long dump lane (VCW_LONG), having a dimension approximately twice that of the other said vertical lanes (VC1_i and VC2_j) set in a portion of said first microchamber (MCH) situated on the opposite side with respect to the array.

Aspect 32. The apparatus according to aspect 31, characterized in that said second microchamber (RCH) comprises: an exit lane (RCONV), driven by four phases (R1, R2, R3 and R4), for conveying particles of interest leaving said array into the second microchamber, through a discontinuity of said diaphragm made of polymeric material (CHW) constituting a passage of communication between the two microchambers; and a horizontal feedback lane (HCONV_FB), driven by four phases (FB1, FB2, FB3 and FB4), lying substantially on one and the same straight line identified by said auxiliary horizontal lane, by means of which it is possible to bring a particle back from the exit lane (RCONV), and hence from the second microchamber (RCH), into the array, once again through the aforesaid passage in the diaphragm (CHW).

Aspect 33. The apparatus according to aspect 17, characterized in that it comprises at least two microchambers and in that it presents an arrangement of said electrodes of said array of electrodes such that it is possible to displace said particles (BEAD) from one microchamber to the other and vice versa by driving said electrodes with appropriate signals.

Aspect 34. The apparatus according to aspect 17, characterized in that said electrodes are made on a substantially planar substrate (SUB); and in that it comprises a further electrode (ITO) made on a further substrate (LID) set at a distance from and facing said first substrate (SUB), said further electrode (ITO) being electrically connected to a further electrical signal.

Aspect 35. An apparatus for detection and/or characterization and/or quantification and/or recognition of cells or particles (BEAD) in aqueous suspension or aggregated in tissues, comprising:
i. an array of groups of electrodes comprising a first group of electrodes connected to column signals (Cj) common to all the groups of the same column and at least one second group of electrodes connected to row signals (R1) common to all the groups of the same row;
ii. means for generating at least one voltage (Vin);
iii. at least one circuit for reading the impedance (Zcage_i,j) given by the intersection of a row (Ri) and a column (Cj); and
iv. means (MRi) for distributing said voltage (Vin) to said row signals (R1) and means (MCj) for distributing said column signals (Cj) to said at least one read circuit;
in which by connecting said read circuit to a column (Cj) and by applying said voltage to a row, (Ri) the output signal (Vout and/or out) of said read circuit is affected by the value of the impedance (Zcage_ij) between that column and that row.

Aspect 36. The apparatus according to aspect 35, characterized in comprising means for reading the variation of impedance at one or more potential holes (CAGE) due to the presence of one or more particles (BEAD).

Aspect 37. The apparatus according to aspect 36, characterized in that said means for reading the variation of impedance are obtained by means of row signals (R1) and column signals (Cj) such that at least one or more particles (BEAD) alter the value of impedance due to the intersection between at least one row (Ri) and at least one column (Cj).

Aspect 38. The apparatus according to aspect 37, characterized in that said column signals (Cj) are obtained on a first substantially planar substrate (SUB) and in that said row signals (R1) are obtained on a further substrate (LID) set at a distance from and facing said first substrate (SUB).

Aspect 39. The apparatus according to aspect 36, characterized in that said means for reading the variation of impedance are obtained by means of the same signals used for the creation of the distributions of said fields of force (F).

Aspect 40. An apparatus for the manipulation of particles (BEAD) comprising:
i. means for generating at least one voltage (Vphin); and
ii. at least one electrode (EL) connected to said electrical signal (Vphin);
said apparatus being characterized in that said at least one electrode comprises holes such as to form a grid and, as a consequence of the application of said electrical signal to said electrode, points of stable equilibrium (CAGE_i,j) for said particles (BEAD).

Aspect 41. The apparatus for the manipulation and detection and/or identification of particles (BEAD) according to aspect 40, characterized in that it comprises means for reading the variation in intensity of a light (LIGHT) reflected and/or transmitted to one or more of said points of stable equilibrium due to the presence of one or more particles (BEAD) entrapped therein.

Aspect 42. The apparatus according to aspect 41, characterized in that said means for reading the variation in intensity of the reflected and/or transmitted light comprise an array of one or more optical sensors (pixel) arranged on a mobile head (SENSHEAD) and separate from the substrate (SUB) such that reading of the variation of reflected and/or transmitted light (LIGHT) at each point of equilibrium can be obtained by aligning said head with respect to said point of equilibrium by means of a relative motion between head and substrate.

Aspect 43. The apparatus according to aspect 41, characterized in that said means for reading the variation of the intensity of the light reflected and/or transmitted comprise an array of one or more optical sensors (pixel) integrated within said substrate (SUB).

Aspect 44. The apparatus according to aspect 41, characterized in that said means for reading the variation in intensity of the light comprise an array of one or more external optical sensors (pixel) positioned in a further substrate (OPTISENS) set underneath said first substrate (SUB) or on top of said second substrate (LID).

Aspect 45. The apparatus according to aspect 43, characterized in that it comprises an array of lenses (MICROLENSES), each of which concentrates the incident light in a position corresponding to each electrode or group of electrodes (BLOCK_i,j) in which a said point of stable equilibrium (CAGE_i,j) for said particles (BEAD) can be provided.

The invention claimed is:

1. A method for detection and/or characterization and/or quantification and/or recognition of cells or particles (BEAD) in aqueous suspension or aggregated in tissues comprising: measuring impedance between at least one first electrode connected to at least one first row signal and at least one second electrode diagonally adjacent to said first electrode, said second electrode being connected to at least one first column signal, said method being characterized in that said measurement between said at least two diagonally adjacent electrodes is made by evaluating the impedance given by a diagonal intersection of said first row signal and said first column signal.

2. The method according to claim 1, further comprising the step of carrying out a detection and/or characterization and/or quantification and/or recognition of cells or particles in aqueous suspension using the measurement of impedance between at least one first electrode connected to at least one first row signal and at least one second electrode diagonally adjacent to said first electrode, said second electrode being connected to at least one first column signal, wherein said measurement between said at least two adjacent electrodes is made by evaluating the impedance given by a diagonal intersection of said first row signal and said first column signal.

3. An apparatus for detection and/or characterization and/or quantification and/or recognition of cells or particles (BEAD) in aqueous suspension or aggregated in tissues, comprising:
i. an array of groups of electrodes comprising a first group of electrodes aligned in columns and connected to column signals (Cj) common to all the groups of the same column and at least one second group of electrodes aligned in rows and connected to row signals (R1) common to all the groups of the same row;
ii. at least one circuit for reading the impedance (Zcage_i,j) given by an diagonal intersection of a row signal (Ri) and a column signal (Cj); and
iii. a first signal-conditioning circuit (MRi) for distributing at least one voltage (Vin) to said row signals (Ri) and a second signal-conditioning circuit (MCj) for distributing said column signals (Cj) to said at least one read circuit; wherein
iv. said read circuit is configured to generate an output signal (Vout and/or out) which is affected by the value of the impedance (Zcage_ij) between a column (Cj) connected to said read circuit and a row (Ri) to which said voltage is applied.

4. The apparatus according to claim 3, further comprising a circuit for reading the variation of impedance at one or more potential holes (CAGE) due to the presence of one or more particles (BEAD).

5. The apparatus according to claim 4, wherein said circuit for reading the variation of impedance at one or more potential holes is configured such that at least one or more particles (BEAD) alter the value of impedance due to the diagonal intersection between at least one row (Ri) and at least one column (Cj) to which row signals (Ri) and column signals (Cj) are applied.

6. The apparatus according to claim 4, characterized in that said circuit for reading the variation of impedance is configured to receive the same signals used for the creation of the distributions of said fields of force (F).

7. The apparatus according to claim 3, wherein the first signal-conditioning circuit and/or the second signal conditioning circuit form a multiplexer.

8. An apparatus for detection and/or characterization and/or quantification and/or recognition of cells or particles (BEAD) in aqueous suspension or aggregated in tissues, comprising:

i. an array of groups of electrodes comprising a first group of electrodes aligned in columns and connected to column signals (Cj) common to all the groups of the same column and at least one second group of electrodes aligned in rows and connected to row signals (R1) common to all the groups of the same row;

ii. at least one circuit for reading the impedance (Zcage_i, j) given by an intersection of a row (Ri) and a column (Cj); and iii. a first signal-conditioning circuit (MRi) for distributing at least one voltage (Vin) to said row signals (Ri) and a second signal-conditioning circuit (MCj) for distributing said column signals (Cj) to said at least one read circuit; wherein iv. said read circuit is configured to generate an output signal (Vout and/or out) which is affected by the value of the impedance (Zcage_ij) between a column (Cj) connected to said read circuit and at row (Ri) to which said voltage is applied; and v. said column signals (Cj) are obtained on a first substantially planar substrate (SUB) and said row signals (Ri) are obtained on a further substrate (LID) set at a distance from and facing said first substrate (SUB).

* * * * *

UNITED STATES PATENT AND TRADEMARK OFFICE
CERTIFICATE OF CORRECTION

PATENT NO.          : 9,719,960 B2
APPLICATION NO.     : 14/159725
DATED               : August 1, 2017
INVENTOR(S)         : Gianni Medoro et al.

It is certified that error appears in the above-identified patent and that said Letters Patent is hereby corrected as shown below:

In the Drawings

Sheet 19, Fig. 32, "anello" should be -- ring --; "matrice" should be -- array --.

Sheet 20, Fig. 33, each instance of "Fase" should be -- Phase --; "speciale" should be -- special --; "positiva" should be -- positive --; "gruppo" should be -- group --; "elemento" should be -- element --.

Figure 34:
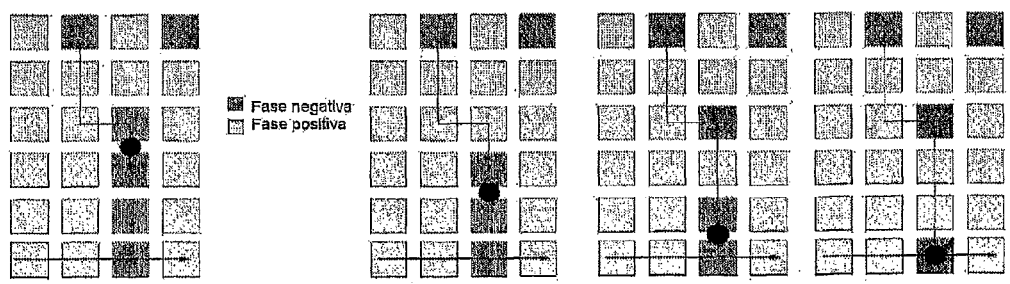
FIG. 34 shows the sequence of steps necessary for exchange of a particle between a vertical lane of a certain group and element and a horizontal lane of the apparatus for the manipulation of particles of FIG. 32.

Sheet 20, Fig. 34, "fase negativa" should be -- phase negative --; "fase positiva" should be -- phase positive --.

Sheet 21, Fig. 35, "fase negativa" should be -- phase negative --; "fase positiva" should be -- phase positive --.

Sheet 21, Fig. 36, "matrice" should be -- array --; each instance of "Fase" should be -- Phase --; "speciale" should be -- special --; "elemento" should be -- element --; "gruppo" should be -- group --; each instance of "punto di scambio" should be -- point of exchange --.

Sheet 22, Fig. 37, "fase negativa" should be -- phase negative --; "fase positiva" should be -- phase positive --.

Sheet 22, Fig. 38, each instance of "Fase" should be -- Phase --; "positiva" should be -- positive --; each instance of "speciale" should be -- special --; "orizz." should be -- hor. --; each instance of "gruppo" should be -- group --; each instance of "elemento" should be -- element --; each instance of "scambio" should be -- Exchange --.

Sheet 23, Fig. 39, each instance of "Fase" should be -- Phase --; "punto di scambio" should be -- point of exchange --; "positiva" should be -- positive --.

Figure 40:
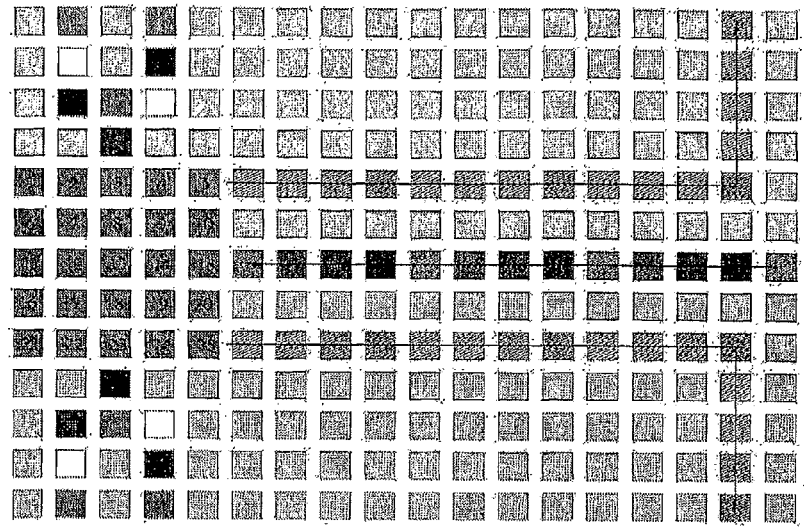
FIG. 40 shows the exchange gate for the passage of a particle from the completely programmable matrix array to the exit lane.

Sheet 24, Fig. 40, "matrice" should be -- array --; each instance of "Fase" should be -- Phase --; "positiva" should be -- positive --.

Signed and Sealed this
Twenty-fourth Day of April, 2018

Andrei Iancu
*Director of the United States Patent and Trademark Office*

Figure 41:
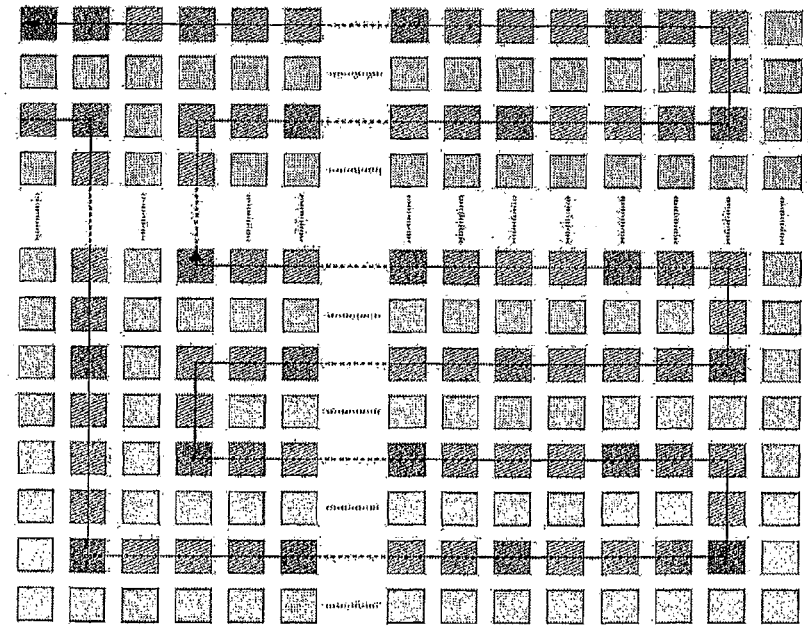
FIG. 41 shows the exit lane of the apparatus for the manipulation of particles of FIG. 32.

Sheet 24, Fig. 41, each instance of "Fase" should be -- Phase --; "positiva" should be -- positive --.

Figure 42:
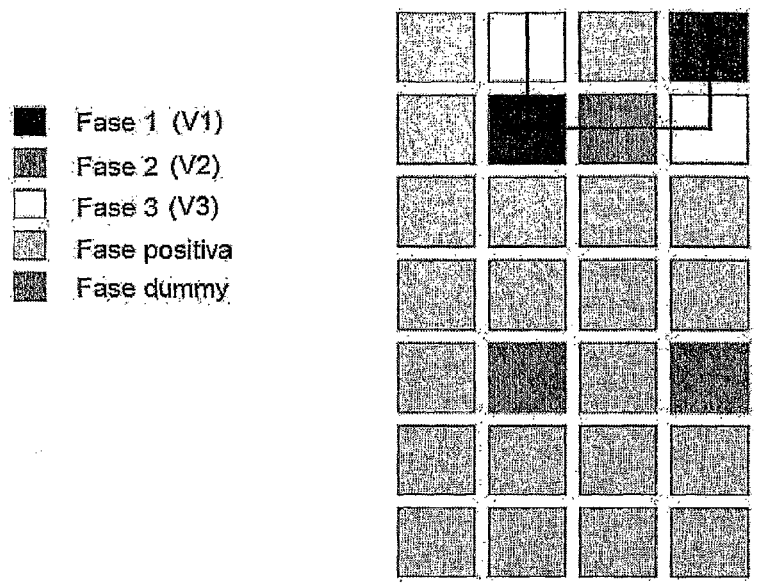
FIG. 42 shows a circumferential stretch of the loop that surrounds the active area of a chip constituting the apparatus for the manipulation of particles of FIG. 32.

Sheet 25, Fig. 42, each instance of "Fase" should be -- Phase --; "positiva" should be -- positive --; "Fase Dummy" should be -- Dummy Phase --.

In the Claims

In Claim 3: At Column 40, Line 34, "an diagonal" should be -- a diagonal --.

In Claim 8: At Column 41, Line 10, "iiii." should be -- iii. --.